(12) United States Patent
Aukerman et al.

(10) Patent No.: US 8,926,979 B2
(45) Date of Patent: Jan. 6, 2015

(54) TREATMENT OF CANCER OR PRE-MALIGNANT CONDITIONS USING ANTI-CD40 ANTIBODIES

(75) Inventors: Sharon Lea Aukerman, Moraga, CA (US); Mohammad Luqman, Danville, CA (US)

(73) Assignees: Novartis AG, Basel (CH); XOMA Technology Ltd., Berkeley, CA (US)

( * ) Notice: Subject to any disclaimer, the term of this patent is extended or adjusted under 35 U.S.C. 154(b) by 1838 days.

(21) Appl. No.: 12/092,247

(22) PCT Filed: Nov. 1, 2006

(86) PCT No.: PCT/US2006/042929
§ 371 (c)(1),
(2), (4) Date: Sep. 30, 2008

(87) PCT Pub. No.: WO2007/053767
PCT Pub. Date: May 10, 2007

(65) Prior Publication Data
US 2009/0117111 A1    May 7, 2009

Related U.S. Application Data

(60) Provisional application No. 60/732,730, filed on Nov. 1, 2005.

(51) Int. Cl.
A61K 39/395    (2006.01)
C07K 16/28     (2006.01)
A61K 39/00     (2006.01)

(52) U.S. Cl.
CPC ....... *C07K 16/2878* (2013.01); *A61K 2039/505* (2013.01); *C07K 2317/732* (2013.01)
USPC ............. 424/153.1; 424/130.1; 424/133.1; 424/141.1; 424/143.1; 424/144.1; 424/152.1; 424/173.1; 530/387.1; 530/387.3; 530/388.1; 530/388.2; 530/388.22; 530/388.7; 530/388.73

(58) Field of Classification Search
None
See application file for complete search history.

(56) References Cited

U.S. PATENT DOCUMENTS

| | | | |
|---|---|---|---|
| 5,801,227 A | 9/1998 | Fanslow, III et al. | |
| 5,874,082 A | 2/1999 | de Boer et al. | |
| 6,838,261 B1 * | 1/2005 | Siegall et al. | 435/69.6 |
| 7,063,845 B2 * | 6/2006 | Mikayama et al. | 424/153.1 |
| 2007/0098717 A1 | 5/2007 | Long et al. | |
| 2007/0098718 A1 | 5/2007 | Long et al. | |
| 2007/0110754 A1 | 5/2007 | Long et al. | |
| 2007/0218060 A1 | 9/2007 | Long et al. | |
| 2007/0231813 A1 * | 10/2007 | Cartron et al. | 435/6 |
| 2008/0057070 A1 | 3/2008 | Long et al. | |

FOREIGN PATENT DOCUMENTS

| | | |
|---|---|---|
| EP | 1 391 464 A1 | 2/2004 |
| WO | WO 94/01547 A3 | 1/1994 |
| WO | WO 95/17202 A1 | 6/1995 |
| WO | WO 96/18413 A1 | 6/1996 |
| WO | WO 97/31025 A1 | 8/1997 |
| WO | WO 99/42075 A2 | 8/1999 |
| WO | WO 01/34649 A3 | 5/2001 |
| WO | WO 01/83755 A3 | 11/2001 |
| WO | WO 02/04021 A1 | 1/2002 |
| WO | WO 02/22212 A2 | 3/2002 |
| WO | WO 02/28480 A2 | 4/2002 |
| WO | WO 02/28481 A2 | 4/2002 |
| WO | WO 02/28904 A3 | 4/2002 |
| WO | WO 02/28905 A2 | 4/2002 |
| WO | WO 02/060485 A2 | 8/2002 |
| WO | WO 02/088186 A1 | 11/2002 |
| WO | WO 03/029296 A1 | 4/2003 |
| WO | WO 03/035904 | 5/2003 |
| WO | WO 03/045978 A3 | 6/2003 |
| WO | WO 2005/044294 A2 | 5/2005 |

(Continued)

OTHER PUBLICATIONS

Dall'Ozzo et al., Cancer Research 64: 4664-4669, 2004.*
Louis et al., Aliment Pharmacol Ther 19: 511-519, 2004.*
Niwa, R., et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," Cancer Research, 2004, pp. 2127-2133, vol. 64.

(Continued)

*Primary Examiner* — Phillip Gambel
(74) *Attorney, Agent, or Firm* — Alston & Bird LLP

(57) ABSTRACT

Methods for treating a human patient for a cancer or pre-malignant condition that is associated with CD40-expressing cells are provided, where the human patient is heterozygous or homozygous for FcγRIIIa-158F (genotype V/F or F/F). Also provided are methods of inhibiting antibody production by B cells in a human patient who is heterozygous or homozygous for FcγRIIIa-158F (genotype V/F or F/F). The methods comprise administering to the human patient a therapeutically or prophylactically effective amount of an anti-CD40 antibody. Methods and kits for identifying a human patient with a cancer or pre-malignant condition that is treatable with an anti-CD40 antibody and which is refractory to treatment with rituximab (Rituxan®), as well as methods and kits for selecting an antibody therapy for treatment of a human patient having a cancer or pre-malignant condition that is refractory to treatment with rituximab (Rituxan®), are also provided. The methods of the present invention find use in treatment of cancers and pre-malignant conditions that are associated with CD40-expressing cells. These methods are particularly advantageous with respect to cancers and pre-malignant conditions that are associated with cells expressing both CD40 and CD20, as the methods enable the treatment of patients having a cancer or pre-malignant condition that is refractory to therapy with other oncotherapeutic agents such as anti-CD20 antibodies.

34 Claims, 22 Drawing Sheets

(56) References Cited

FOREIGN PATENT DOCUMENTS

| WO | WO 2005/044304 A2 | 5/2005 |
|---|---|---|
| WO | WO 2005/044305 A2 | 5/2005 |
| WO | WO 2005/044306 A2 | 5/2005 |
| WO | WO 2005/044307 A2 | 5/2005 |
| WO | WO 2005/044854 A2 | 5/2005 |
| WO | WO 2005/044855 A2 | 5/2005 |
| WO | WO 2007/053661 A2 | 5/2007 |

OTHER PUBLICATIONS

Law et al., "Preclinical Antilymphoma Activity of a Humanized Anti-CD40 Monoclonal Antibody, SGN-40," *Cancer Res*, 2005, pp. 8331-8338, vol. 65(18).
Balint, R., et al., "Antibody Engineering by Parsimonious Mutagenesis," *Gene*, 1993, pp. 109-118, vol. 137, No. 27.
Boon, L., et al., "Prevention of Experimental Autoimmune Encephalomyelitis in the Common Marmoset (*Callithrix jacchus*) Using a Chimeric Antagonist Monoclonal Antibody Against Human CD40 Is Associated with Altered B Cell Responses," *Journal of Immunology*, 2001, pp. 2942-2949, vol. 167, No. 5.
Cartron et al., "Therapeutic Activity of Humanized Anti-CD20 Monoclonal Antibody and Polymorphism In IGG FC Receptor FC Gamma RIIIa Gene," *Blood*, 2002, pp. 754-758, vol. 99, No. 3.
Database: Biosciences Information Service, Report for Accession No. PREV200400147707, Submitted Nov. 16, 2003.
Database: Biosciences Information Service, Report for Accession No. PREV200510267535, Submitted Nov. 2004.
Database: Biosciences Information Service, Report for Accession No. PREV200510271251, Submitted Nov. 2004.
Database: Biosciences Information Service, Report for Accession No. PREV200510271253, Submitted Nov. 2004.
Database: Biosciences Information Service, Report for Accession No. PREV200600183842, Submitted Nov. 2005.
Ellmark, P., et al., "Modulation of the CD40-CD40 Ligand Interaction Using Human Anti-CD40 Single-Chain Antibody Fragments Obtained from the n-CoDeR Phage Display Library," *Immunology*, 2002, pp. 456-463, vol. 106, No. 4.
Funakoshi, S., et al., "Differential In Vitro and In Vivo Antitumor Effects Mediated by Anti-CD40 and Anti-CD20 Monoclonal Antibodies Against Human B-Cell Lymphomas," *Journal of Immunology*, 1996, vol. 19, No. 2, pp. 93-101.
Gisselbrecht, C., et al., "Interleukin-2 Treatment in Lymphoma: A Phase II Multicenter Study," *Blood*, 1994, pp. 2081-2085, vol. 83, No. 8.
Hager A-C Malmborg, et al., "Affinity and Epitope Profiling of Mouse Anti-CD40 Monoclonal Antibodies," *Scandinavian Journal of Immunology*, 2003, pp. 517-524, vol. 57, No. 6.
Hayashi et al., "Recombinant Humanized Anti-CD40 Monoclonal Antibody Triggers Autologous Antibody-Dependent Cell-Mediated Cytotoxicity Against Multiple Myeloma Cells," *British Journal of Haematology*, 2003, pp. 592-596, vol. 121, No. 4.
Little, M., et al., "Of Mice and Men: Hybridoma and Recombinant Antibodies," *Review Immunology Today*, 2000, pp. 364-370, vol. 21.
Maloney, D.G., et al., "IDEC-C2B8: Results of a Phase I Multiple-Dose Trial in Patients with Relapsed Non-Hodgkin's Lymphoma," *Journal of Clinical Oncology*, 1997, vol. 15, No. 10, pp. 3266-3274.
Rosenberg, S.A., et al., "A Progress Report on the Treatment of 157 Patients with Advanced Cancer Using Lymphokine-Activated Killer Cells and Interleukin-2 or High-Dose Interleukin-2 Alone," *The New England Journal of Medicine*, 1987, pp. 889-897, vol. 316, No. 15.
Tai et al., "Mechanisms by which SGN-40, a Humanized Anti-CD40 Antibody, Induces Cytotoxicity in Human Multiple Myeloma Cells: Clinical Implications," *Cancer Research*, 2004, pp. 2846-2852, vol. 64, No. 8.
Tai et al., "A Fully Human Antagonist Anti-CD40 Antibody Triggers Significant Antitumor Activity Against Human Multiple Myeloma," *Blood*, 2004; Database: Biosciences Information Service, Report for Accession No. PREV200510270384, Submitted Nov. 16, 2004.
Tai et al., "Human Anti-CD40 Antagonist Antibody Triggers Significant Antitumor Activity Against Human Multiple Myeloma," *Cancer Research*, 2005, pp. 5898-5906, vol. 65, No. 13.
Weng Wen-Kai, et al., "Human anti-CD40 Antagonistic Antibodies Inhibit the Proliferation of Human B Cell Non-Hodgkin's Lymphoma," *Blood*, 2001, p. 466a, vol. 98, No. 11, Part 1, Abstract #1947.

\* cited by examiner

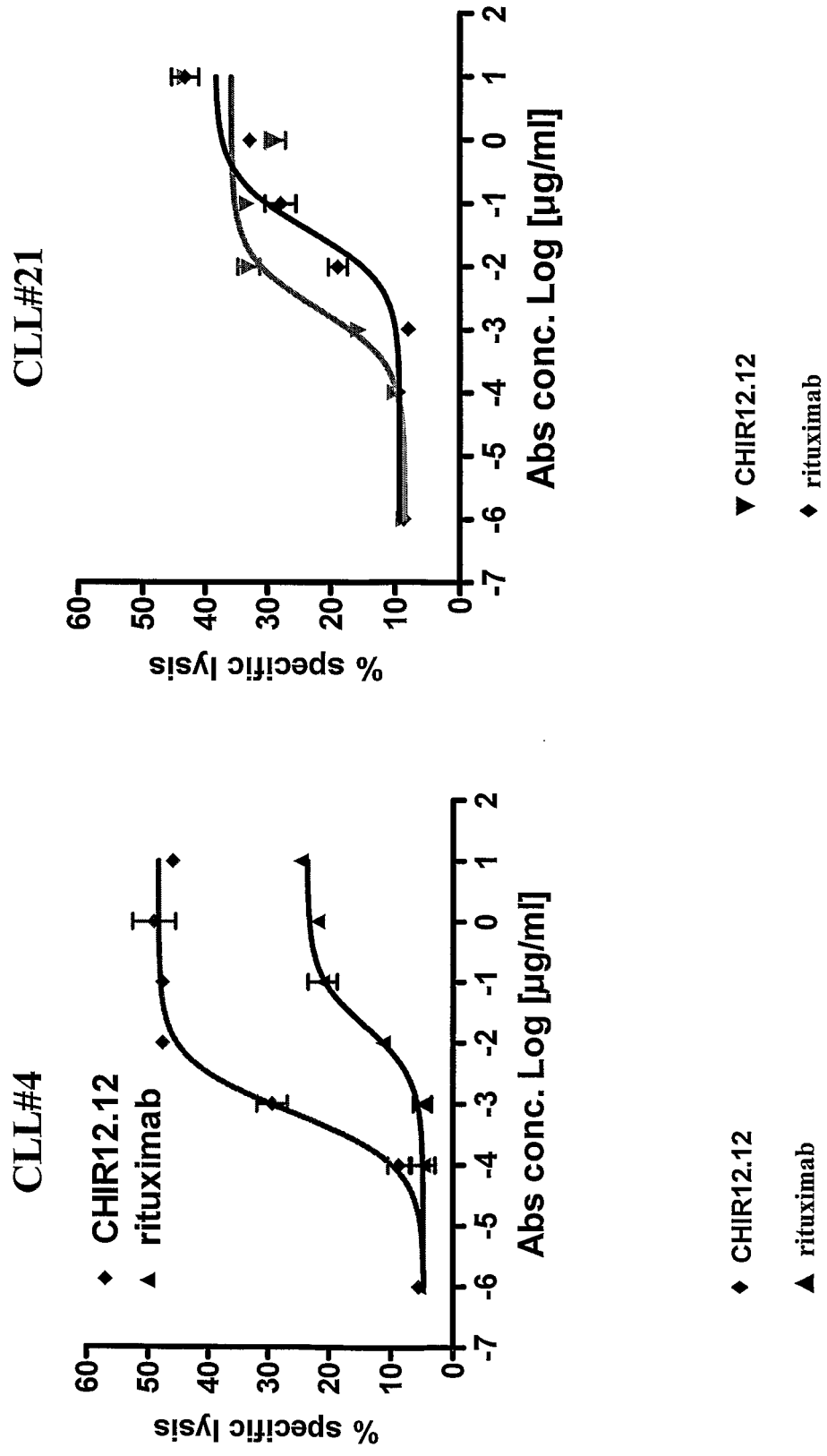
Figure 2A: CHIR-12.12 mediates greater ADCC than rituximab against CLL patient cells

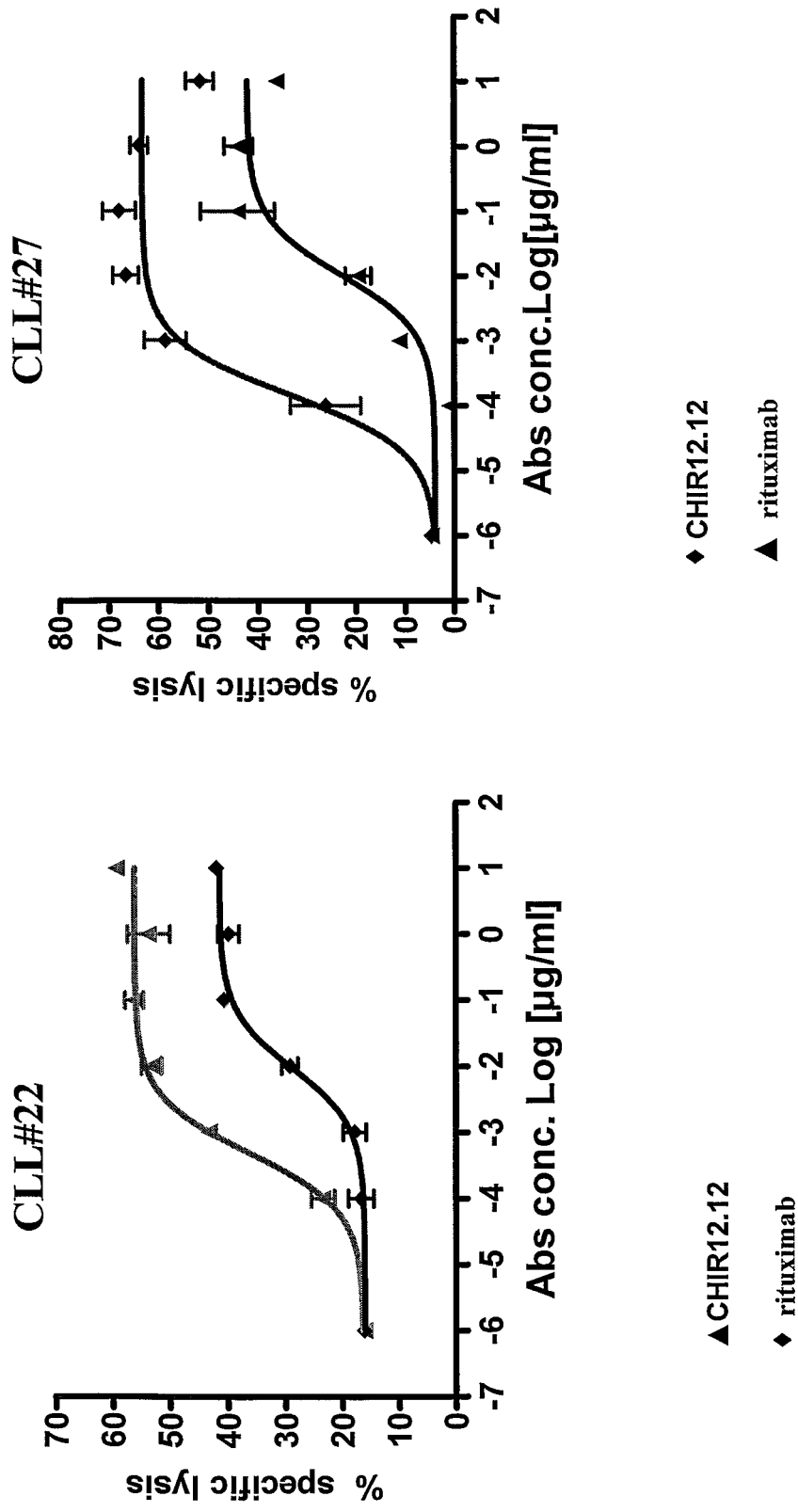
Figure 2B: CHIR-12.12 mediates greater ADCC than rituximab against CLL patient cells

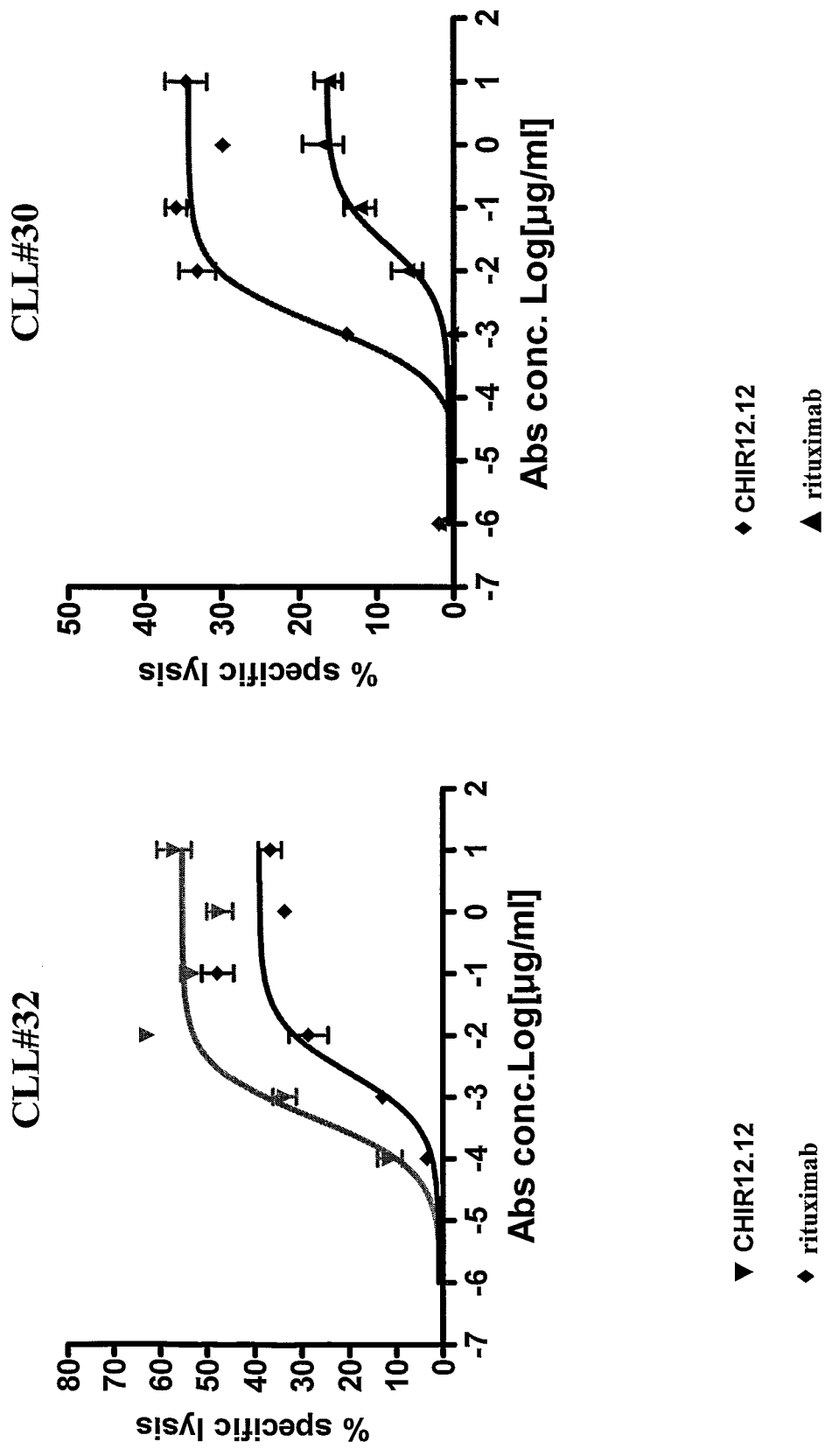
Figure 2C: CHIR-12.12 mediates greater ADCC than rituximab against CLL patient cells

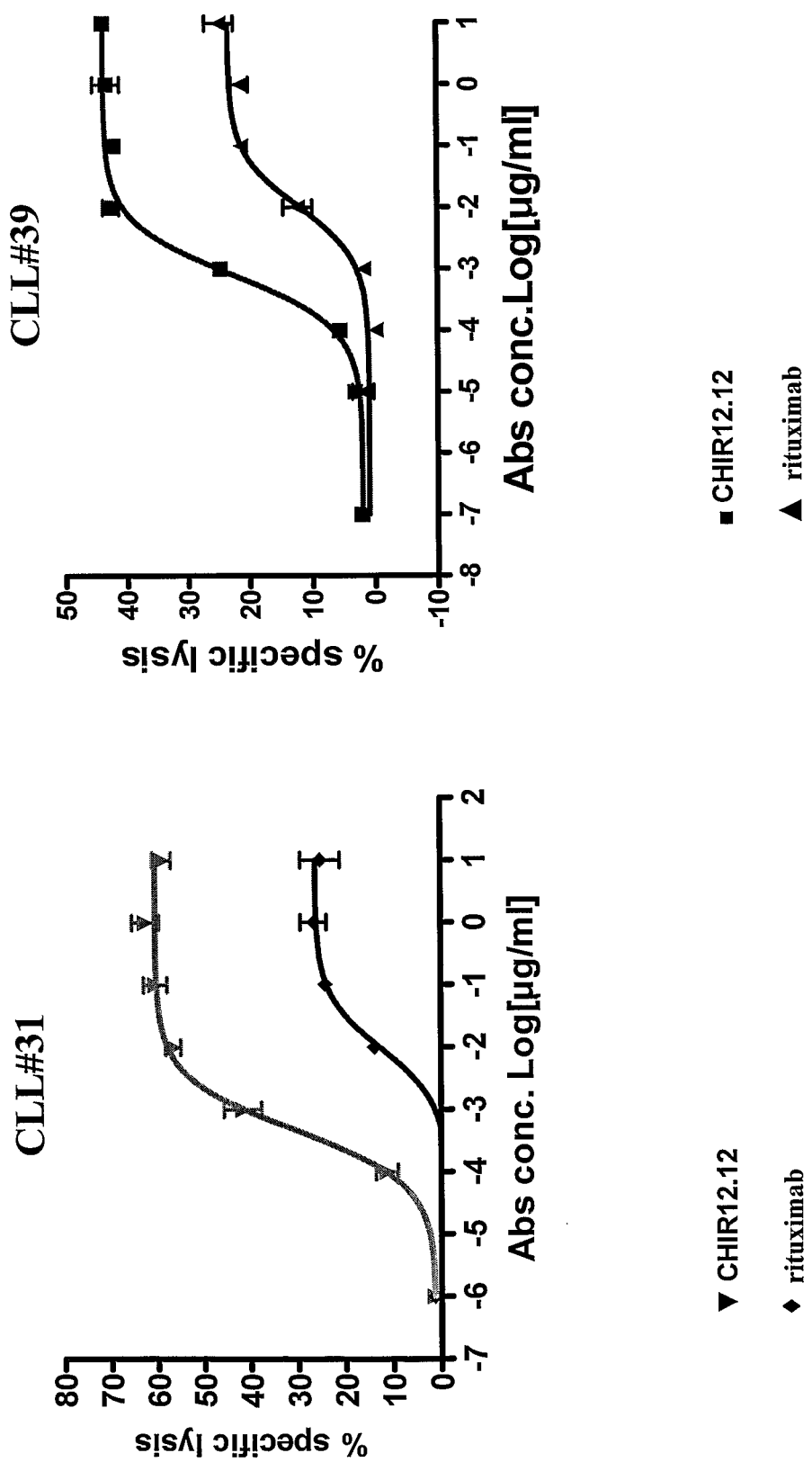
Figure 2D: CHIR-12.12 mediates greater ADCC than rituximab against CLL patient cells Figure 3: Comparative ADCC of CHIR-12.12 and rituximab against CLL patient cells (n=9) by human NK cells from multiple donors

| Abs conc.(ug/ml) | Fraction of Rituximab mediated lysis compare to CHIR-12.12 | CHIR-12.12 EC50)pM | Rituximab EC50(pM) |
|---|---|---|---|
| 10 | 0.57 ± 0.18 | 13.25 ± 16.73 | 147.22 ± 135.6 |
| 1 | 0.62 ± 0.24 | | |
| 0.1 | 0.56 ± 0.21 | | |
| 0.01 | 0.29 ± 0.14 | | |
| 0.001 | 0.14 ± 0.11 | | |
| 0.0001 | 0.71 ± 2.18 | | |
| 0.00001 | -0.45 ± 0.49 | | |

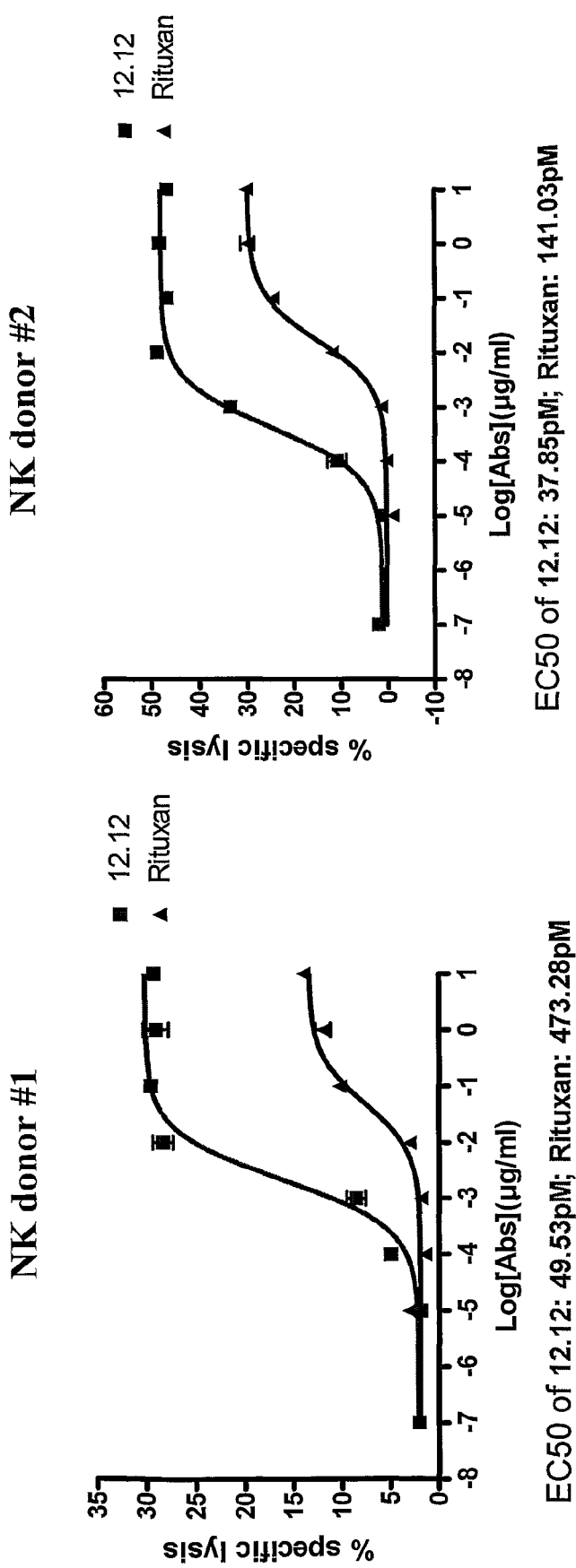
Figure 4: NK donor variation in ADCC activities in the same target cells (CLL#33)

Figure 5: Quantitation of CD40 and CD20 molecules expressed on CLL patient cells and normal B cells

| CLL patient# | CHIR-12.12 CD40 molecules | Rituximab CD20 molecules |
|---|---|---|
| 30 | 684 ± 8 | 9584 ± 44 |
| 31 | 1590 ± 79 | 6838 ± 135 |
| 27 | 1158 ± 57 | 1455 ± 126 |
| 32 | 2860 ± 38 | 28494 ± 547 |
| 33 | 1421 ± 201 | 5799 ± 160 |
| human B cells(n=2) | 4067 ± 438 | 68358 ± 22830 |

Figure 6: Relative expression of CD40 and CD20 molecules on CLL patient cells and ADCC activity

| CLL patient # | % Max lysis | | Difference between CHIR-12.12 and Rituximab | Ratio of target molecules CD20/CD40 |
|---|---|---|---|---|
| | CHIR-12.12 | Rituximab | | |
| 4 | 46.35 | 20.15 | 26.2 | N/A |
| 21 | 32.9 | 32.8 | 0.1 | N/A |
| 22 | 46.65 | 31.08 | 15.57 | N/A |
| 27 | 79.87 | 56.04 | 23.83 | 1.26 |
| 32 | 56.92 | 49.97 | 6.95 | 9.96 |
| 30 | 37.6 | 21.33 | 16.27 | 14.01 |
| 31 | 63.4 | 27.27 | 36.13 | 4.3 |
| 33(1) | 27.71 | 12.33 | 15.38 | |
| 33(2) | 48.57 | 28.63 | 19.94 | 4.08 |
| 39 | 44.18 | 21.13 | 23.05 | N/A |
| Average | 48.42 | 30.07 | | |
| SD | 15.27 | 13.57 | | |

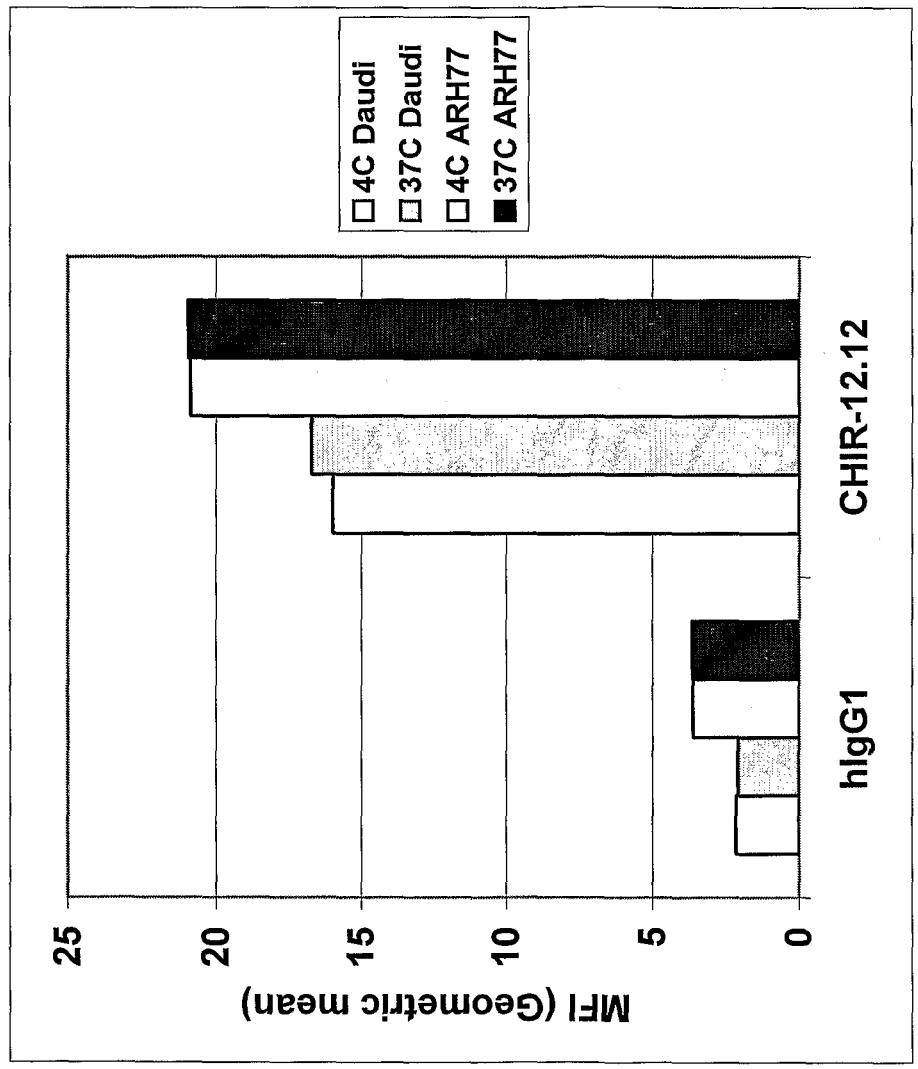
Figure 7: Levels of cell-surface bound CHIR-12.12 (measured as fluorescence intensity) after 3 hours of incubation at 4°C and 37°C

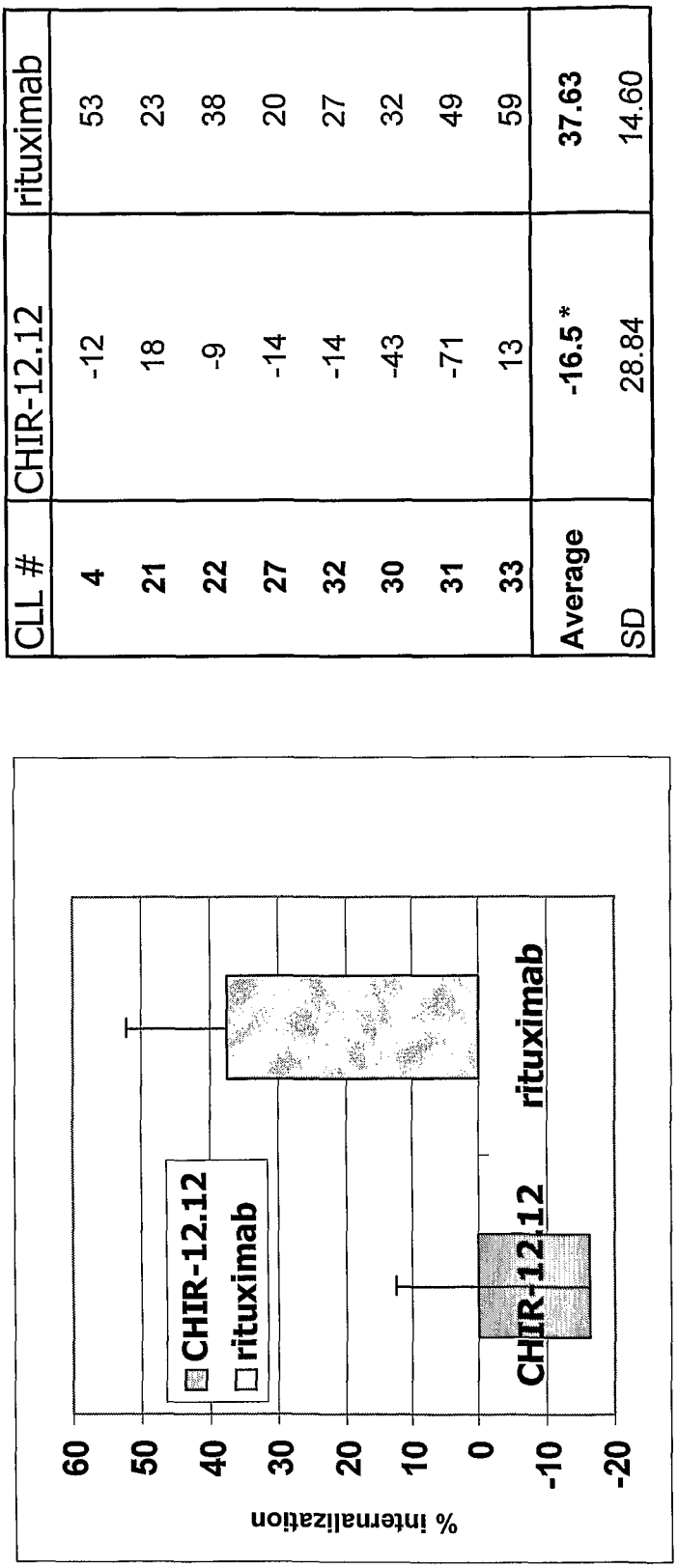

Figure 8: Percentage internalization of CHIR-12.12 and rituximab in CLL patient cells (n=8): FACS

| CLL # | CHIR-12.12 | rituximab |
|---|---|---|
| 4 | -12 | 53 |
| 21 | 18 | 23 |
| 22 | -9 | 38 |
| 27 | -14 | 20 |
| 32 | -14 | 27 |
| 30 | -43 | 32 |
| 31 | -71 | 49 |
| 33 | 13 | 59 |
| Average | -16.5 * | 37.63 |
| SD | 28.84 | 14.60 |

% of internalization=100*{(GMF of test Abs at 4°C-GMF of isotype Abs at 4°C)-(GMF of test Abs at 37°C-GMF of isotype Abs at 37°C)}/ (GMF of test Abs at 4°C-GMF of isotype Abs at 4°C)

GMF: Geometric mean fluorescence intensity

*negative % internalization indicates greater binding of CHIR-12.12 at 37°C compare to 4°C

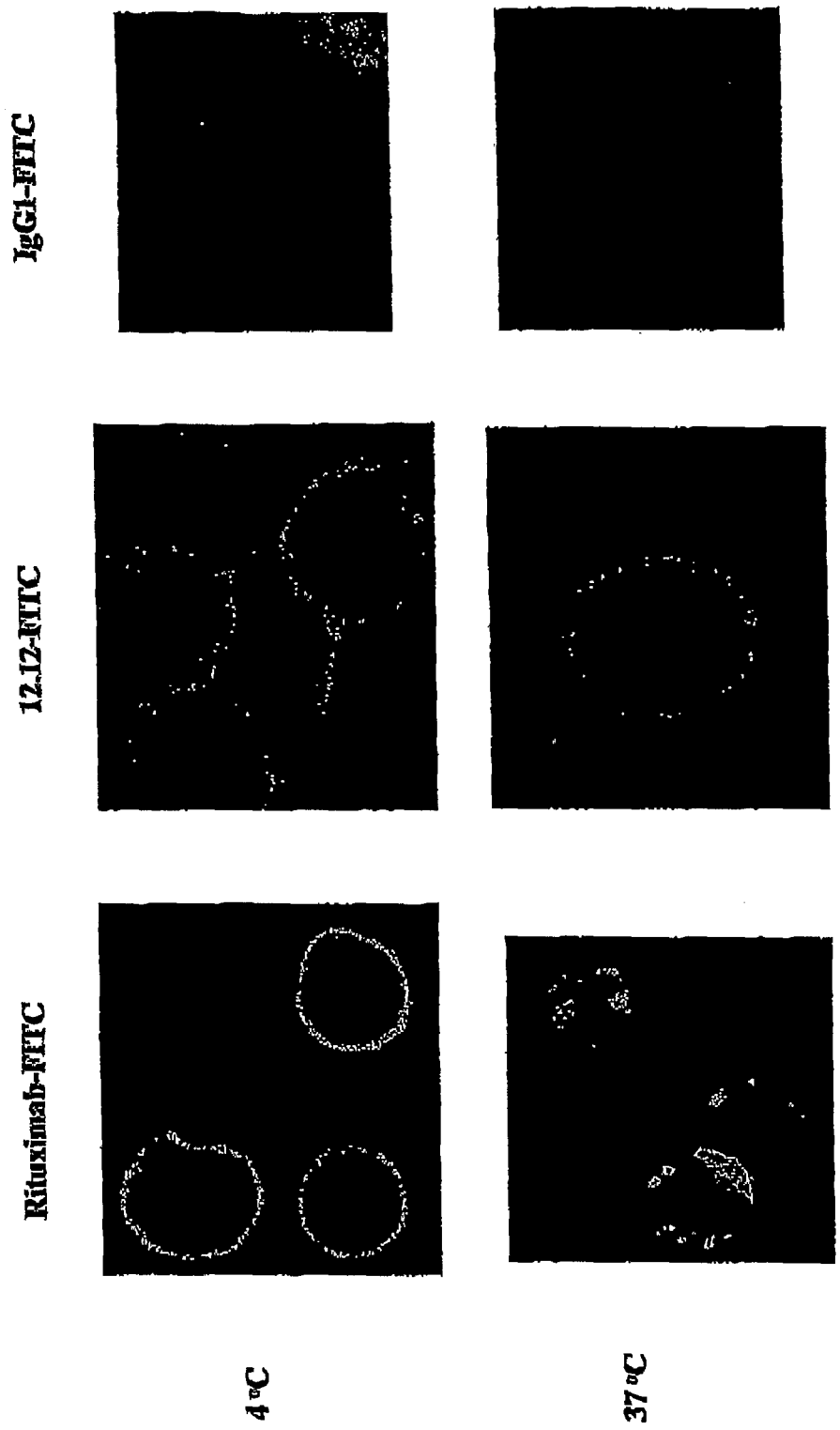
Figure 9: Internalization of CHIR-12.12 and rituximab in normal human B cells: confocal microscope

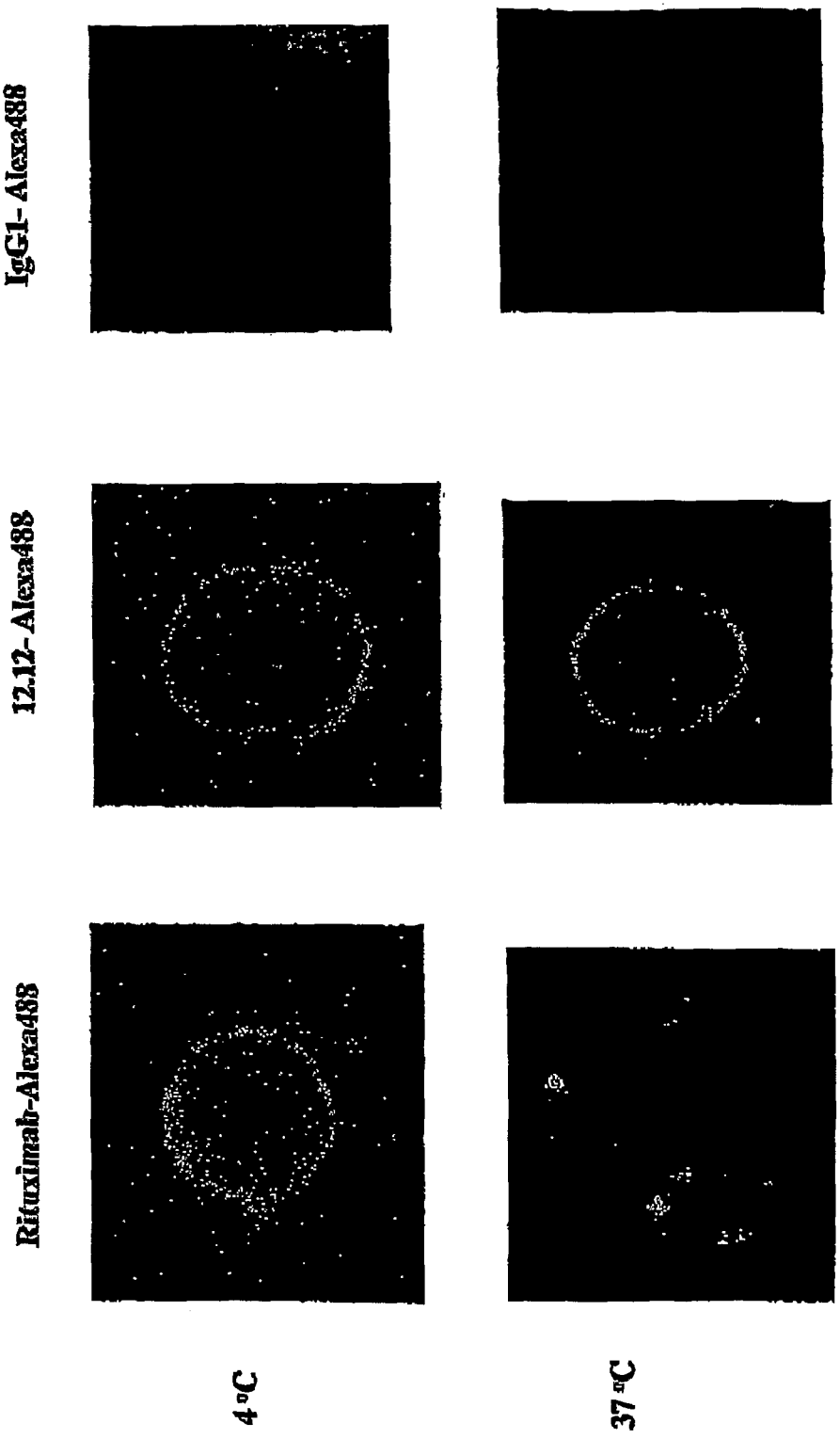

Figure 11: Relationship between ADCC activity and internalization

| CLL patient # | % Max lysis | | Difference between CHIR-12.12 and Rituximab | % Internalization | |
|---|---|---|---|---|---|
| | CHIR-12.12 | Rituximab | | CHIR-12.12 | Rituximab |
| 4 | 46.35 | 20.15 | 26.2 | No | 53 |
| 21 | 32.9 | 32.8 | 0.1 | 18 | 23 |
| 22 | 46.65 | 31.08 | 15.57 | No | 38 |
| 27 | 79.87 | 56.04 | 23.83 | No | 20 |
| 32 | 56.92 | 49.97 | 6.95 | No | 27 |
| 30 | 37.6 | 21.33 | 16.27 | No | 32 |
| 31 | 63.4 | 27.27 | 36.13 | No | 49 |
| 33(1) | 27.71 | 12.33 | 15.38 | | |
| 33(2) | 48.57 | 28.63 | 19.94 | 13 | 59 |
| 39 | 44.18 | 21.13 | 23.05 | N/A | N/A |

Figure 14: Comparative ADCC of CHIR-12.12 and rituximab against CLL patient cells (n=9) by human NK cells from multiple donors with variant FcRγ IIIa genotype

| CLL patient # | % Max lysis | | | EC 50(pM) | | | NK donor FcRγIIIa genotype |
|---|---|---|---|---|---|---|---|
| | CHIR-12.12 | Rituximab | Difference between CHIR-12.12 and Ritxximab | CHIR-12.12 | Rituximab | Rituximab vs CHIR-12.12 fold | |
| 4 | 46.35 | 20.15 | 26.2 | 5.12 | 127.64 | 25 | FF |
| 21 | 32.9 | 32.8 | 0.1 | 14.86 | 272.68 | 18 | FF |
| 22 | 46.65 | 31.08 | 15.57 | 3.24 | 62.08 | 19 | FF |
| 27 | 79.87 | 56.04 | 23.83 | 0.99 | 71.54 | 72 | VF |
| 32 | 56.92 | 49.97 | 6.95 | 3.14 | 16.58 | 5 | VF |
| 30 | 37.6 | 21.33 | 16.27 | 8.87 | 170.34 | 19 | VV |
| 31 | 63.4 | 27.27 | 36.13 | 3.23 | 64.59 | 20 | VV |
| 33(1) | 27.71 | 12.33 | 15.38 | 49.53 | 473.28 | 10 | FF |
| 33(2) | 48.57 | 28.63 | 19.94 | 37.85 | 141.03 | 4 | VV |
| 39 | 44.18 | 21.13 | 23.05 | 5.63 | 72.42 | 13 | VF |
| Mean | 48.42 | 30.07 | 18.34 | 13.25 | 147.22 | 20.53 | |
| SD | 15.27 | 13.57 | 10.09 | 16.73 | 135.60 | 19.43 | |

SEQUENCE LISTING

```
<160> NUMBER OF SEQ ID NOS: 9

<210> SEQ ID NO 1
<211> LENGTH: 720
<212> TYPE: DNA
<213> ORGANISM: Artificial Sequence
<220> FEATURE:
<223> OTHER INFORMATION: Coding sequence for light chain of 12.12 human
      anti-CD40 antibody
<221> NAME/KEY: CDS
<222> LOCATION: (1)...(720)

<400> SEQUENCE: 1 atg gcg ctc cct gct cag ctc ctg ggg ctg cta atg ctc tgg gtc tct       48
Met Ala Leu Pro Ala Gln Leu Leu Gly Leu Leu Met Leu Trp Val Ser
1               5                   10                  15 gga tcc agt ggg gat att gtg atg act cag tct cca ctc tcc ctg acc       96
Gly Ser Ser Gly Asp Ile Val Met Thr Gln Ser Pro Leu Ser Leu Thr
            20                  25                  30 gtc acc cct gga gag ccg gcc tcc atc tcc tgc agg tcc agt cag agc      144
Val Thr Pro Gly Glu Pro Ala Ser Ile Ser Cys Arg Ser Ser Gln Ser
        35                  40                  45 ctc ctg tat agt aat gga tac aac tat ttg gat tgg tac ctg cag aag      192
Leu Leu Tyr Ser Asn Gly Tyr Asn Tyr Leu Asp Trp Tyr Leu Gln Lys
    50                  55                  60 cca ggg cag tct cca cag gtc ctg atc tct ttg ggt tct aat cgg gcc      240
Pro Gly Gln Ser Pro Gln Val Leu Ile Ser Leu Gly Ser Asn Arg Ala
65                  70                  75                  80 tcc ggg gtc cct gac agg ttc agt ggc agt gga tca ggc aca gat ttt      288
Ser Gly Val Pro Asp Arg Phe Ser Gly Ser Gly Ser Gly Thr Asp Phe
                85                  90                  95 aca ctg aaa atc agc aga gtg gag gct gag gat gtt ggg gtt tat tac      336
Thr Leu Lys Ile Ser Arg Val Glu Ala Glu Asp Val Gly Val Tyr Tyr
            100                 105                 110 tgc atg caa gct cga caa act cca ttc act ttc ggc cct ggg acc aaa      384
Cys Met Gln Ala Arg Gln Thr Pro Phe Thr Phe Gly Pro Gly Thr Lys
        115                 120                 125 gtg gat atc aga cga act gtg gct gca cca tct gtc ttc atc ttc ccg      432
Val Asp Ile Arg Arg Thr Val Ala Ala Pro Ser Val Phe Ile Phe Pro
    130                 135                 140 cca tct gat gag cag ttg aaa tct gga act gcc tct gtt gtg tgc ctg      480
Pro Ser Asp Glu Gln Leu Lys Ser Gly Thr Ala Ser Val Val Cys Leu
145                 150                 155                 160 ctg aat aac ttc tat ccc aga gag gcc aaa gta cag tgg aag gtg gat      528
Leu Asn Asn Phe Tyr Pro Arg Glu Ala Lys Val Gln Trp Lys Val Asp
                165                 170                 175 aac gcc ctc caa tcg ggt aac tcc cag gag agt gtc aca gag cag gac      576
Asn Ala Leu Gln Ser Gly Asn Ser Gln Glu Ser Val Thr Glu Gln Asp
            180                 185                 190 agc aag gac agc acc tac agc ctc agc agc acc ctg acg ctg agc aaa      624
Ser Lys Asp Ser Thr Tyr Ser Leu Ser Ser Thr Leu Thr Leu Ser Lys
        195                 200                 205 gca gac tac gag aaa cac aaa gtc tac gcc tgc gaa gtc acc cat cag      672
Ala Asp Tyr Glu Lys His Lys Val Tyr Ala Cys Glu Val Thr His Gln
    210                 215                 220 ggc ctg agc tcg ccc gtc aca aag agc ttc aac agg gga gag tgt tag      720
Gly Leu Ser Ser Pro Val Thr Lys Ser Phe Asn Arg Gly Glu Cys *
225                 230                 235
```

```
<210> SEQ ID NO 2
<211> LENGTH: 239
<212> TYPE: PRT
<213> ORGANISM: Artificial Sequence
<220> FEATURE:
<223> OTHER INFORMATION: Light chain of 12.12 human anti-CD40 antibody

<400> SEQUENCE: 2

Met Ala Leu Pro Ala Gln Leu Leu Gly Leu Leu Met Leu Trp Val Ser
 1               5                  10                  15

Gly Ser Ser Gly Asp Ile Val Met Thr Gln Ser Pro Leu Ser Leu Thr
            20                  25                  30

Val Thr Pro Gly Glu Pro Ala Ser Ile Ser Cys Arg Ser Ser Gln Ser
        35                  40                  45

Leu Leu Tyr Ser Asn Gly Tyr Asn Tyr Leu Asp Trp Tyr Leu Gln Lys
    50                  55                  60

Pro Gly Gln Ser Pro Gln Val Leu Ile Ser Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Arg Gln Thr Pro Phe Thr Phe Gly Pro Gly Thr Lys
        115                 120                 125

Val Asp Ile Arg Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 3
<211> LENGTH: 2016
<212> TYPE: DNA
<213> ORGANISM: Artificial Sequence
<220> FEATURE:
<223> OTHER INFORMATION: Coding sequence for heavy chain of 12.12 human
      anti-CD40 antibody (with introns)

<400> SEQUENCE: 3 atg gag ttt ggg ctg agc tgg gtt ttc ctt gtt gct att tta aga ggt      48 gtc cag tgt cag gtg cag ttg gtg gag tct ggg gga ggc gtg gtc cag      96 cct ggg agg tcc ctg aga ctc tcc tgt gca gcc tct gga ttc acc ttc     144 agt agc tat ggc atg cac tgg gtc cgc cag gct cca ggc aag ggg ctg     192 gag tgg gtg gca gtt ata tca tat gag gaa agt aat aga tac cat gca     240 gac tcc gtg aag ggc cga ttc acc atc tcc aga gac aat tcc aag atc     288 acg ctg tat ctg caa atg aac agc ctc aga act gag gac acg gct gtg     336
```

```
tat tac tgt gcg aga gat ggg ggt ata gca gca cct ggg cct gac tac    384
tgg ggc cag gga acc ctg gtc acc gtc tcc tca gca agt acc aag ggc    432
cca tcc gtc ttc ccc ctg gcg ccc gct agc aag agc acc tct ggg ggc    480
aca gcg gcc ctg ggc tgc ctg gtc aag gac tac ttc ccc gaa ccg gtg    528
acg gtg tcg tgg aac tca ggc gcc ctg acc agc ggc gtg cac acc ttc    576
ccg gct gtc cta cag tcc tca gga ctc tac tcc ctc agc agc gtg gtg    624
acc gtg ccc tcc agc agc ttg ggc acc cag acc tac atc tgc aac gtg    672
aat cac aag ccc agc aac acc aag gtg gac aag aga gtt ggt gag agg    720
cca gca cag gga ggg agg gtg tct gct gga agc cag gct cag cgc tcc    768
tgc ctg gac gca tcc cgg cta tgc agt ccc agt cca ggg cag caa ggc    816
agg ccc cgt ctg cct ctt cac ccg gag gcc tct gcc cgc ccc act cat    864
gct cag gga gag ggt ctt ctg gct ttt ccc cag gct ctg ggc agg ca    912
cag gct agg tgc ccc taa ccc agg ccc tgc aca caa agg ggc agg tgc    960
tgg gct cag acc tgc caa gag cca tat ccg gga gga ccc tgc ccc tga   1008
cct aag ccc acc cca agg cca aaa ctc tcc act ccc tca gct cgg aca   1056
cct tct ctc ctc cca gat tct agt aac tcc aaa tct tct ctc tgc aga   1104
gcc caa atc ttg tga caa aac tca cac atg ccc acc gtg ccc agg taa   1152
gcc agc cca ggc ctc gcc ctc cag ctc aag gcg gga cag gtg ccc tag   1200
agt agc ctg cat cca ggg aca ggc ccc agc cgg gtg ctg aca cgt cca   1248
cct cca tct ctt cct cag cac ctg aac tcc tgg ggg gac cgt cag tct   1296
tcc tct tcc ccc caa aac cca agg aca ccc tca tga tct ccc gga ccc   1344
ctg agg tca cat gcg tgg tgg tgg acg tga gcc acg aag acc ctg agg   1392
tca agt tca act ggt acg tgg acg gcg tgg agg tgc ata atg cca aga   1440
caa agc cgc ggg agg agc agt aca aca gca cgt acc gtg tgg tca gcg   1488
tcc tca ccg tcc tgc acc agg act ggc tga atg gca agg agt aca gt   1536
gca agg tct cca aca aag ccc tcc cag ccc cca tcg aga aaa cca tct   1584
cca aag cca aag gtg gga ccc gtg ggg tgc gag ggc cac atg gac aga   1632
ggc cgg ctc ggc cca ccc tct gcc ctg aga gtg acc gct gta cca acc   1680
tct gtc cct aca ggg cag ccc cga gaa cca cag gtg tac acc ctg ccc   1728
cca tcc cgg gag gag atg acc aag aac cag gtc agc ctg acc tgc ctg   1776
gtc aaa ggc ttc tat ccc agc gac atc gcc gtg gag tgg gag agc aat   1824
ggg cag ccg gag aac aac tac aag acc acg cct ccc gtg ctg gac tcc   1872
gac ggc tcc ttc ttc ctc tat agc aag ctc acc gtg gac aag agc agg   1920
tgg cag cag ggg aac gtc ttc tca tgc tcc gtg atg cat gag gct ctg   1968
cac aac cac tac acg cag aag agc ctc tcc ctg tct ccg ggt aaa tga   2016
```

<210> SEQ ID NO 4
<211> LENGTH: 469
<212> TYPE: PRT
<213> ORGANISM: Artificial Sequence
<220> FEATURE:
<223> OTHER INFORMATION: Heavy chain of 12.12 human anti-CD40 antibody

<400> SEQUENCE: 4

```
Met Glu Phe Gly Leu Ser Trp Val Phe Leu Val Ala Ile Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
            115                 120                 125

Trp Gly Gln Gly Thr Leu Val Thr Val Ser Ser Ala Ser Thr Lys Gly
    130                 135                 140

Pro Ser Val Phe Pro Leu Ala Pro Ala Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
    275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
    355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415
```

-continued

```
Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 5
<211> LENGTH: 469
<212> TYPE: PRT
<213> ORGANISM: Artificial Sequence
<220> FEATURE:
<223> OTHER INFORMATION: Heavy chain of variant of 12.12 human anti-CD40
      antibody

<400> SEQUENCE: 5

Met Glu Phe Gly Leu Ser Trp Val Phe Leu Val Ala Ile Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300
```

```
Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
    355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 6
<211> LENGTH: 612
<212> TYPE: DNA
<213> ORGANISM: Homo sapiens
<220> FEATURE:
<221> NAME/KEY: CDS
<222> LOCATION: (1)...(612)
<221> NAME/KEY: misc_feature
<222> LOCATION: (0)...(0)
<223> OTHER INFORMATION: Coding sequence for short isoform of human CD40

<400> SEQUENCE: 6 atg gtt cgt ctg cct ctg cag tgc gtc ctc tgg ggc tgc ttg ctg acc        48
Met Val Arg Leu Pro Leu Gln Cys Val Leu Trp Gly Cys Leu Leu Thr
1               5                   10                  15 gct gtc cat cca gaa cca ccc act gca tgc aga gaa aaa cag tac cta        96
Ala Val His Pro Glu Pro Pro Thr Ala Cys Arg Glu Lys Gln Tyr Leu
                20                  25                  30 ata aac agt cag tgc tgt tct ttg tgc cag cca gga cag aaa ctg gtg       144
Ile Asn Ser Gln Cys Cys Ser Leu Cys Gln Pro Gly Gln Lys Leu Val
            35                  40                  45 agt gac tgc aca gag ttc act gaa acg gaa tgc ctt cct tgc ggt gaa       192
Ser Asp Cys Thr Glu Phe Thr Glu Thr Glu Cys Leu Pro Cys Gly Glu
        50                  55                  60 agc gaa ttc cta gac acc tgg aac aga gag aca cac tgc cac cag cac       240
Ser Glu Phe Leu Asp Thr Trp Asn Arg Glu Thr His Cys His Gln His
65                  70                  75                  80 aaa tac tgc gac ccc aac cta ggg ctt cgg gtc cag cag aag ggc acc       288
Lys Tyr Cys Asp Pro Asn Leu Gly Leu Arg Val Gln Gln Lys Gly Thr
                85                  90                  95 tca gaa aca gac acc atc tgc acc tgt gaa gaa ggc tgg cac tgt acg       336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc       384
Ser Glu Ala Cys Glu Ser Cys Val Leu His Arg Ser Cys Ser Pro Gly
        115                 120                 125
```

```
ttt ggg gtc aag cag att gct aca ggg gtt tct gat acc atc tgc gag    432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa    480
Pro Cys Pro Val Gly Phe Phe Ser Asn Val Ser Ser Ala Phe Glu Lys
145                 150                 155                 160 tgt cac cct tgg aca agg tcc cca gga tcg gct gag agc cct ggt ggt    528
Cys His Pro Trp Thr Arg Ser Pro Gly Ser Ala Glu Ser Pro Gly Gly
                165                 170                 175 gat ccc cat cat ctt cgg gat cct gtt tgc cat cct ctt ggt gct ggt    576
Asp Pro His His Leu Arg Asp Pro Val Cys His Pro Leu Gly Ala Gly
            180                 185                 190 ctt tat caa aaa ggt ggc caa gaa gcc aac caa taa                    612
Leu Tyr Gln Lys Gly Gly Gln Glu Ala Asn Gln *
        195                 200
```

<210> SEQ ID NO 7
<211> LENGTH: 203
<212> TYPE: PRT
<213> ORGANISM: Homo sapiens

<400> SEQUENCE: 7

```
Met Val Arg Leu Pro Leu Gln Cys Val Leu Trp Gly Cys Leu Leu Thr
  1               5                  10                  15

Ala Val His Pro Glu Pro Pro Thr Ala Cys Arg Glu Lys Gln Tyr Leu
             20                  25                  30

Ile Asn Ser Gln Cys Cys Ser Leu Cys Gln Pro Gly Gln Lys Leu Val
         35                  40                  45

Ser Asp Cys Thr Glu Phe Thr Glu Thr Glu Cys Leu Pro Cys Gly Glu
     50                  55                  60

Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Arg Ser Pro Gly Ser Ala Glu Ser Pro Gly Gly
                165                 170                 175

Asp Pro His His Leu Arg Asp Pro Val Cys His Pro Leu Gly Ala Gly
            180                 185                 190

Leu Tyr Gln Lys Gly Gly Gln Glu Ala Asn Gln
        195                 200
```

<210> SEQ ID NO 8
<211> LENGTH: 834
<212> TYPE: DNA
<213> ORGANISM: Homo sapiens
<220> FEATURE:
<221> NAME/KEY: CDS
<222> LOCATION: (1)...(834)
<221> NAME/KEY: misc_feature
<222> LOCATION: (0)...(0)
<223> OTHER INFORMATION: Coding sequence for long isoform of human CD40

<400> SEQUENCE: 8

```
atg gtt cgt ctg cct ctg cag tgc gtc ctc tgg ggc tgc ttg ctg acc    48
Met Val Arg Leu Pro Leu Gln Cys Val Leu Trp Gly Cys Leu Leu Thr
1               5                   10                  15 gct gtc cat cca gaa cca ccc act gca tgc aga gaa aaa cag tac cta    96
Ala Val His Pro Glu Pro Pro Thr Ala Cys Arg Glu Lys Gln Tyr Leu
            20                  25                  30 ata aac agt cag tgc tgt tct ttg tgc cag cca gga cag aaa ctg gtg   144
Ile Asn Ser Gln Cys Cys Ser Leu Cys Gln Pro Gly Gln Lys Leu Val
        35                  40                  45 agt gac tgc aca gag ttc act gaa acg gaa tgc ctt cct tgc ggt gaa   192
Ser Asp Cys Thr Glu Phe Thr Glu Thr Glu Cys Leu Pro Cys Gly Glu
50                  55                  60 agc gaa ttc cta gac acc tgg aac aga gag aca cac tgc cac cag cac   240
Ser Glu Phe Leu Asp Thr Trp Asn Arg Glu Thr His Cys His Gln His
65                  70                  75                  80 aaa tac tgc gac ccc aac cta ggg ctt cgg gtc cag cag aag ggc acc   288
Lys Tyr Cys Asp Pro Asn Leu Gly Leu Arg Val Gln Gln Lys Gly Thr
                85                  90                  95 tca gaa aca gac acc atc tgc acc tgt gaa gaa ggc tgg cac tgt acg   336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc   384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag   432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa   480
Pro Cys Pro Val Gly Phe Phe Ser Asn Val Ser Ser Ala Phe Glu Lys
145                 150                 155                 160 tgt cac cct tgg aca agc tgt gag acc aaa gac ctg gtt gtg caa cag   528
Cys His Pro Trp Thr Ser Cys Glu Thr Lys Asp Leu Val Val Gln Gln
                165                 170                 175 gca ggc aca aac aag act gat gtt gtc tgt ggt ccc cag gat cgg ctg   576
Ala Gly Thr Asn Lys Thr Asp Val Val Cys Gly Pro Gln Asp Arg Leu
            180                 185                 190 aga gcc ctg gtg gtg atc ccc atc atc ttc ggg atc ctg ttt gcc atc   624
Arg Ala Leu Val Val Ile Pro Ile Ile Phe Gly Ile Leu Phe Ala Ile
        195                 200                 205 ctc ttg gtg ctg gtc ttt atc aaa aag gtg gcc aag aag cca acc aat   672
Leu Leu Val Leu Val Phe Ile Lys Lys Val Ala Lys Lys Pro Thr Asn
    210                 215                 220 aag gcc ccc cac ccc aag cag gaa ccc cag gag atc aat ttt ccc gac   720
Lys Ala Pro His Pro Lys Gln Glu Pro Gln Glu Ile Asn Phe Pro Asp
225                 230                 235                 240 gat ctt cct ggc tcc aac act gct gct cca gtg cag gag act tta cat   768
Asp Leu Pro Gly Ser Asn Thr Ala Ala Pro Val Gln Glu Thr Leu His
                245                 250                 255 gga tgc caa ccg gtc acc cag gag gat ggc aaa gag agt cgc atc tca   816
Gly Cys Gln Pro Val Thr Gln Glu Asp Gly Lys Glu Ser Arg Ile Ser
            260                 265                 270 gtg cag gag aga cag tga                                           834
Val Gln Glu Arg Gln *
        275
```

<210> SEQ ID NO 9
<211> LENGTH: 277
<212> TYPE: PRT
<213> ORGANISM: Homo sapiens -continued

```
<400> SEQUENCE: 9

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
        210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
            275
```

TREATMENT OF CANCER OR PRE-MALIGNANT CONDITIONS USING ANTI-CD40 ANTIBODIES

CROSS-REFERENCE TO RELATED APPLICATIONS

This application is a national stage of International Patent Application No. PCT/US2006/042929, filed Nov. 1, 2006, which claims the benefit of U.S. Provisional Application No. 60/732,730, filed Nov. 1, 2005.

This invention relates to new uses of anti-CD40 antibodies, in particular in the treatment of cancers and pre-malignant conditions that are associated with CD40-expressing cells.

BACKGROUND OF THE INVENTION

Many members of the tumor necrosis factor (TNF) family of ligands and their corresponding receptors regulate growth of normal cells by inducing apoptosis or enhancing cell survival and proliferation. It is this balance between apoptotic signals and survival and proliferation signals that maintains normal cellular homeostasis. At least 26 TNF family receptors and 18 TNF family ligands have been identified to date. The biologically active forms of both the receptors and ligands are self-assembled protein trimers. Transmembrane and soluble forms of both the receptors and ligands have been identified. Though the intracellular domains of the receptors share no sequence homology, their extracellular domains comprise 40-amino-acid, cysteine-rich repeats. Their cytoplasmic tails signal by interacting with two major groups of intracellular proteins: TNF receptor-associated factors (TRAFs) and death domain (DD)-containing proteins. Interaction between at least six human TRAFs and TRAF-binding sites on the cytoplasmic tail of some of these receptors initiates several signaling pathways, including AKT (the serine/threonine kinase referred to as protein kinase B or PKB), nuclear factor-κB (NF-κB), and mitogen-activated protein kinases (MAPK). See, for example, the review by Younes and Kadin (2003) *J. Clin. Oncol.* 18:3526-3534.

The TNF family receptor member CD40 is a 50-55 kDa cell-surface antigen present on the surface of both normal and neoplastic human B cells, dendritic cells, monocytes, macrophages, $CD8^+$ T cells, endothelial cells, monocytic and epithelial cells, and many solid tumors, including lung, breast, ovary, urinary bladder, and colon cancers. Binding of the CD40 ligand (CD40L) to the CD40 antigen on the B cell membrane provides a positive costimulatory signal that stimulates B cell activation and proliferation, resulting in B cell maturation into a plasma cell that secretes high levels of soluble immunoglobulin. CD40 activates TRAF-2, -3, -5, and -6, which upregulate diverse signaling pathways following engagement of CD40 with CD40L (either membrane-bound CD40L or soluble CD40L), including extracellular signal-regulated kinase (ERK), c-jun amino terminal kinase (JNK), p38 mitogen-activated protein kinase (MAPK), AKT, and NF-κB (see, for example, Younes and Carbone (1999) *Int. J. Biol. Markers* 14:135-143; van Kooten and Banchereau (2000) *J. Leukoc. Biol.* 67:2-17).

Malignant B cells from tumor types of B-cell lineage express CD40 and appear to depend on CD40 signaling for survival and proliferation. Transformed cells from patients with low- and high-grade B-cell lymphomas, B-cell acute lymphoblastic leukemia, multiple myeloma, chronic lymphocytic leukemia, Walsdenstrom's Macroglobulinemia, and Hodgkin's disease express CD40. CD40 expression is also detected in acute myeloblastic leukemia and 50% of AIDS-related lymphomas.

A number of carcinomas and sarcomas also exhibit high levels of CD40 expression, though the role of CD40 signaling in these cancer cells is less well understood. CD40-expressing carcinomas include urinary bladder carcinoma (Paulie et al. (1989) *J. Immunol.* 142:590-595; Braesch-Andersen et al. (1989) *J. Immunol.* 142:562-567), breast carcinoma (Hirano et al. (1999) *Blood* 93:2999-3007; Wingett et al. (1998) *Breast Cancer Res. Treat.* 50:27-36); prostate cancer (Rokhlin et al. (1997) *Cancer Res.* 57:1758-1768), renal cell carcinoma (Kluth et al. (1997) *Cancer Res.* 57:891-899), undifferentiated nasopharyngeal carcinoma (UNPC) (Agathanggelou et al. (1995) *Am. J. Pathol.* 147:1152-1160), squamous cell carcinoma (SCC) (Amo et al. (2000) *Eur. J. Dermatol.* 10:438-442; Posner et al. (1999) *Clin. Cancer Res.* 5:2261-2270), thyroid papillary carcinoma (Smith et al. (1999) *Thyroid* 9:749-755), cutaneous malignant melanoma (van den Oord et al. (1996) *Am. J. Pathol.* 149:1953-1961), gastric carcinoma (Yamaguchi et al. (2003) *Int. J. Oncol.* 23(6):1697-702), and liver carcinoma (see, for example, Sugimoto et al. (1999) *Hepatology* 30(4):920-26, discussing human hepatocellular carcinoma). For CD40-expressing sarcomas, see, for example, Lollini et al. (1998) *Clin. Cancer Res.* 4(8):1843-849, discussing human osteosarcoma and Ewing's sarcoma.

CD40 signaling protects immature B-cells and B-cell lymphomas from apoptosis induced by IgM or Fas (see, for example, Wang et al. (1995) *J. Immunol.* 155:3722-3725). Mantle cell lymphoma cells express a high level of CD40, and the addition of exogenous CD40 ligand was shown to enhance their survival and rescue them from fludarabine-induced apoptosis (Clodi et al. (1998) *Brit. J. Haematol.* 103:217-219). The role of CD40 signaling in malignant B cell survival and proliferation renders the CD40 antigen a potential target for anti-cancer therapy. Indeed, antagonist anti-CD40 antibodies inhibit proliferation and/or differentiation of malignant human B cells in vitro (see, for example, U.S. Patent Application Publication No. 20040109857). Further, murine models of aggressive human lymphomas have demonstrated the in vivo efficacy of anti-CD40 antibodies in promoting animal survival. See, for example, Funakoshi et al. (1994) *Blood* 83:2787-2794; Tutt et al. (1998) *J. Immunol.* 161:3176-3185; and Szocinski et al. (2002) *Blood* 100: 217-223.

The CD40 ligand (CD40L), also known as CD154, is a 32-33 kDa transmembrane protein that also exists in two smaller biologically active soluble forms, 18 kDa and 31 kDa, respectively (Graf et al. (1995) *Eur. J. Immunol.* 25:1749-1754; Mazzei et al. (1995) *J. Biol. Chem.* 270:7025-7028; Pietravalle et al. (1996) *J. Biol. Chem.* 271:5965-5967). CD40L is expressed on activated, but not resting, $CD4^+$ T-helper cells (Lane et al. (1992) *Eur. J. Immunol.* 22:2573-2578; Spriggs et al. (1992) *J. Exp. Med.* 176:1543-1550; and Roy et al. (1993) *J. Immunol.* 151:1-14). Both CD40 and CD40L have been cloned and characterized (Stamenkovi et al. (1989) *EMBO J.* 8:1403-1410; Armitage et al. (1992) *Nature* 357:80-82; Lederman et al. (1992) *J. Exp. Med.* 175: 1091-1101; and Hollenbaugh et al. (1992) *EMBO J.* 11:4313-4321). See also U.S. Pat. No. 5,945,513, describing human CD40L. Cells transfected with the CD40L gene and expressing the CD40L protein on their surface can trigger B-cell proliferation, and together with other stimulatory signals, can induce antibody production (Armitage et al. (1992) supra; and U.S. Pat. No. 5,945,513). Patients with lymphoid malignancies, autoimmune disease, cardiovascular disease, and essential thrombocythemia have elevated serum levels of soluble CD40L (sCD40L) that are not seen in healthy subjects. Constitutive expression of CD40L has been observed in a subset of patients with several B-cell lymphoid malignancies, including mantle-cell lymphoma, follicular lymphoma, marginal zone lymphoma, chronic lymphocytic leukemia (CLL), diffuse large B-cell lymphoma (DLBCL), follicular lymphoma (FL), and HIV-infected B-cell lymphoma. See, for example, Clodi et al. (1998) *Br. J. Haematol.* 103:270-275; Schattner et al. (1998) *Blood* 91:2689-2697; Moses et al. (1997) *Nat. Med.* 3:1242-1249; Trentin et al. (1997) *Cancer Res.* 57:4940-4947; and Pham et al. (2002) *Immunity* 16:37-50). CD40L may play an important role in the cell contact-dependent interaction of CD40-expressing tumor B-cells within the neoplastic follicles or CD40-expressing Reed-Sternberg cells in Hodgkin's disease areas (Carbone et al. (1995) *Am. J. Pathol.* 147:912-922). However, the mechanism of CD40L-mediated CD40 signaling leading to survival versus cell death responses of malignant B-cells is not completely known. For example, in follicular lymphoma cells, down-regulation of apoptosis-inducing TRAIL molecule (APO-2L) (Ribeiro et al. (1998) *British J. Haematol.* 103: 684-689) and over expression of bcl-2, and in the case of B-CLL, down-regulation of CD95 (Fas/APO-1) (Laytragoon-Lewin et al. (1998) *Eur. J. Haematol.* 61:266-271) have been proposed as mechanisms of survival. In contrast, evidence in follicular lymphoma indicates that CD40 activation leads to up-regulation of TNF (Worm et al. (1994) *International Immunol.* 6:1883-1890) and CD95 molecules (Plumas et al. (1998) *Blood* 91:2875-2885).

Human anti-CD40 monoclonal antibodies and a number of uses thereof are disclosed in co-owned patent applications published as WO 2005/044854, WO 2005/044304, WO 2005/044305, WO 2005/044306, WO 2005/044855, WO 2005/044307, and WO 2005/044294. Those applications specifically disclose a human IgG$_1$ anti-CD40 monoclonal antibody, designated as CHIR-12.12 therein, which was generated by immunization of transgenic mice bearing the human IgG$_1$ heavy chain locus and the human κ light chain locus (XenoMouse® technology; Abgenix, Calif.).

As shown by FACS analysis, CHIR-12.12 binds specifically to human CD40 and can prevent CD40-ligand (CD40L) binding. CHIR-12.12 can compete off CD40L pre-bound to cell surface CD40. The CHIR-12.12 monoclonal antibody is a strong antagonist and inhibits in vitro CD40L-mediated proliferation of normal and malignant B cells. The CHIR-12.12 monoclonal antibody directly inhibits survival and signaling pathways mediated by CD40L in normal human B-lymphocytes. In vitro, CHIR-12.12 kills primary cancer cells from NHL patients by ADCC. Dose-dependent anti-tumor activity was seen in a xenograft human lymphoma model. CHIR-12.12 is currently in Phase I trials for B-cell malignancies.

CD20 is a cell-surface antigen expressed early in B cell differentiation and remains on the cell surface throughout B cell development. CD20 is involved in B cell activation, is expressed at very high levels on neoplastic B cells, and is a clinically recognised therapeutic target (see, for example, Hooijberg et al. (1995) *Cancer Research* 55: 2627). Antibodies targeting CD20, such as rituximab (Rituxan®), have been approved by the U.S. Food and Drug Administration for the treatment of non-Hodgkin's lymphoma (see, for example, Boye et al. (2003) *Ann. Oncol.* 14:520). Rituxan® has been shown to be an effective treatment for low-, intermediate-, and high-grade non-Hodgkin's lymphoma (NHL) and active in other B-cell malignancies (see for example, Maloney et al. (1994) *Blood* 84:2457-2466), McLaughlin et al. (1998) *J. Clin. Oncol.* 16:2825-2833, Maloney et al. (1997) *Blood* 90:2188-2195, Hainsworth et al. (2000) *Blood* 95:3052-3056, Colombat et al. (2001) *Blood* 97:101-106, Coiffer et al. (1998) *Blood* 92:1927-1932), Foran et al. (2000) *J. Clin. Oncol.* 18:317-324, Anderson et al. (1997) *Biochem. Soc. Trans.* 25:705-708, or Vose et al. (1999) *Ann. Oncol.* 10:58a).

Though the exact mechanism of action is not known, evidence indicates that the anti-lymphoma effects of Rituxan® are in part due to complement-mediated cytotoxicity (CMC), antibody-dependent cell-mediated cytotoxicity (ADCC), inhibition of cell proliferation, and finally direct induction of apoptosis. ADCC is a major mechanism of action for many marketed and investigational monoclonal antibodies. Some patients, however, become resistant to treatment with Rituxan® (see Witzig et al. (2002) *J. Clin. Oncol.* 20:3262, Grillo-Lopez et al. (1998) *J. Clin. Oncol.* 16:2825, or Jazirehi et al. (2003) *Mol. Cancer. Ther.* 2:1183-1193). For example, some patients lose CD20 expression on malignant B cells after anti-CD20 antibody therapy (Davis et al. (1999) *Clin. Cancer Res.* 5:611). Furthermore, 30% to 50% of patients with low-grade NHL exhibit no clinical response to this monoclonal antibody (Hainsworth et al. (2000) *Blood* 95:3052-3056; Colombat et al. (2001) *Blood* 97:101-106). The clinical activity of rituximab in NHL has also been shown to be correlated with the patient's FcγRIIIa genotype. Patients with the FcγRIIIa 158aa polymorphism of V/V or V/F are more responsive to rituximab than those with F/F (for example, see Cartron et al. (2002) *Blood* 99(3):754-758 or Dall'Ozzo et al. *Cancer Res.* (2004) 64:4664-4669). For patients developing resistance to this monoclonal antibody, or having a B-cell lymphoma that is resistant to initial therapy with this antibody, alternative forms of therapeutic intervention are needed.

There is thus a continuing need for new therapeutic agents and new therapeutic strategies for cancers and pre-malignant conditions. In particular, there is a need for new therapeutic strategies for treatment of patients who are homozygous or heterozygous for FcγRIIIa-158F and are refractory to treatment with anti-CD20 antibodies, such as rituximab (Rituxan®). Moreover, an antibody that can kill malignant cells without needing a conjugate will result in a drug that is cheaper to make and could have fewer side effects.

BRIEF SUMMARY OF THE INVENTION

Methods for treating a human patient for a cancer or pre-malignant condition that is associated with CD40-expressing cells are provided, where the human patient is heterozygous or homozygous for FcγRIIIa-158F (genotype V/F or F/F). The methods comprise administering to the human patient a therapeutically or prophylactically effective amount of an anti-CD40 antibody. The invention also provides for the use of a therapeutically or prophylactically effective amount of an anti-CD40 antibody in the manufacture of a medicament for the treatment of a cancer or pre-malignant condition that is associated with CD40-expressing cells in a human patient heterozygous or homozygous for FcγRIIIa-158F (genotype V/F or F/F).

Also provided are methods of inhibiting antibody production by B cells in a human patient heterozygous or homozygous for FcγRIIIa-158F (genotype V/F or F/F), comprising administering to the human patient an effective amount of an anti-CD40 antibody. The invention also provides for the use of an effective amount of an anti-CD40 antibody in the manufacture of a medicament for inhibiting antibody production by B cells in a human patient heterozygous or homozygous for FcγRIIIa-158F (V/F or F/F).

Methods and kits for identifying a human patient with a cancer or pre-malignant condition that is treatable with an anti-CD40 antibody and which is refractory to treatment with rituximab (Rituxan®) are also provided. In some embodiments, the methods comprise: a) identifying a human patient with a cancer or pre-malignant condition that is associated with CD40-expressing cells and which is refractory to treatment with rituximab (Rituxan®); and b) determining the human patient's FcγRIIIa-158 genotype (V/V, V/F or F/F); wherein the cancer or pre-malignant condition is treatable with an anti-CD40 antibody if the human patient is heterozygous or homozygous for FcγRIIIa-158F (genotype V/F or F/F). The invention may further include the step of administering to a human patient identified using this method a therapeutically or prophylactically effective amount of an anti-CD40 antibody. Kits of the present invention that provide for identification of a human patient with a cancer or pre-malignant condition that is treatable with an anti-CD40 antibody comprise reagents for determining a human patient's FcγRIIIa-158 genotype.

The invention also provides methods and kits for selecting an antibody therapy for treatment of a human patient having a cancer or pre-malignant condition that is refractory to treatment with rituximab (Rituxan®). In some embodiments, the methods comprise: a) identifying a human patient having a cancer or pre-malignant condition that is associated with CD40-expressing cells and which is refractory to treatment with rituximab (Rituxan®); and b) determining the human patient's FcγRIIIa-158 genotype (V/V, V/F or F/F); wherein if the human patient is heterozygous or homozygous for FcγRIIIa-158F (genotype V/F or F/F), an anti-CD40 antibody is selected for treatment of the cancer or pre-malignant condition. The invention may further include the step of administering to a human patient identified using this method a therapeutically or prophylactically effective amount of an anti-CD40 antibody. Kits of the present invention that provide for selecting an antibody therapy for treatment of a human patient having a cancer or pre-malignant condition associated with CD40-expressing cells comprise reagents for determining a human patient's FcγRIIIa-158 genotype.

The present invention also provides methods for treating a human patient for a cancer or pre-malignant condition that is associated with CD40-expressing cells, where the methods comprise administering to the human patient a slow-internalizing antibody. In one such embodiment, a therapeutically or prophylactically effective amount of an anti-CD40 antibody is administered to the human patient such that the anti-CD40 antibody is not significantly internalized by CD40-expressing cells following its administration. In another such embodiment, a therapeutically or prophylactically effective amount of an anti-CD40 antibody is administered to the human patient such that the anti-CD40 antibody remains substantially uniformly distributed on the surface of CD40-expressing cells following its administration. In yet another such embodiment, an anti-CD40 antibody is administered to the human patient such that a therapeutically or prophylactically effective amount of the anti-CD40 antibody is present at the surface of CD40-expressing cells in the human patient following its administration.

Anti-CD40 antibodies for use in accordance with the present invention specifically bind the CD40 antigen. In some embodiments, anti-CD40 antibodies for use in the methods of the present invention, in particular monoclonal antibodies, exhibit a strong binding affinity for human FcγRIIIa-158V, a strong binding affinity for human FcγRIIIa-158F, or a strong binding affinity for both human FcγRIIIa-158V and FcγRIIIa-158F. In some of these embodiments, the anti-CD40 antibodies can bind to either of the two FcγRIIIa amino acid 158 allotypes (V or F) on a human patient's natural killer (NK) cells with binding characteristics that are adequate to cause potent antibody-dependent cellular cytotoxicity (ADCC). Suitable anti-CD40 antibodies include, but are not limited to, anti-CD40 antibodies that are free of significant agonist activity, including, for example, anti-CD40 antibodies that are an antagonist of CD40-CD40L signaling on CD40-expressing cells. In some embodiments, the anti-CD40 antibody is selected from the group consisting of: a) the monoclonal antibody CHIR-12.12; b) the monoclonal antibody produced by the hybridoma cell line 12.12; c) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; d) a monoclonal antibody having an amino acid sequence encoded by a nucleic acid molecule comprising a nucleotide sequence selected from the group consisting of the sequence shown in SEQ ID NO: 1, the sequence shown in SEQ ID NO:3, and both the sequences shown in SEQ ID NO: 1 and SEQ ID NO:3; e) a monoclonal antibody that binds to an epitope capable of binding the monoclonal antibody produced by the hybridoma cell line 12.12; f) a monoclonal antibody that binds to an epitope comprising residues 82-87 of the human CD40 sequence shown in SEQ ID NO:7 or SEQ ID NO:9; g) a monoclonal antibody that binds to an epitope comprising residues 82-89 of the human CD40 sequence shown in SEQ ID NO:7 or SEQ ID NO:9; h) a monoclonal antibody that competes with the monoclonal antibody CHIR-12.12 in a competitive binding assay; i) the monoclonal antibody of preceding item a) or a monoclonal antibody of any one of preceding items c)-h), wherein the antibody is recombinantly produced; and j) a monoclonal antibody that is an antigen-binding fragment of a monoclonal antibody of any one of preceding items a)-i), wherein the fragment retains the capability of specifically binding to human CD40 antigen.

The methods of the present invention find use in treatment of cancers and pre-malignant conditions that are associated with CD40-expressing cells. Examples include, but are not limited to, cancers of B-cell lineage, non-B cell haematological malignancies, for example, acute myelocytic leukaemia, solid tumors, and cancers or pre-malignant conditions associated with CD20-expressing cells. The methods of the invention are particularly advantageous with respect to cancers and pre-malignant conditions that are associated with cells expressing both CD40 and CD20. In this manner, the present invention enables the treatment of patients having a cancer or pre-malignant condition that is refractory to therapy with other oncotherapeutic agents, including anti-CD20 antibodies for patients who are homozygous or heterozygous for the FcγRIIIa-158F (genotype V/F or F/F).

BRIEF DESCRIPTION OF THE DRAWINGS

FIG. 2A-2D show results of an analysis of antibody-dependent cellular cytotoxicity (ADCC) in CLL patient cells (n=8).

FIG. 3 summarizes results of an analysis of ADCC in CLL patient cells (n=9).

FIG. 4 shows results of an analysis of ADCC in CLL patient cells, using NK effector cells from two different donors.

FIG. 5 shows results of quantitation of CD40 and CD20 cell-surface expression on CLL patient cells and normal B cells.

FIG. 6 summarizes ADCC activity for cells with quantitated CD40 and CD20 cell-surface expression.

FIG. 7 is a bar chart showing levels of cell-surface bound CHIR-12.12 on Daudi and ARH77 cell lines.

FIG. 8 shows results of investigation of internalization of CHIR-12.12 and rituximab in CLL patient cells by FACS analysis.

FIG. 9 shows results of investigation of internalization of CHIR-12.12 and rituximab in normal B cells by confocal microscopy of FITC-labelled antibodies.

FIG. 10 shows results of investigation of internalization of CHIR-12.12 and rituximab in CLL patient cells by confocal microscopy of Alexa488-labelled antibodies.

FIG. 11 summarizes the relationship between ADCC activity and internalization.

FIG. 14 summarizes comparative ADCC of CHIR-12.12 and rituximab against CLL patient cells (n=9) by human NK cells from multiple genotyped human donors.

DETAILED DESCRIPTION OF THE INVENTION

Figure 1A:
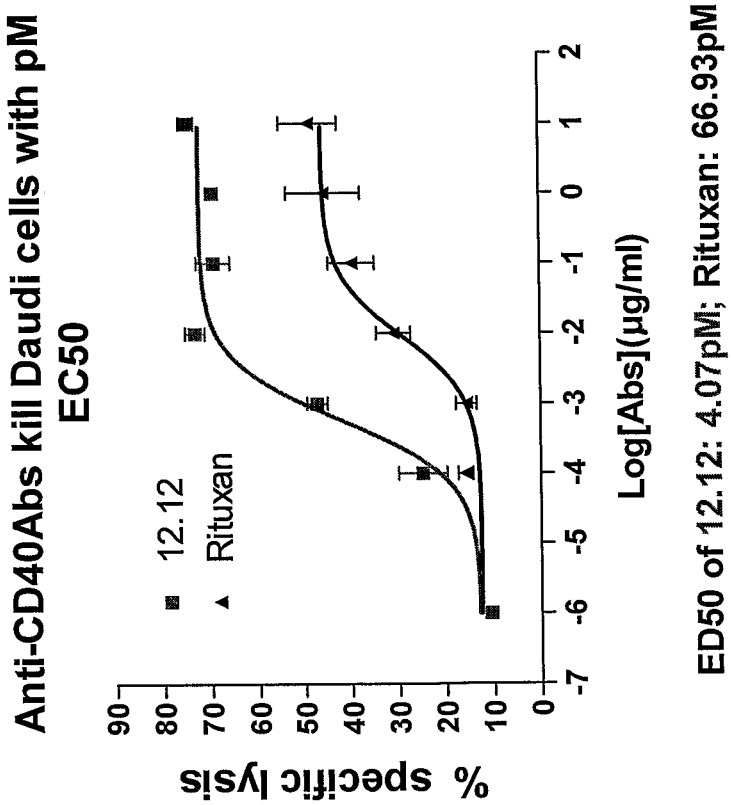
FIG. 1A-1F show results of an analysis of antibody-dependent cellular cytotoxicity (ADCC) in six cell lines.
Figure 1B:
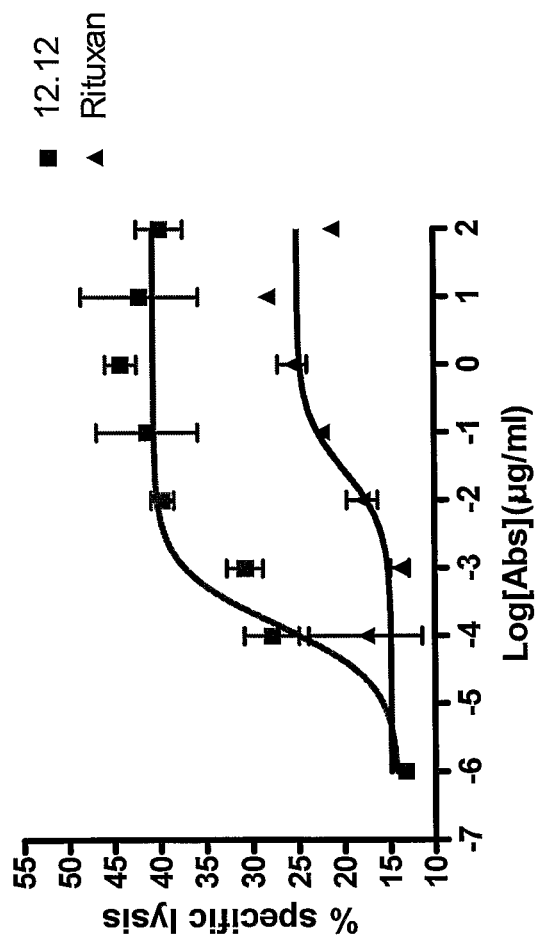
Figure 1C:
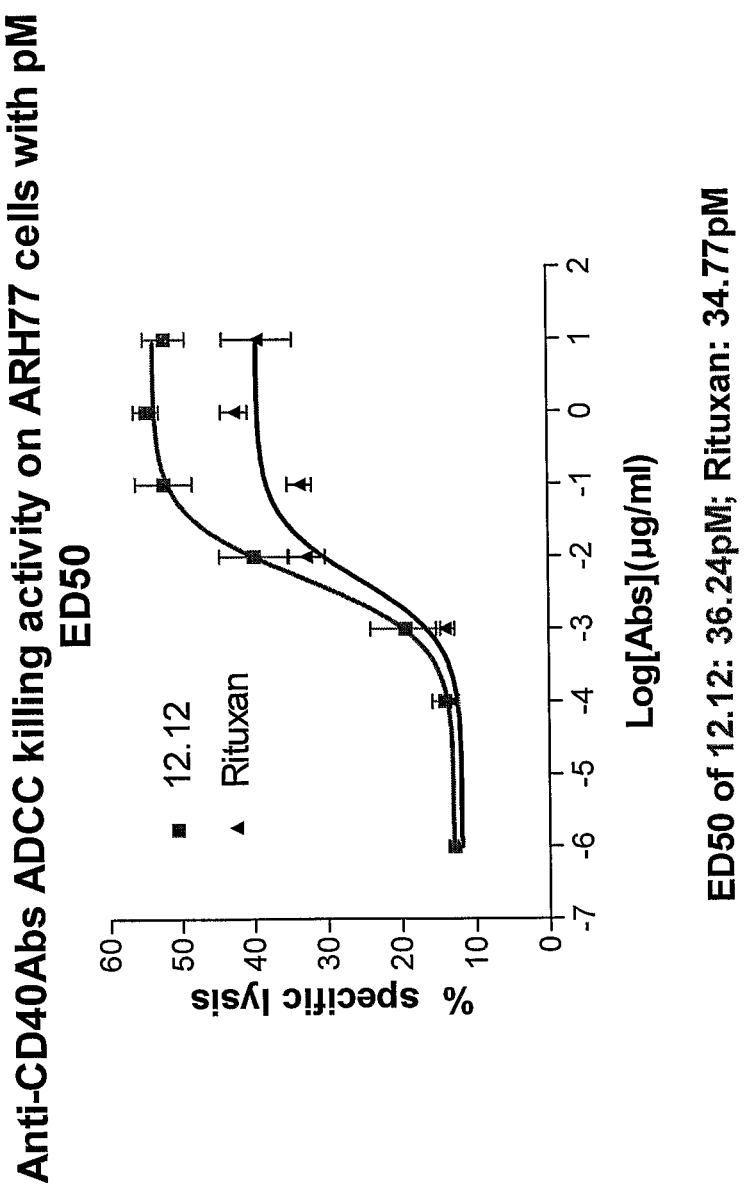
Figure 1D:
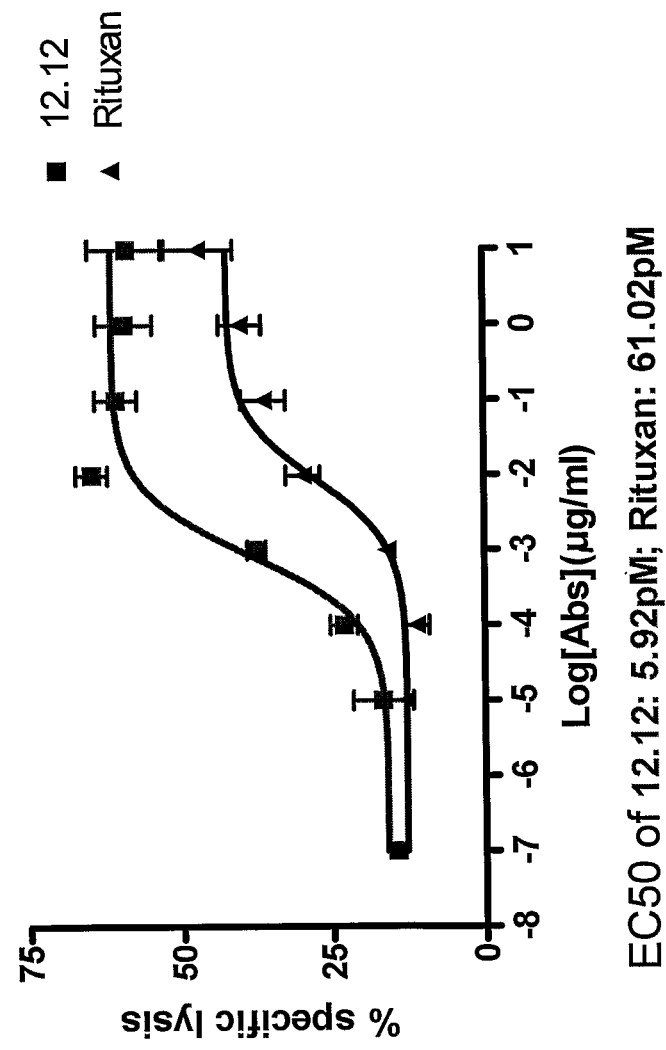
Figure 1E:
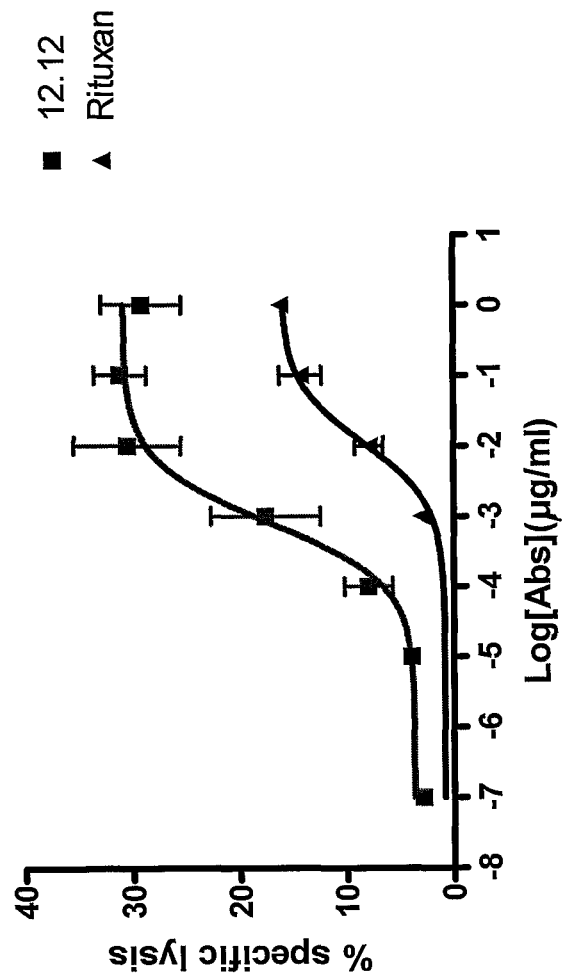
Figure 1F:
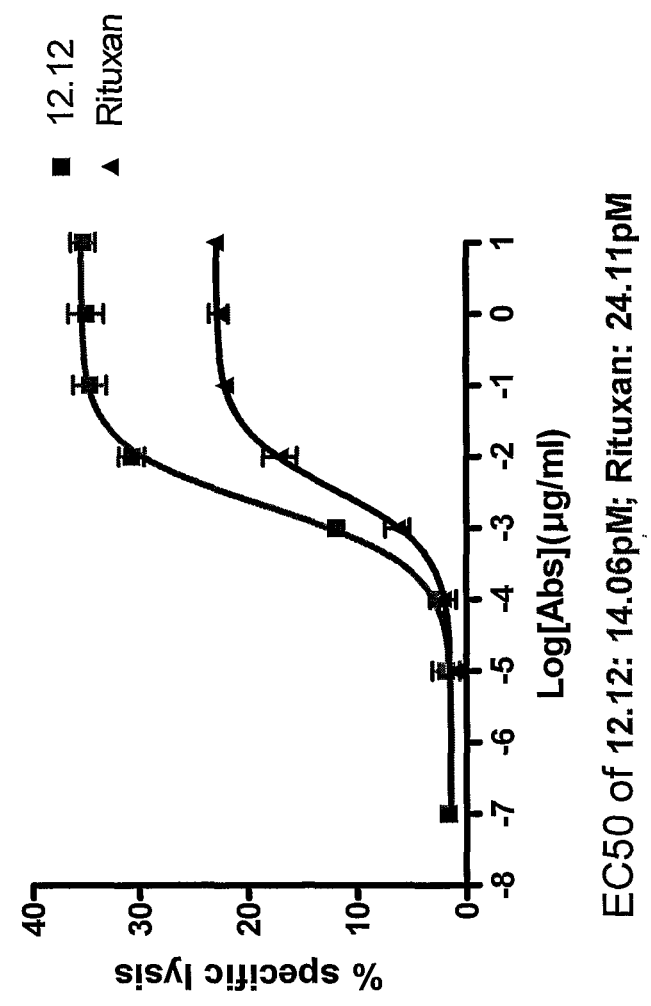

The inventors have made the surprising finding that anti-CD40 antibodies, such as CHIR-12.12, are able to mediate potent antibody-dependent cellular cytotoxicity (ADCC) of CD40-expressing target cells under conditions where other ADCC mediating antibodies are less effective or relatively ineffective. Contrary to other antibodies, such as rituximab (Rituxan®), anti-CD40 antibodies used according to the invention can bind to either of the two FcγRIIIa amino acid 158 allotypes (V or F) on a human patient's natural killer (NK) cells with binding characteristics that are adequate to cause potent ADCC. This finding is unexpected and represents an advance in our ability to treat cancers and pre-malignant conditions across an entire patient cross-section.

Accordingly, anti-CD40 antibodies, such as CHIR-12.12, can be used in the treatment of cancers and pre-malignant conditions associated with CD40-expressing cells in human patients heterozygous or homozygous for FcγRIIIa-158F (genotype V/F or F/F), in addition to human patients homozygous for FcγRIIIa-158V (genotype V/V).

The invention thus provides a method for treating a human patient for a cancer or pre-malignant condition that is associated with CD40-expressing cells, wherein said human patient is heterozygous or homozygous for FcγRIIIa-158F (genotype V/F or F/F), the method comprising administering to said human patient a therapeutically or prophylactically effective amount of an anti-CD40 antibody. The invention also provides the use of a therapeutically or prophylactically effective amount of an anti-CD40 antibody in the manufacture of a medicament for the treatment of a cancer or pre-malignant condition that is associated with CD40-expressing cells in a human patient heterozygous or homozygous for FcγRIIIa-158F (genotype V/F or F/F).

As noted above, the clinical activity of rituximab in NHL has been shown to be correlated with the patient's FcγRIIIa genotype. Patients with the FcγRIIIa 158aa polymorphism of F/F are less responsive to rituximab than those with V/V or V/F (for example, see Cartron et al. (2002) *Blood* 99(3): 754-758 or Dall'Ozzo et al. (2004) *Cancer Res.* 64:4664-4669). Accordingly, the present invention is especially advantageous for the treatment of cancers and pre-malignant conditions that are not responsive to treatment with an anti-CD20 antibody such as rituximab (Rituxan®).

Anti-CD40 antibodies, such as CHIR-12.12, can be used in methods for inhibiting antibody production by B cells in a human patient heterozygous or homozygous for FcγRIIIa-158F (genotype V/F or F/F), in addition to human patients homozygous for FcγRIIIa-158V (genotype V/V).

Thus, the invention provides a method of inhibiting antibody production by B cells in a human patient heterozygous or homozygous for FcγRIIIa-158F (genotype V/F or F/F), comprising administering to said human patient an effective amount of an anti-CD40 antibody, such as CHIR-12.12. The invention also provides the use of an effective amount of an anti-CD40 antibody in the manufacture of a medicament for inhibiting antibody production by B cells in a human patient heterozygous or homozygous for FcγRIIIa-158F (V/F or F/F).

It would not have been expected by a person skilled in the art that one could inhibit antibody production by B cells in a human patient heterozygous or homozygous for FcγRIIIa-158F (genotype V/F or F/F).

The present invention allows the treatment regimen selected for an individual human patient to be based on that patient's FcγRIIIa-158 genotype by administering an ADCC-mediating anti-CD40 antibody.

The invention provides a method for identifying a human patient with a cancer or pre-malignant condition treatable with an anti-CD40 antibody and which is refractory to treatment with rituximab (Rituxan®), comprising:

a) identifying a human patient with a cancer or pre-malignant condition that is associated with CD40-expressing cells and which is refractory to treatment with rituximab (Rituxan®); and b) determining said human patient's FcγRIIIa-158 genotype (V/V, V/F or F/F);

wherein said cancer or pre-malignant condition is treatable with an anti-CD40 antibody if said human patient is heterozygous or homozygous for FcγRIIIa-158F (genotype V/F or F/F). The invention may further include the step of administering to a human patient identified using this method a therapeutically or prophylactically effective amount of an anti-CD40 antibody.

This method of identifying a human patient with a cancer or pre-malignant condition treatable with an anti-CD40 antibody can readily be performed by a person skilled in the art using a suitable diagnostic kit. The kit should comprise reagents suitable for determining a human patient's FcγRIIIa-158 genotype. Thus, the invention also provides a kit for identifying a human patient with a cancer or pre-malignant condition treatable with an anti-CD40 antibody, comprising reagents for determining a human patient's FcγRIIIa-158 genotype. Suitable kits are described in more detail elsewhere herein.

The invention also provides a method for selecting an antibody therapy for treatment of a human patient having a cancer or pre-malignant condition which is refractory to treatment with rituximab (Rituxan®), comprising:

a) identifying a human patient having a cancer or pre-malignant condition that is associated with CD40-expressing cells and which is refractory to treatment with rituximab (Rituxan®); and b) determining said human patient's FcγRIIIa-158 genotype (V/V, V/F or F/F);

wherein if said human patient is heterozygous or homozygous for FcγRIIIa-158F (genotype V/F or F/F), an anti-CD40 antibody is selected for treatment of said cancer or pre-malignant condition. In particular, an anti-CD40 antibody may be selected in preference to treatment with rituximab (Rituxan®). The invention may further include the step of administering to a human patient identified using this method a therapeutically or prophylactically effective amount of an anti-CD40 antibody.

This method of selecting an antibody therapy for treatment of a human patient having a cancer or pre-malignant condition can readily be performed by a person skilled in the art using a suitable diagnostic kit. The kit should comprise reagents suitable for determining a human patient's FcγRIIIa-158 genotype. Thus, the invention also provides a kit for selecting an antibody therapy for treatment of a human patient having a cancer or pre-malignant condition associated with CD40-expressing cells, comprising reagents for determining a human patient's FcγRIIIa-158 genotype.

The inventors have also made the surprising finding that anti-CD40 antibodies, such as CHIR-12.12, are not significantly internalized by CD40-expressing cells following administration. Instead, anti-CD40 antibodies, such as CHIR-12.12, are substantially uniformly distributed on the surface of CD40-expressing cells for a significant period of time following administration. This is in contrast to other antibodies, in particular anti-CD20 antibodies, such as rituximab (Rituxan®).

The duration of CD40 binding at the surface of CD40-expressing cells and the uniform distribution of the anti-CD40 antibody on the surface of CD40-expressing cells enables the anti-CD40 antibodies to mediate potent antibody-dependent cellular cytotoxicity (ADCC) of CD40-expressing target cells, via binding to an FcR, such as the FcγRIIIa on natural killer (NK) cells.

Thus, the invention provides a method for treating a human patient for a cancer or pre-malignant condition that is associated with CD40-expressing cells, the method comprising administering to said human patient a therapeutically or prophylactically effective amount of an anti-CD40 antibody, such that the anti-CD40 antibody is not significantly internalized by CD40-expressing cells following administration.

The invention also provides a method for treating a human patient for a cancer or pre-malignant condition that is associated with CD40-expressing cells, the method comprising administering to said human patient a therapeutically or prophylactically effective amount of an anti-CD40 antibody, such that the anti-CD40 antibody remains substantially uniformly distributed on the surface of CD40-expressing cells following administration.

The invention also provides a method for treating a human patient for a cancer or pre-malignant condition that is associated with CD40-expressing cells, the method comprising administering to said human patient an anti-CD40 antibody, such that a therapeutically or prophylactically effective amount of the anti-CD40 antibody is present at the surface of CD40-expressing cells in said human patient following administration.

These aspects of the invention thus involve administering to a patient a slow-internalizing antibody. By "slow-internalizing antibody" is intended an antibody that remains disposed on the cell surface for a significant period of time. As the skilled person will be aware, this property contrasts with properties deemed advantageous for many therapeutic applications that actually require internalization of antibody-receptor complex in order for the therapy to be efficacious. In this context, a significant period of time generally exceeds 3 hours, preferably 6 hours, more preferably 12 hours, more preferably 24 hours, 36 hours, 48 hours, 72 hours, 96 hours, 120 hours, 144 hours, 168 hours or more.

Preferably, at least 5%, at least 10%, at least 20%, at least 30%, at least 40%, at least 50%, at least 60%, at least 70%, at least 80%, at least 90%, or more of the antibody initially disposed on the surface of a CD40-expressing cell remains disposed on the surface of the cell after the above significant period of time.

Internalization of antibodies can be assessed by various assays. For example, cell lines such as the Daudi lymphoma cell line, or ARH77 mM cell line, can be used to evaluate the effect of a candidate antibody binding on internalization. Cells are incubated with human IgG1 (control antibody) or the candidate antibody on ice (with 0.1% sodium azide to block internalization) or 37° C. (without sodium azide) for a period of time, suitably 3 hours. After a wash with cold staining buffer (e.g. PBS+1% BSA+0.1% sodium azide), cells are stained, for example with goat anti-human IgG-FITC for 30 minutes on ice. The degree of staining can then be assessed; in this example, geometric mean fluorescent intensity (MFI) could be recorded, such as by FACS Calibur. Other suitable assays will be known to those of skill in the art (see, for example http://www.abgenix.com/documents/SBS2003%20poster.pdf).

In experiments set out in Examples 4 and 5 herein, no difference in MFI was observed between cells incubated with CH12.12 on ice in the presence of sodium azide or at 37° C. in the absence of sodium azide (see FIGS. 7-10). These data show that CH12.12, upon binding to CD40, is not internalized and continues to be displayed on the cell surface for a longer time than rituximab.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook et al. (1989) *Molecular Cloning, A Laboratory Manual* (2d ed.); D. N Glover, ed. (1985) *DNA Cloning*, Volumes I and II; M. J. Gait, ed. (1984) *Oligonucleotide Synthesis*; B. D. Hames & S. J. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); B. Perbal (1984) *A Practical Guide to Molecular Cloning; the Methods in Enzymology* series (Academic Press, Inc.), especially volumes 154 & 155; J. H. Miller and M. P. Calos, eds. (1987) *Gene Transfer Vectors for Mammalian Cells* (Cold Spring Harbor Laboratory); Mayer and Walker, eds. (1987) *Immunochemical Methods in Cell and Molecular Biology* (Academic Press, London); Scopes (1987) *Protein Purification: Principles and*

*Practice* (2d ed.; Springer Verlag, N.Y.); and D. M. Weir and C. C. Blackwell, eds. (1986) *Handbook of Experimental Immunology*, Volumes I-IV.

The methods of the invention involve the use of anti-CD40 antibodies in the treatment of cancers and pre-malignant conditions associated with CD40-expressing cells.

By "CD40", "CD40 antigen", or "CD40 receptor" is intended the 50-55 kDa transmembrane glycoprotein of the tumor necrosis factor (TNF) receptor family (see, for example, U.S. Pat. Nos. 5,674,492 and 4,708,871; Stamenkovic et al. (1989) *EMBO* 8:1403; Clark (1990) *Tissue Antigens* 36:33; Barclay et al. (1997) *The Leucocyte Antigen Facts Book* (2d ed.; Academic Press, San Diego)). Two isoforms of human CD40, encoded by alternatively spliced transcript variants of this gene, have been identified. The first isoform (also known as the "long isoforms" or "isoform 1") is expressed as a 277-amino-acid precursor polypeptide (SEQ ID NO:9; first reported as GenBank Accession No. CAA43045, and identified as isoform 1 in GenBank Accession No. NP_001241), encoded by SEQ ID NO:8 (see GenBank Accession Nos. X60592 and NM_001250), which has a signal sequence represented by the first 19 residues. The second isoform (also known as the "short isoforms" or "isoform 2") is expressed as a 203-amino-acid precursor polypeptide (SEQ ID NO:7; GenBank Accession No. NP_690593), encoded by SEQ ID NO:6 (GenBank Accession No. NM_152854), which also has a signal sequence represented by the first 19 residues. The precursor polypeptides of these two isoforms of human CD40 share in common their first 165 residues (i.e., residues 1-165 of SEQ ID NO:7 and SEQ ID NO:9). The precursor polypeptide of the short isoform (shown in SEQ ID NO:7) is encoded by a transcript variant (SEQ ID NO:6) that lacks a coding segment, which leads to a translation frame shift; the resulting CD40 isoform contains a shorter and distinct C-terminus (residues 166-203 of SEQ ID NO:7) from that contained in the long isoform of CD40 (C-terminus shown in residues 166-277 of SEQ ID NO:9). For purposes of the present invention, the term "CD40," or "CD40 antigen," "CD40 cell surface antigen," or "CD40 receptor" encompasses both the short and long isoforms of CD40. The CD40 antigen may be fully or partially glycosylated.

As noted elsewhere herein, CD40 is found on the surface of both normal and neoplastic human B cells, dendritic cells, monocytes, macrophages, CD8$^+$ T cells, endothelial cells, monocytic and epithelial cells, and many solid tumors, including lung, breast, ovary, urinary bladder, and colon cancers. Malignant B cells from tumor types of B-cell lineage express CD40 and appear to depend on CD40 signaling for survival and proliferation. Transformed cells from patients with low- and high-grade B-cell lymphomas, B-cell acute lymphoblastic leukemia, multiple myeloma, chronic lymphocytic leukemia, Walsdenstrom's Macroglobulinemia, and Hodgkin's disease express CD40. CD40 expression is also detected in acute myeloblastic leukemia and 50% of AIDS-related lymphomas. A number of carcinomas and sarcomas also exhibit high levels of CD40 expression, though the role of CD40 signaling in relation to CD40 expression on these cancer cells is less well understood. CD40-expressing carcinomas include urinary bladder carcinoma, breast carcinoma, prostate cancer, renal cell carcinoma, undifferentiated nasopharyngeal carcinoma (UNPC), squamous cell carcinoma (SCC), thyroid papillary carcinoma, cutaneous malignant melanoma, gastric carcinoma, and liver carcinoma.

By "CD40-expressing cells" herein is intended any normal or malignant cells that express detectable levels of the CD40 antigen. Preferably, the CD40-expressing cells are cells that express detectable levels of cell-surface CD40 antigen. Methods for detecting CD40 expression in cells are well known in the art and include, but are not limited to, PCR techniques, immunohistochemistry, flow cytometry, Western blot, ELISA, and the like. These methods allow for the detection of CD40 mRNA, CD40 antigen and cell-surface CD40 antigen. Detection of cell-surface CD40 expression can be performed as described in Example 3 herein, or by other suitable methods.

The malignant cell may be a malignant B cell. By "malignant B cell" is intended any neoplastic B cell, including but not limited to B cells derived from lymphomas including low-, intermediate-, and high-grade B cell lymphomas, immunoblastic lymphomas, non-Hodgkin's lymphomas, Hodgkin's disease, Epstein-Barr Virus (EBV) induced lymphomas, and AIDS-related lymphomas, as well as B cell acute lymphoblastic leukemias, myelomas, chronic lymphocytic leukemias, and the like.

By "CD40 ligand" or "CD40L" is intended primarily the 32-33 kDa transmembrane protein that also exists in two smaller biologically active soluble forms, 18 kDa and 31 kDa, respectively (Graf et al. (1995) *Eur. J. Immunol.* 25:1749-1754; Mazzei et al. (1995) *J. Biol. Chem.* 270:7025-7028; Pietravalle et al. (1996) *J. Biol. Chem.* 271:5965-5967). Human CD40L is also known as CD154 or gp39. By "CD40 ligand" or "CD40L" is also intended to any other peptide, polypeptide, or protein that can bind to and activate one or more CD40 signaling pathways. Thus, "CD40 ligands" include, but are not limited to, full-length CD40 ligand proteins and variants and fragments thereof that retain sufficient activity to carry out the function of binding to and stimulating CD40 signaling on CD40-expressing cells. Modifications to a native CD40 ligand, for example, human CD40L, include, but are not limited to, substitutions, deletions, truncations, extensions, fusion proteins, fragments, peptidomimetics, and the like.

By "CD40 signaling" is intended any of the biological activities that result from interaction of cell-surface CD40 with a CD40 ligand or other agonist, such as an agonist antibody. Examples of CD40 signaling are signals that lead to proliferation and survival of CD40-expressing cells, and stimulation of one or more CD40-signaling pathways within CD40-expressing cells. A CD40 "signaling pathway" or "signal transduction pathway" is intended to mean at least one biochemical reaction, or a group of biochemical reactions, that results from interaction of the CD40 receptor with a CD40 ligand, for example, CD40L, and which generates a signal that, when transmitted through the signal pathway, leads to activation of one or more downstream molecules in the signaling cascade. Signal transduction pathways involve a number of signal transduction molecules that lead to transmission of a signal from the cell-surface CD40 receptor across the plasma membrane of a cell, and through one or more in a series of signal transduction molecules, through the cytoplasm of the cell, and in some instances, into the cell's nucleus. Of particular interest to the present invention are CD40 signal transduction pathways, including the AKT signaling pathway, which leads to activation of AKT, and ultimately activation of NF-κB via the NF-κB signaling pathway; and mitogen-activated protein kinase (MAPK) signaling pathways, including the MEK/ERK signaling pathway and the MEK/p38 signaling pathway, which lead to activation of ERK and p38, respectively.

As noted above, the present invention provides a method for treating a human patient for a cancer or pre-malignant condition that is associated with CD40-expressing cells, wherein said human patient is heterozygous or homozygous for FcγRIIIa-158F (genotype V/F or F/F), the method comprising administering to said human patient a therapeutically or prophylactically effective amount of an anti-CD40 antibody.

By "human patient" is intended a human patient who is afflicted with, at risk of developing or relapsing with, any cancer or pre-malignant condition that is associated with CD40-expressing cells.

By "cancer or pre-malignant condition associated with CD40-expressing cells" is intended any of the cancers of B-cell lineage, non-B cell hematological malignancies, and solid tumors that are known to be associated with CD40-expressing cells.

The methods of the invention are useful in the therapeutic treatment of cancers of B-cell lineage. Cancers of B-cell lineage that are associated with CD40-expressing cells include, but are not limited to, acute lymphoblastic leukemia (ALL), chronic lymphocytic leukemia (CLL), prolymphocytic leukemia (PLL), small lymphocytic leukemia (SLL), hairy cell leukemia, Hodgkin's disease, multiple myeloma, Waldenstrom's macroglobulinemia, heavy chain disease, and the lymphomas, including, but not limited to, diffuse small lymphocytic lymphoma, follicular, DLBCL, mucosal associated lymphoid tissue lymphoma, monocytoid B cell lymphoma, splenic lymphoma, lymphomatoid granulomatosis, intravascular lymphomatosis, immunoblastic lymphoma, AIDS-related lymphoma, and the like.

Thus, the methods of the invention find use in the treatment of subjects having non-Hodgkin's lymphomas related to abnormal, uncontrollable B cell proliferation or accumulation. For purposes of the present invention, such lymphomas will be referred to according to the Working Formulation classification scheme, that is those B cell lymphomas categorized as low grade, intermediate grade, and high grade (see "The Non-Hodgkin's Lymphoma Pathologic Classification Project," *Cancer* 49 (1982):2112-2135). Thus, low-grade B cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

The methods of the invention are useful in the therapeutic treatment of B cell lymphomas that are classified according to the Revised European and American Lymphoma Classification (REAL) system. Such B cell lymphomas include, but are not limited to, lymphomas classified as precursor B cell neoplasms, such as B lymphoblastic leukemia/lymphoma; peripheral B cell neoplasms, including B cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B cell lymphoma (including extranodal, nodal, and splenic types), plasmacytoma/myeloma, diffuse large cell B cell lymphoma of the subtype primary mediastinal (thymic), Burkitt's lymphoma, and Burkitt's like high-grade B cell lymphoma; and unclassifiable low-grade or high-grade B cell lymphomas.

The methods of the invention are useful in the therapeutic treatment of the pre-malignant condition known as MGUS (monoclonal gammopathy of undetermined significance). Approximately 25% of patients with MGUS eventually develop multiple myeloma (MM) or a related plasma cell disorder (Kyle (1993) *Mayo Clinic. Proc.* 68:26-36). Proliferation of malignant plasma cells in the bone marrow, detection of a serum or urine monoclonal protein (M protein), anemia, hypercalcemia, renal insufficiency, and lytic bone lesions are clinical manifestations of MM, while MGUS is clinically recognized as the presence of M protein in the serum or urine without other clinical features of MM (see, for example, Kyle and Lust (1989) *Semin. Hematol.* 26:176-200; Greipp and Lust Stem Cells (1995) 13:10-21). MGUS patients are asymptomatic and have stable measurements of M protein (Kyle (1993) *Mayo Clinic. Proc.* 68:26-36). Once MGUS is identified in a subject, maintenance therapy with an appropriate anti-CD40 antibody, for example, an antagonist anti-CD40 antibody, may block the development of multiple myeloma in these patients.

The methods of the present invention are also useful for therapeutic treatment of non-B cell related hematological malignancies associated with CD40-expressing cells, such as acute myelocytic leukemias, and the like.

The methods of the present invention are also useful for therapeutic treatment of solid tumors. Solid tumors that are associated with CD40-expressing cells include, but are not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), skin cancers such as melanoma, and sarcomas, including, for example, osteosarcomas and Ewing's sarcomas.

The cancer or pre-malignant condition associated with CD40-expressing cells may be a cancer or pre-malignant condition associated with an undesirable level of CD40 signaling on CD40-expressing cells, or the cancer or pre-malignant condition might be only indirectly associated with CD40-expressing cells. By "a cancer or pre-malignant condition associated with an undesirable level of CD40 signaling" is intended a cancer or pre-malignant condition whose development or progression is associated with an undesirable level of CD40 signaling.

By "an undesirable level of CD40 signaling" is intended any physiologically undesirable level of CD40 signaling that might occur in CD40-expressing cells in a human patient having a cancer or pre-malignant condition.

The cancer or pre-malignant condition may be a cancer or pre-malignant condition associated with CD20-expressing cells. Such cancers or pre-malignant conditions include, but are not limited to, the B cell malignancies mentioned elsewhere herein.

The present invention is particularly advantageous in respect of cancers and pre-malignant conditions that are associated with cells expressing both CD40 and CD20, because the new uses of anti-CD40 antibodies, such as CHIR-12.12, disclosed herein address problems associated with the use of anti-CD20 antibodies, such as Rituxan®. In particular, the present invention enables the treatment of patients having a cancer or pre-malignant condition that is refractory to therapy with other oncotherapeutic agents, including anti-CD20 antibodies, such as Rituxan® for patients who are homozygous or heterozygous for the FcγRIIIa-158F (genotype V/F or F/F), as described in more detail elsewhere herein.

In the therapeutic methods of the present invention, at least one anti-CD40 antibody as defined elsewhere herein is used to promote a positive therapeutic response with respect to a cancer or pre-malignant condition.

By "positive therapeutic response" with respect to a cancer or pre-malignant condition is intended an improvement in the cancer or pre-malignant condition in association with the therapeutic activity of the anti-CD40 antibody, and/or an improvement in the symptoms associated with the cancer or pre-malignant condition. That is, an anti-proliferative effect, the prevention of further tumor outgrowths, a reduction in tumor size, a reduction in the number of cancer cells, and/or a decrease in one or more symptoms associated with CD40-expressing cells can be observed. Thus, for example, a positive therapeutic response would refer to one or more of the following improvements in the disease: (1) a reduction in tumor size; (2) a reduction in the number of cancer (i.e., neoplastic) cells; (3) an increase in neoplastic cell death; (4) inhibition of neoplastic cell survival; (4) inhibition (i.e., slowing to some extent, preferably halting) of tumor growth; (5) inhibition (i.e., slowing to some extent, preferably halting) of cancer cell infiltration into peripheral organs; (6) inhibition (i.e., slowing to some extent, preferably halting) of tumor metastasis; (7) the prevention of further tumor outgrowths; (8) an increased patient survival rate; and (9) some extent of relief from one or more symptoms associated with the cancer.

Positive therapeutic responses in any given malignancy can be determined by standardized response criteria specific to that malignancy. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation. In addition to these positive therapeutic responses, the subject undergoing therapy with the anti-CD40 therapeutic agent may experience the beneficial effect of an improvement in the symptoms associated with the disease. Thus for B cell tumors, the subject may experience a decrease in the so-called B symptoms, i.e., night sweats, fever, weight loss, and/or urticaria. For pre-malignant conditions, therapy with an anti-CD40 therapeutic agent may block and/or prolong the time before development of a related malignant condition, for example, development of multiple myeloma in subjects suffering from monoclonal gammopathy of undetermined significance (MGUS).

An improvement in the disease may be characterized as a complete response. By "complete response" is intended an absence of clinically detectable disease with normalisation of any previously abnormal radiographic studies, bone marrow, and cerebrospinal fluid (CSF) or abnormal monoclonal protein in the case of myeloma. Such a response must persist for at least 4 to 8 weeks, or in disease specific, sometimes 6 to 8 weeks, following treatment according to the methods of the invention. Alternatively, an improvement in the disease may be categorised as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions and persisting for 4 to 8 weeks as required. In myeloma, normal response (25-50% decrease in myeloma protein in urine) is also considered a response. Such a response is applicable to measurable tumors only.

By "therapeutically or prophylactically effective dose" or "therapeutically or prophylactically effective amount" is intended an amount of anti-CD40 antibody that, when administered brings about a positive therapeutic response with respect to treatment of a patient with a cancer or pre-malignant condition associated with CD40-expressing cells. Suitable dosages are described in more detail elsewhere herein. The method of treatment may comprise a single administration of a therapeutically effective dose or multiple administrations of a therapeutically effective dose of the anti-CD40 antibody, as described in more detail elsewhere herein.

"Tumor", as used herein, refers to all neoplastic cell growth and proliferation, whether malignant or benign, and all precancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The terms "cancer" and "cancerous" refer to or describe the physiological condition in mammals that is typically characterized by unregulated cell growth. Examples of cancer include, but are not limited to, lymphoma and leukemia, and solid tumors. By "B cell-related cancer" or "cancer of B-cell lineage" is intended any type of cancer in which the dysregulated or unregulated cell growth is associated with B cells.

"Treatment" is herein defined as the application or administration of an anti-CD40 antibody to a patient, or application or administration of an anti-CD40 antibody to an isolated tissue or cell line from a patient, where the patient has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the application or administration of a pharmaceutical composition comprising the anti-CD40 antibody to a patient, or application or administration of a pharmaceutical composition comprising the anti-CD40 antibody, to an isolated tissue or cell line from a patient, who has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

By "anti-tumor activity" is intended a reduction in the rate of malignant CD40-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD40 antibody causes a physiological response that is beneficial with respect to treatment of disease states associated with stimulation of CD40 signaling on CD40-expressing cells in a human.

The methods of the invention are particularly useful for treating cancers and pre-malignant conditions, including those listed above, that are refractory to first-line oncotherapeutic treatments. The term "oncotherapeutic" is intended to mean any treatment for cancer, such as chemotherapy, surgery, radiation therapy, anti-cancer antibody therapy, and combinations thereof. Examples of oncotherapeutic treatments are described in more detail elsewhere herein. By "refractory" is intended the particular cancer is resistant to, or non-responsive to, therapy with a particular oncotherapeutic agent. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent. Thus, the present invention is useful for treating a human patient who is refractory to therapy with an anti-cancer agent, when that human patient is either resistant to therapy or non-responsive to therapy with the anti-cancer agent.

The methods of the present invention involve the use of anti-CD40 antibodies. "Antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains. The term "variable" refers to the fact that certain portions of the variable domains differ extensively in sequence among antibodies. The variable regions confer antigen-binding specificity. The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their "heavy chains", immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity. IgG1 antibodies, in particular human IgG1 antibodies, are particularly useful in the methods of the present invention.

"Human effector cells" are leukocytes that express one or more FcRs and perform effector functions. Preferably, the cells express at least FcγRIII and carry out antigen-dependent cell-mediated cyotoxicity (ADCC) effector function. Examples of human leukocytes that mediate ADCC include peripheral blood mononuclear cells (PBMC), natural killer (NK) cells, monocytes, macrophages, eosinophils, and neutrophils, with PBMCs and NK cells being preferred. Antibodies that have ADCC activity are typically of the IgG1 or IgG3 isotype. Note that in addition to isolating IgG1 and IgG3 antibodies, such ADCC-mediating antibodies can be made by engineering a variable region from a non-ADCC antibody or variable region fragment to an IgG1 or IgG3 isotype constant region.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daeron (1997) *Annu. Rev. Immunol.* 15:203-234). FcRs are reviewed in Ravetch and Kinet (1991) *Annu. Rev. Immunol.* 9:457-492 (1991); Capel et al. (1994) Immunomethods 4:25-34; and de Haas et al. (1995) *J. Lab. Clin. Med.* 126:330-341. Other FcRs, including those to be identified in the future, are encompassed by the term "FcR" herein. The term also includes the neonatal receptor, FcRn, which is responsible for the transfer of maternal IgGs to the fetus (Guyer et al. (1976) *J. Immunol.* 117:587 and Kim et al. (1994) *J. Immunol.* 24:249 (1994)).

The term "antibody" is used herein in the broadest sense and covers fully assembled antibodies, antibody fragments which retain the ability to specifically bind to the CD40 antigen (e.g., Fab, F(ab')$_2$, Fv, and other fragments), single chain antibodies, diabodies, antibody chimeras, hybrid antibodies, bispecific antibodies, humanized antibodies, and the like), and recombinant peptides comprising the forgoing. The term "antibody" covers both polyclonal and monoclonal antibodies.

As used herein "anti-CD40 antibody" encompasses any antibody that specifically recognizes the CD40 antigen. In some embodiments, anti-CD40 antibodies for use in the methods of the present invention, in particular monoclonal anti-CD40 antibodies, exhibit a strong single-site binding affinity for the CD40 antigen. Such monoclonal antibodies exhibit an affinity for CD40 ($K_D$) of at least $10^{-5}$ M, at least $3 \times 10^{-5}$ M, preferably at least $10^{-6}$ M, or at least to $10^{-7}$ M, more preferably at least $10^{-8}$ M, or at least $10^{-12}$ M, when measured using a standard assay such as Biacore™. Biacore analysis is known in the art and details are provided in the "BIAapplications handbook". Methods described in WO 01/27160 can be used to modulate the binding affinity.

By "specifically recognizes" or "specifically binds to" is intended that the anti-CD40 antibody does not bind to unrelated antigens, such as the CD20 antigen.

In some embodiments, anti-CD40 antibodies for use in the methods of the present invention, in particular monoclonal antibodies, exhibit a strong binding affinity for human FcγRIIIa-158V. Preferably, an anti-CD40 antibody for use in the methods of the invention binds to human FcγRIIIa-158V with an affinity ($K_D$) of at least about 0.5 μM when measured using a standard assay such as Biacore™. As disclosed in Example 6 herein, the CHIR-12.12 antibody binds to human FcγRIIIa-158V with an affinity ($K_D$) of 492 nM.

In some embodiments, anti-CD40 antibodies for use in the methods of the present invention, in particular monoclonal antibodies, exhibit a strong binding affinity for human FcγRIIIa-158F. Preferably, an anti-CD40 antibody for use in the methods of the invention binds to human FcγRIIIa-158F with an affinity ($K_D$) of at least about 12 μM when measured using a standard assay such as Biacore™. Preferably, the anti-CD40 antibody for use in the methods of the invention binds to human FcγRIIIa-158F with an affinity ($K_D$) of at least about 10 μM, at least about 8 μM, at least about 6 μM, at least about 5 μM, at least about 4 μM, or at least about 3 μM. As disclosed in Example 6 herein, the CHIR-12.12 antibody binds to human FcγRIIIa-158F with an affinity ($K_D$) of 2.8 μM.

In some embodiments, anti-CD40 antibodies for use in the methods of the present invention, in particular monoclonal antibodies, exhibit a strong binding affinity for both human FcγRIIIa-158V and FcγRIIIa-158F. Preferably, an anti-CD40 antibody for use in the methods of the invention binds to human FcγRIIIa-158V with an affinity ($K_D$) of at least about 0.5 μM and binds to human FcγRIIIa-158F with an affinity ($K_D$) of at least about 12 μM, when measured using a standard assay such as Biacore™.

The antibodies for use in the methods of the present invention can be produced using any suitable antibody production method known to those of skill in the art.

The anti-CD40 antibody used in the methods of the present invention may be a polyclonal antibody. Thus, polyclonal sera may be prepared by conventional methods. In general, a solution containing the antigen of interest (in this case, the CD40 antigen) is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Sera from immunized animals may be screened for antibody reactivity against the initial antigen. Lymphocytes may be isolated from lymph nodes or spleen cells and may further be selected for B cells by selecting for CD138-negative and CD19-positive cells. In one aspect, such B cell cultures (BCCs) may be fused to myeloma cells to generate hybridomas as detailed herein.

Polyclonal sera can also be prepared in a transgenic animal, preferably a mouse bearing human immunoglobulin loci. In a preferred embodiment, Sf9 cells expressing the protein of interest (in this case, the CD40 antigen), are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf 9 (*Spodoptera frugiperda*) cells is disclosed in U.S. Pat. No. 6,004,552, incorporated herein by reference. In the case of CD40, briefly, sequences encoding human CD40 were recombined into a baculovirus using transfer vectors. The plasmids were co-transfected with wild-type baculovirus DNA into Sf 9 cells. Recombinant baculovirus-infected Sf 9 cells were identified and clonally purified.

The anti-CD40 antibody used in the methods of the present invention may be a monoclonal antibody. The term "monoclonal antibody" (and "mAb") as used herein refers to an antibody obtained from a substantially homogeneous population of antibodies, i.e., the individual antibodies comprising the population are identical except for possible naturally occurring mutations that may be present in minor amounts. The term is not limited regarding the species of the antibody and does not require production of the antibody by any particular method.

In contrast to polyclonal antibody preparations, which typically include different antibodies directed against different antigenic determinants (epitopes), each monoclonal antibody is directed against a single determinant (epitope) on the antigen.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), non-linear amino acid residues (referred to herein as "non-linear epitopes"; these epitopes are not arranged sequentially), or both linear and non-linear amino acid residues. An anti-CD40 monoclonal antibody suitable for use in the methods of the present invention will be capable of specifically binding to an epitope on human CD40 antigen expressed on the surface of a human cell, i.e. an epitope that is exposed to the exterior of the cell.

The monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). Monoclonal antibodies may also be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

In the traditional method of Kohler et al (1975) *Nature* 256:495-496, typically a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

In another aspect, B cell cultures may be screened further for reactivity against the initial antigen, preferably. Such screening includes enzyme-linked immunosorbent assay (ELISA) with the target/antigen protein, a competition assay with known antibodies that bind the antigen of interest, and in vitro binding to transiently transfected CHO or other cells that express the target antigen.

Where anti-CD40 antibodies for use in the methods of the invention are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al. (1993) Curr. Opinion in Immunol. 5:256 and Phickthun (1992) Immunol. Revs. 130:151. Alternatively, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

A "host cell," as used herein, refers to a microorganism or a eukaryotic cell or cell line cultured as a unicellular entity that can be, or has been, used as a recipient for a recombinant vector or other transfer polynucleotides, and include the progeny of the original cell that has been transfected. It is understood that the progeny of a single cell may not necessarily be completely identical in morphology or in genomic or total DNA complement as the original parent, due to natural, accidental, or deliberate mutation.

In some embodiments, the anti-CD40 antibody, such as CHIR-12.12, can be produced in CHO cells using the GS gene expression system (Lonza Biologics, Portsmouth, N.H.), which uses glutamine synthetase as a marker. See, also U.S. Pat. Nos. 5,122,464; 5,591,639; 5,658,759; 5,770,359; 5,827,739; 5,879,936; 5,891,693; and 5,981,216; the contents of which are herein incorporated by reference in their entirety.

Monoclonal antibodies to CD40 are known in the art. See, for example, the sections dedicated to B-cell antigen in McMichael, ed. (1987; 1989) Leukocyte Typing III and IV (Oxford University Press, New York); U.S. Pat. Nos. 5,674, 492; 5,874,082; 5,677,165; 6,056,959; WO 00/63395; International Publication Nos. WO 02/28905 and WO 02/28904; Gordon et al. (1988) J. Immunol. 140:1425; Valle et al. (1989) Eur. J. Immunol. 19:1463; Clark et al. (1986) PNAS 83:4494; Paulie et al. (1989) J. Immunol. 142:590; Gordon et al. (1987) Eur. J. Immunol. 17:1535; Jabara et al. (1990) J. Exp. Med. 172:1861; Zhang et al. (1991) J. Immunol. 146:1836; Gascan et al. (1991) J. Immunol. 147:8; Banchereau et al. (1991) Clin. Immunol. Spectrum 3:8; and Banchereau et al. (1991) Science 251:70; all of which are herein incorporated by reference.

As noted above, the term "antibody" as used herein encompasses chimeric antibodies. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the antigen of interest (CD40). The non-human source can be any vertebrate source that can be used to generate antibodies to CD40 antigen. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference).

As noted above, the term "antibody" as used herein encompasses humanized antibodies. By "humanized" is intended forms of antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural Fv region of a native immunoglobulin binding site. See, e.g., Chothia et al (1987) J. Mol. Biol. 196:901-917; Kabat et al (1991) U.S. Dept. of Health and Human Services, NIH Publication No. 91-3242). The phrase "constant region" refers to the portion of the antibody molecule that confers effector functions. In previous work directed towards producing non-immunogenic antibodies for use in therapy of human disease, mouse constant regions were substituted by human constant regions. The constant regions of the subject humanized antibodies were derived from human immunoglobulins. However, these humanized antibodies can elicit an unwanted and potentially dangerous immune response in humans and there was a loss of affinity.

Humanization can be performed following the method of Winter and co-workers (Jones et al. (1986) Nature 321:522-525; Riechmann et al. (1988) Nature 332:323-327; Verhoeyen et al. (1988) Science 239:1534-1536), by substituting rodent or mutant rodent CDRs or CDR sequences for the corresponding sequences of a human antibody. See also U.S. Pat. Nos. 5,225,539; 5,585,089; 5,693,761; 5,693,762; 5,859, 205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) Nature 331:522-525; Riechmann et al. (1988) Nature 332:323-329; and Presta (1992) Curr. Op. Struct. Biol. 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

Humanized anti-CD40 antibodies can also be produced using the Human Engineering™ technology (Xoma Ltd., Berkeley, Calif.).

Humanized anti-CD40 monoclonal antibodies include antibodies such as SGN-40 (Tai et al. (2004) *Cancer Res.* 64:2846-52; U.S. Pat. No. 6,838,261), which is the humanized form of the murine anti-CD40 antibody SGN-14 (Francisco et al. (2000) *Cancer Res.* 60:3225-31), and the antibodies disclosed in U.S. Patent Application Publication No. 2004/0120948; herein incorporated by reference in their entirety.

The present invention can also be practiced using xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598, herein incorporated by reference.

Thus, in some embodiments, fully human antibodies to CD40, for example, are obtained by immunizing transgenic mice. One such mouse is obtained using XenoMouse® technology (Abgenix; Fremont, Calif.), and is disclosed in U.S. Pat. Nos. 6,075,181, 6,091,001, and 6,114,598, all of which are incorporated herein by reference. For example, to produce the CHIR-12.12 antibody, mice transgenic for the human Ig $G_1$ heavy chain locus and the human κ light chain locus were immunized with Sf9 cells expressing human CD40. Mice can also be transgenic for other isotypes. Fully human anti-CD40 antibodies useful in the methods of the present invention are characterized by binding properties similar to those exhibited by the CHIR-12.12 monoclonal antibody.

As noted above, the term "antibody" as used herein also encompasses antibody fragments that can bind antigen. "Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) *Protein Eng.* 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy chain $C_H1$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

Fragments of an anti-CD40 antibody are suitable for use in the methods of the invention so long as they retain the desired affinity of the full-length antibody. Thus, for example, a fragment of an anti-CD40 antibody will retain the ability to bind to the CD40 antigen. Such fragments are characterized by properties similar to the corresponding full-length antibody. Thus, for example, a fragment of a full-length antagonist anti-CD40 antibody will preferably be capable of specifically binding a human CD40 antigen expressed on the surface of a human cell, and is free of significant agonist activity but exhibits antagonist activity when bound to a CD40 antigen on a human CD40-expressing cell. Such fragments are referred to herein as "antigen-binding" fragments. Fragments of an anti-CD40 antibody for use in the methods of the invention will also preferably retain the ability to bind to the relevant FcR or FcRs. Thus, for example, a fragment of an anti-CD40 antibody may retain the ability to bind to FcγRIIIa. Thus, for example, a fragment of a full-length anti-CD40 antibody may be capable of binding specifically to a cell-surface CD40 antigen, and also capable of binding to FcγRIIIa on human effector cells, such as natural killer (NK) cells. Such fragments are referred to herein as "FcR-binding" fragments. Such fragments will generally include at least part of the constant domain of the heavy chain.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By F(ab')$_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315. Antigen-binding fragments of the antagonist anti-CD40 antibodies disclosed herein can also be conjugated to a cytotoxin to effect killing of the target cancer cells, as described herein below.

In some embodiments of the invention, the anti-CD40 antibody is an antagonist anti-CD40 antibody. When such antibodies bind CD40 displayed on the surface of human cells, such as human B cells, they do not cause significant agonist activity. In some embodiments, their binding to CD40 displayed on the surface of human cells results in inhibition of proliferation and differentiation of these human cells. The anti-CD40 antibodies suitable for use in the methods of the invention include those antibodies that can exhibit antagonist activity toward normal and malignant human cells expressing the cell-surface CD40 antigen.

By "agonist activity" is intended that a substance functions as an agonist. An agonist combines with a receptor on a cell and initiates a reaction or activity that is similar to or the same as that initiated by the receptor's natural ligand. An agonist of CD40 induces any or all of, but not limited to, the following responses: B cell proliferation and/or differentiation; upregulation of intercellular adhesion via such molecules as ICAM-1, E-selectin, VCAM, and the like; secretion of pro-inflammatory cytokines such as IL-1, IL-6, IL-8, IL-12, TNF, and the like; signal transduction through the CD40 receptor by such pathways as TRAF (e.g., TRAF2 and/or TRAF3), MAP kinases such as NIK (NF-κB inducing kinase), 1-kappa B kinases (IKK α/β), transcription factor NF-κB, Ras and the MEK/ERK pathway, the PI3K/AKT pathway, the P38 MAPK pathway, and the like; transduction of an anti-apoptotic signal by such molecules as XIAP, mcl-1, bcl-x, and the like; B and/or T cell memory generation; B cell antibody production; B cell isotype switching, up-regulation of cell-surface expression of MHC Class II and CD80/86, and the like.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in an assay of a B cell response. Preferably, "significant" agonist activity is an agonist activity that is at least 2-fold greater or at least 3-fold greater than the agonist activity induced by a neutral substance or negative control as measured in an assay of a B cell response. Thus, for example, where the B cell response of interest is B cell proliferation, "significant" agonist activity would be induction of a level of B cell proliferation that is at least 2-fold greater or at least 3-fold greater than the level of B cell proliferation induced by a neutral substance or negative control. In one embodiment, a non-specific immunoglobulin, for example IgG1, that does not bind to CD40 serves as the negative control. A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in an assay of a B cell response.

By "antagonist activity" is intended that the substance functions as an antagonist. An antagonist of CD40 prevents or reduces induction of any of the responses induced by binding of the CD40 receptor to an agonist ligand, particularly CD40L. The antagonist may reduce induction of any one or more of the responses to agonist binding by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. Methods for measuring CD40 ligand binding specificity and antagonist activity of an anti-CD40 therapeutic agent, for example, an anti-CD40 antibody, are known in the art and include, but are not limited to, standard competitive binding assays, assays for monitoring immunoglobulin secretion by B cells, B cell proliferation assays, Banchereau-Like-B cell proliferation assays, T cell helper assays for antibody production, co-stimulation of B cell proliferation assays, and assays for up-regulation of B cell activation markers. See, for example, such assays disclosed in WO 00/75348 and U.S. Pat. No. 6,087,329, herein incorporated by reference. Also see WO 2005/044854, WO 2005/044304, WO 2005/044305, WO 2005/044306, WO 2005/044855, WO 2005/044307, and WO 2005/044294WO, the contents of each of which are herein incorporated by reference in their entirety.

Antagonist/lack of agonist activity can be evaluated by assays showing that CHIR-12.12 lacks agonist activity. Suitable assays are shown in the assays described in U.S. Pat. No. 5,677,165 (Chiron Corporation).

In one embodiment of the invention, the antagonist anti-CD40 antibody is free of significant agonist activity in one cellular response. In another embodiment of the invention, the antagonist anti-CD40 antibody is free of significant agonist activity in assays of more than one cellular response (e.g., proliferation and differentiation, or proliferation, differentiation, and, for B cells, antibody production).

Of particular interest are antagonist anti-CD40 antibodies that are free of significant agonist activity as defined herein but exhibit antagonist activity when bound to CD40 antigen on human B cells. In one embodiment of the invention, the antagonist anti-CD40 antibody is free of significant agonist activity in one B cell response. In another embodiment of the invention, the antagonist anti-CD40 antibody is free of significant agonist activity in assays of more than one B cell response (e.g., proliferation and differentiation, or proliferation, differentiation, and antibody production).

Any of the assays known in the art can be used to determine whether an anti-CD40 antibody acts as an antagonist of one or more B cell responses. In some embodiments, the anti-CD40 antibody acts as an antagonist of at least one B cell response selected from the group consisting of B cell proliferation, B cell differentiation, antibody production, intercellular adhesion, B cell memory generation, isotype switching, up-regulation of cell-surface expression of MHC Class II and CD80/86, and secretion of pro-inflammatory cytokines such as IL-8, IL-12, and TNF. Of particular interest are antagonist anti-CD40 antibodies that free of significant agonist activity with respect to B cell proliferation when bound to the human CD40 antigen on the surface of a human B cell.

The anti-CD40 antibody may be an antagonist of B cell proliferation induced by soluble or cell-surface CD40L, as measured in a B cell proliferation assay. Suitable B cell proliferation assays are known in the art. Suitable B cell proliferation assays are also described below. In some embodiments, the antagonist anti-CD40 antibody stimulates B cell proliferation at a level that is not more than about 25% greater than the B cell proliferation induced by a neutral substance or negative control, preferably not more than about 20% greater, 15% greater, 10% greater, 5% greater, 1% greater, 0.5% greater, or even not more than about 0.1% greater than the B cell proliferation induced by a neutral substance or negative control.

In other embodiments, the anti-CD40 antibody is an antagonist of B cell proliferation that is induced by another anti-CD40 antibody, for example, the S2C6 anti-CD40 antibody, as measured in a B cell proliferation, and the level of B cell proliferation stimulated by the other anti-CD40 antibody in the presence of the antagonist anti-CD40 antibody is not more than about 25% of the B cell proliferation induced by the other anti-CD40 antibody in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by the other anti-CD40 antibody in the absence of the antagonist anti-CD40 antibody.

In yet other embodiments, the anti-CD40 antibody is an antagonist of B cell proliferation that is induced by the cell line EL4B5 as measured in a B cell activation assay, and the level of B cell proliferation stimulated by the EL4B5 cell line in the presence of the antagonist anti-CD40 antibody is not more than about 25% of the B cell proliferation induced by this cell line in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by this cell line in the absence of the antagonist anti-CD40 antibody.

In still other embodiments, the anti-CD40 antibody is an antagonist of human T-cell-induced antibody production by human B cells as measured in the human T-cell helper assay for antibody production by B cells. In this manner, the level of IgG antibody production, IgM antibody production, or both IgG and IgM antibody production by B cells stimulated by T cells in the presence of the antagonist anti-CD40 antibody is not more than about 50% of the respective antibody production by B cells stimulated by T cells in the absence of the antagonist anti-CD40 antibody (i.e., at least 75% inhibition), preferably not more than about 25%, 20%, 15%, 10%, 5%, 1%, 0.5%, or even not more than about 0.1% of the respective antibody production by B cells stimulated by T cells in the absence of the antagonist anti-CD40 antibody. Additional antagonist anti-CD40 antibodies include the monoclonal antibodies referred to as 5D12, 3A8 and 3C6, which are secreted by a hybridoma having ATCC accession numbers HB 11339, HB 12024 and HB 11340, respectively. See, for example, U.S. Pat. No. 6,315,998, herein incorporated by reference in its entirety.

For example, the following assays can be used to assess the antagonist activity of an anti-CD40 antibody. Human B cells for these assays can be obtained, for example, by isolation from tonsils obtained from individuals undergoing tonsillectomies, essentially as described in De Groot et al. (1990) *Lymphokine Research* (1990) 9:321. Briefly, the tissue is dispersed with scalpel blades, phagocytic and NK cells are depleted by treatment with 5 mM L-leucine methyl ester and T cells are removed by one cycle of rosetting with sheep erythrocytes (SRBC) treated with 2-aminoethyl isothiouronium bromide. The purity of the resulting B lymphocyte preparations can be checked by indirect immunofluorescent labelling with anti-(CD20) mAb B1 (Coulter Clone, Hialeah, Fla.) or anti-(CD3) mAb OKT3 (Ortho, Raritan, N.J.) and a FITC-conjugated F(ab')$_2$ fragment of rabbit anti-(mouse Ig) (Zymed, San Francisco, Calif.), and FACS analysis.

B-Cell Proliferation Assay

B cells ($4 \times 10^4$ per well) are cultured in 200 µl IMDM supplemented with 10% fetal calf serum in flat bottom 96-well microtiter plates. B cells are stimulated by addition of immobilized anti-(IgM) antibodies (Immunobeads; 5 µg/ml; BioRad, Richmond, Calif.). Where desired, 100 U/ml recombinant IL-2 is added. Varying concentrations of test monoclonal antibodies (mAbs) are added at the onset of the microcultures and proliferation is assessed at day 3 by measurement of the incorporation of (3H)-thymidine after 18 hour pulsing. An antagonist anti-CD40 antibody does not significantly costimulate human B-cell proliferation in the presence of immobilized anti-IgM or in the presence of immobilized anti-IgM and IL-2.

Banchereau-Like B-Cell Proliferation Assay

For testing the ability of anti-CD40 monoclonal antibodies to stimulate B-cell proliferation in a culture system analogous to that described by Banchereau et al. (1991) *Science* (1991) 251:70, mouse 3T6 transfectant cells expressing the HR allelic form of human FcγRII are used. B cells ($2 \times 10^4$ per well) are cultured in flat-bottom microwells in the presence of $1 \times 10^4$ transfectant cells (irradiated with 5000 Rad) in 200 µl IMDM supplemented with 10% fetal calf serum and 100 U/ml recombinant IL-4. Before addition of the B cells, the 3T6 cells are allowed to adhere to the culture plastic for at least 5 hours. Anti-CD40 mAbs are added at concentrations varying from 15 ng/ml to 2000 ng/ml and proliferation of B cells is assessed by measurement of thymidine incorporation at day 7, upon 18 hour pulsing with [$^3$H]thymidine.

Inhibition of S2C6-Stimulated B-Cell Proliferation Using Antagonist Anti-CD40 mAbs Antagonist anti-CD40 monoclonal antibodies (mAbs) can also be characterized by their ability to inhibit stimulation of B-cell proliferation by an anti-CD40 antibody such as S2C6 (also known as SGN-14, which is reportedly an agonist of CD40 stimulation of proliferation of normal B cells; Francisco et al. (2000) *Cancer Res.* 60:3225-3231) using the B-cell Proliferation Assay described above. Human tonsillar B cells ($4 \times 10^4$ per well) are cultured in 200 µl in microwells in the presence of anti-IgM coupled to Sepharose beads (5 µg/ml) and anti-CD40 mAb S2C6 (1.25 µg/ml). Varying concentrations of an anti-CD40 mAb of interest are added and [$^3$H]-thymidine incorporation is assessed after 3 days. As a control anti-(glucocerebrosidase) mAb 8E4 can be added in similar concentrations. Barneveld et al. (1983) *Eur. J. Biochem.* 134:585. An antagonist anti-CD40 antibody can inhibit the costimulation of anti-IgM induced human B-cell proliferation by mAb S2C6, for example, by at least 75% or more (i.e., S2C6-stimulated proliferation in the presence of an antagonist anti-CD40 antibody is no more than 25% of that observed in the absence of the antagonist anti-CD40 antibody). In contrast, no significant inhibition would be seen with equivalent amounts of non-relevant mAb 8E4, directed to β-glucocerebrosidase. Barneveld et al., supra. Such a result would indicate that the anti-CD40 mAbs does not deliver stimulatory signals for the proliferation of human B cells, but, conversely, can inhibit stimulatory signals exerted by triggering CD40 with another mAb.

B-Cell Activation Assay with EL4B5 Cells

Zubler et al. (1985) *J. Immunol.* (1985) 134:3662 observed that a mutant subclone of the mouse thymoma EL-4 line, known as EL4B5, could strongly stimulate B cells of both murine and human origin to proliferate and differentiate into immunoglobulin-secreting plasma cells in vitro. This activation was found to be antigen-independent and not MHC restricted. For optimal stimulation of human B cells, the presence of supernatant from activated human T cells was needed but a B-cell response also occurred when EL4B5 cells were preactivated with phorbol-12-myristate 13-acetate (PMA) or IL-1. Zubler et al. (1987) *Immunological Reviews* 99:281; and Zhang et al. (1990) *J. Immunol.* 144:2955. B-cell activation in this culture system is efficient—limiting dilution experiments have shown that the majority of human B cells can be activated to proliferate and differentiate into antibody-secreting cells. Wen et al. (1987) *Eur. J. Immunol.* 17:887.

B cells (1000 per well) are cultured together with irradiated (5000 Rad) EL4B5 cells ($5\times10^4$ per well) in flat bottom microtiter plates in 200 µl IMDM supplemented with 10% heat-inactivated fetal calf serum, 5 ng/ml phorbol-12-myristate 13-acetate (Sigma) and 5% human T-cell supernatant. mAbs are added at varying concentrations at the onset of the cultures and thymidine incorporation is assessed at day 6 after 18 hour pulsing with [$^3$H]-thymidine. For the preparation of T-cell supernatant, purified T cells are cultured at a density of $10^6$/ml for 36 hours in the presence of 1 µg/ml PHA and 10 ng/ml PMA. Wen et al. (1987) *Eur. J. Immunol.* (1987) 17:887. T-cell supernatant is obtained by centrifugation of the cells and stored at −20° C. The effectiveness of T-cell supernatants in enhancing proliferation of human B cells in EL4B5-B cell cultures is tested and the most effective supernatants are pooled for use in experiments. When assessing the effect of an anti-CD40 antibody on EL4B5-induced human B-cell proliferation, a monoclonal antibody such as MOPC-141 (IgG2b) can be added as a control.

An antagonist anti-CD40 antibody can inhibit B-cell proliferation stimulated by the EL4B5 cell line, for example, by at least 75% or more (i.e., EL4B5-induced B cell proliferation in the presence of an antagonist anti-CD40 antibody is no more than 25% of that observed in the absence of the antagonist anti-CD40 antibody). In contrast, a control antibody such as MOPC-141 would have no significant effect on EL4B5-induced B cell proliferation.

Human T Cell Helper Assay for Antibody Production by B Cells

An antagonist anti-CD40 antibody can function as an antagonist of immunoglobulin production by B cells. An anti-CD40 antibody can be tested for this type of antagonist activity by assessing the antibody's ability to inhibit immunoglobulin production by B cells that have been stimulated in a contact-dependent manner with activated T cells in a T cell helper assay. In this manner, 96-well tissue culture plates are coated with a 1:500 dilution of ascites fluid of anti-CD3 mAb CLB-T3/3 (CLB, Amsterdam, The Netherlands). As indicated costimulatory mAbs are added: anti CD2 mAbs CLB-T11.1/1 and CLB-T11.2/1 (CLB, Amsterdam, The Netherlands), both ascites 1:1000 and anti-CD28 mAb CLB-28/1 (CLB, Amsterdam, The Netherlands). Subsequently, tonsillar T cells (irradiated, 3000 Rad; $10^5$ per well), tonsillar B cells ($10^4$ per well), and rIL-2 (20 U/ml) are added. The final volume of each cell culture is 200 µl. After 8 days, cells are spun down, and cell-free supernatant is harvested. The concentrations of human IgM and IgG in (diluted) samples is estimated by ELISA as described below.

In one embodiment, human tonsillar B cells ($10^4$/well) are cultured together with irradiated purified T cells (3000 rad, $10^5$/well) in 96-well plates, coated with anti-CD3 mAb and with or without different mAbs to costimulate the T cells. After 8 days of culture the supernatants are harvested for the determination of immunoglobulin production by the B cells. Immunoglobulin production by the B cells is assessed by the ELISA assay described below. The anti-CD40 antibody of interest is added in varying concentrations from the onset of the cultures. As a control, mAb MOPC-141 can be added.

An antagonist anti-CD40 antibody can inhibit IgG and IgM antibody production of B cells stimulated by human T cells by at least 50% or more (i.e., T cell-induced antibody production by B cells in the presence of an antagonist anti-CD40 antibody is no more than 50% of that observed in the absence of the antagonist anti-CD40 antibody). In contrast, a control antibody such as MOPC-141 would have no significant effect on T cell-induced antibody production by B cells.

ELISA Assay for Immunoglobulin Quantification

The concentrations of human IgM and IgG are estimated by ELISA. 96-well ELISA plates are coated with 4 µg/ml mouse anti-human IgG mAb MH 16-01 (CLB, Amsterdam, The Netherlands) or with 1.2 µg/ml mouse anti-human IgM mAb 4102 (Tago, Burlingame, Calif.) in 0.05 M carbonate buffer (pH=9.6), by incubation for 16 h at 4° C. Plates are washed 3 times with PBS-0.05% Tween-20 (PBS-Tween) and saturated with BSA for 1 hour. After 2 washes the plates are incubated for 1 h at 37° C. with different dilutions of the test samples. After 3 washes, bound Ig is detected by incubation for 1 h at 37° C. with 1 µg/ml peroxidase-labeled mouse anti-human IgG mAb MH 16-01 (CLB) or mouse anti-human IgM mAb MH 15-01 (CLB). Plates are washed 4 times and bound peroxidase activity is revealed by the addition of O-phenylenediamine as a substrate. Human standard serum (H00, CLB) is used to establish a standard curve for each assay.

Antagonist anti-CD40 antibodies are known in the art. See, for example, the human anti-CD40 antibody produced by the hybridoma designated F4-465 disclosed in U.S. Patent Application Publication Nos. 20020142358 and 20030059427; herein incorporated by reference in their entirety. F4-465 was obtained from the HAC mouse (Kuroiwa et al. (2000) *Nature Biotech.* 10:1086 (2000)) and therefore expresses the human lambda light chain. Also see WO 2005/044854, WO 2005/044304, WO 2005/044305, WO 2005/044306, WO 2005/044855, WO 2005/044307, and WO 2005/044294WO, the contents of each of which are herein incorporated by reference in their entirety.

In addition to antagonist activity, the anti-CD40 antibody for use in the methods of the present invention will preferably have another mechanism of action against a target cell. For example, the anti-CD40 antibody will preferably have ADCC activity. Alternatively, the variable regions of the anti-CD40 antibody can be expressed on another antibody isotype that has ADCC activity. It is also possible to conjugate native forms, recombinant forms, or antigen-binding fragments of anti-CD40 antibodies to a cytotoxin, a therapeutic agent, or a radioactive metal ion or radioisotope, as described further elsewhere herein.

As explained elsewhere herein, the inventors have made the surprising finding that, contrary to other antibodies, anti-CD40 antibodies, such as CHIR-12.12, are able to mediate potent antibody-dependent cellular cytotoxicity (ADCC) of CD40-expressing target cells via binding to either of the two FcγRIIIa amino acid 158 allotypes (V or F) on a human patient's natural killer (NK) cells. Accordingly, anti-CD40 antibodies, such as CHIR-12.12, can be used in the treatment of cancers and pre-malignant conditions associated with CD40-expressing cells in human patients heterozygous or homozygous for FcγRIIIa-158F (genotype V/F or F/F), in addition to human patients homozygous for FcγRIIIa-158V (genotype V/V). The present invention is especially advantageous for the treatment of cancers and pre-malignant conditions that are not responsive to treatment with rituximab (Rituxan®), because the clinical activity of rituximab in NHL has been shown to be correlated with the patient's FcγRIIIa genotype.

Thus, particularly preferred anti-CD40 antibodies for use in the methods of the present invention are those which, in addition to antagonist activity, are capable of mediating ADCC of CD40-expressing cells by human effector cells, such as natural killer cells (NK cells) expressing FcγRIIIa. Most preferred are those anti-CD40 antibodies that are capable of binding both FcγRIIIa-158F and FcγRIIIa-158V with high affinity, as described further elsewhere herein.

Particularly preferred anti-CD40 antibodies are those disclosed in WO 2005/044854, WO 2005/044304, WO 2005/044305, WO 2005/044306, WO 2005/044855, WO 2005/044307, and WO 2005/044294WO, the contents of each of which are herein incorporated by reference in their entirety.

Of particular interest to the present invention are antagonist anti-CD40 antibodies that share the binding characteristics of the CHIR-12.12 monoclonal antibody described in WO 2005/044854, WO 2005/044304, WO 2005/044305, WO 2005/044306, WO 2005/044855, WO 2005/044307, and WO 2005/044294. Such antibodies include, but are not limited to the following:

a) the monoclonal antibody CHIR-12.12;

b) the monoclonal antibody produced by the hybridoma cell line 12.12;

c) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5;

d) a monoclonal antibody having an amino acid sequence encoded by a nucleic acid molecule comprising a nucleotide sequence selected from the group consisting of the sequence shown in SEQ ID NO: 1, the sequence shown in SEQ ID NO:3, and both the sequences shown in SEQ ID NO: 1 and SEQ ID NO:3;

e) a monoclonal antibody that binds to an epitope capable of binding the monoclonal antibody produced by the hybridoma cell line 12.12;

f) a monoclonal antibody that binds to an epitope comprising residues 82-87 of the human CD40 sequence shown in SEQ ID NO:7 or SEQ ID NO:9;

g) a monoclonal antibody that binds to an epitope comprising residues 82-89 of the human CD40 sequence shown in SEQ ID NO:7 or SEQ ID NO:9;

h) a monoclonal antibody that competes with the monoclonal antibody CHIR-12.12 in a competitive binding assay;

i) the monoclonal antibody of preceding item a) or a monoclonal antibody of any one of preceding items c)-h), wherein said antibody is recombinantly produced; and j) a monoclonal antibody that is an antigen-binding fragment of a monoclonal antibody of any one of preceding items a)-i), wherein said fragment retains the capability of specifically binding to human CD40 antigen.

The monoclonal antibody CHIR-12.12 is particularly preferred for use in the methods of the present invention.

The monoclonal antibody CHIR-12.12 was described in detail in WO 2005/044854, WO 2005/044304, WO 2005/044305, WO 2005/044306, WO 2005/044855, WO 2005/044307, and WO 2005/044294. The CHIR-12.12 antibody is a fully human anti-CD40 monoclonal antibody of the IgG, isotype produced from the hybridoma cell line 153.8E2.D10.D6.12.12 (referred to as the cell line 12.12). The cell line was created using splenocytes from immunized xenotypic mice containing the human IgG1 heavy chain locus and the human K chain locus (XenoMouse® technology; Abgenix; Fremont, Calif.). The spleen cells were fused with the mouse myeloma SP2/0 cells (Sierra BioSource). The resulting hybridomas were sub-cloned several times to create the stable monoclonal cell line 12.12. Other antibodies suitable for use in the methods of the invention may be prepared similarly using mice transgenic for human immunoglobulin loci, as described elsewhere herein.

The CHIR-12.12 monoclonal antibody binds soluble CD40 in ELISA-type assays, prevents the binding of CD40-ligand to cell-surface CD40, and displaces the pre-bound CD40-ligand, as determined by flow cytometric assays. Antibodies CHIR-5.9 and CHIR-12.12 compete with each other for binding to CD40 but not with 15B8, the anti-CD40 monoclonal antibody described in U.S. Provisional Application Ser. No. 60/237,556, titled "Human Anti-CD40 Antibodies," filed Oct. 2, 2000, and PCT International Application No. PCT/US01/30857, also titled "Human Anti-CD40 Antibodies," filed Oct. 2, 2001 and published as WO 2002/028904, both of which are herein incorporated by reference in their entirety. When tested in vitro for effects on proliferation of B cells from normal human subjects, CHIR-12.12 acts as antagonist anti-CD40 antibody. Furthermore, CHIR-12.12 does not induce strong proliferation of human lymphocytes from normal subjects. The antibody is able to kill CD40-expressing target cells by antibody dependent cellular cytotoxicity (ADCC). The binding affinity of CHIR-12.12 for human CD40 is $5 \times 10^{10}$M, as determined by the Biacore™ assay.

The nucleotide and amino acid sequences of the variable regions of the CHIR-12.12 antibody are provided herein. More particularly, the amino acid sequences for the leader, variable, and constant regions for the light chain and heavy chain for mAb CHIR-12.12 are set forth in SEQ ID NO:2 (complete sequence for the light chain of mAb CHIR-12.12), SEQ ID NO:4 (complete sequence for the heavy chain for mAb CHIR-12.12), and SEQ ID NO:5 (complete sequence for a variant of the heavy chain for mAb CHIR-12.12 set forth in SEQ ID NO:4, where the variant comprises a serine substitution for the alanine residue at position 153 of SEQ ID NO:4). The nucleotide sequences encoding the light chain and heavy chain for mAb CHIR-12.12 are set forth in SEQ ID NO: 1 (coding sequence for the light chain for mAb CHIR-12.12) and SEQ ID NO:3 (coding sequence for the heavy chain for mAb CHIR-12.12). Hybridomas expressing the CHIR-12.12 antibody have been deposited with the ATCC with a patent deposit designation of PTA-5543.

Anti-CD40 antibodies for use in the methods of the present invention include antibodies differing from the CHIR-12.12 monoclonal antibody but retaining the CDRs, and antibodies with one or more amino acid addition(s), deletion(s), or substitution(s). The anti-CD40 antibodies for use in the methods of the present invention may also be de-immunized antibodies, particularly de-immunized antagonist anti-CD40 antibodies, which can be produced as described in, for example, International Publication Nos. WO 98/52976 and WO 0034317; herein incorporated by reference. In this manner, residues within the antagonist anti-CD40 antibodies of the invention are modified so as to render the antibodies non- or less immunogenic to humans while retaining their antagonist activity toward human CD40-expressing cells, wherein such activity is measured by assays noted elsewhere herein. Also included within the scope of the present invention are fusion proteins comprising an antibody of interest, for example, an antagonist anti-CD40 antibody or an antagonist anti-CD40L antibody, or a fragment thereof, which fusion proteins can be synthesized or expressed from corresponding polynucleotide vectors, as is known in the art. Such fusion proteins are described with reference to conjugation of antibodies as noted elsewhere herein.

Any known antibody having the binding specificity of interest can have sequence variations produced using methods described in, for example, Patent Publication Nos. EP 0983303 A1, WO 00/34317, and WO 98/52976, incorporated herein by reference. For example, it has been shown that sequences within the CDR can cause an antibody to bind to MHC Class II and trigger an unwanted helper T-cell response.

A conservative substitution can allow the antibody to retain binding activity yet lose its ability to trigger an unwanted T-cell response. Any such conservative or non-conservative substitutions can be made using art-recognized methods, such as those noted elsewhere herein, and the resulting antibodies can also be used in the methods of the present invention. The variant antibodies can be routinely tested for the particular activity, for example, antagonist activity, affinity, and specificity using methods described herein.

For example, amino acid sequence variants of an antagonist anti-CD40 antibody, for example, the CHIR-12.12 monoclonal antibody, can be prepared by mutations in the cloned DNA sequence encoding the antibody of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of an antibody of interest, for example, an antagonist anti-CD40 antibody polypeptide of interest, modifications are made such that variants continue to possess the desired activity, i.e., similar binding affinity and, in the case of antagonist anti-CD40 antibodies, are capable of specifically binding to a human CD40 antigen expressed on the surface of a human cell, and being free of significant agonist activity but exhibiting antagonist activity when bound to a CD40 antigen on a human CD40-expressing cell. Obviously, any mutations made in the DNA encoding the variant polypeptide must not place the sequence out of reading frame and preferably will not create complementary regions that could produce secondary mRNA structure. See EP patent application Publication No. 75,444.

In addition, the constant region of an antibody, for example, an antagonist anti-CD40 antibody, can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference antibody, for example, an antagonist anti-CD40 antibody, have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody, for example, an antagonist anti-CD40 antibody molecule, for example, the CHIR-12.12 monoclonal antibody described herein, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antibody, for example, an antagonist anti-CD40 antibody, by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

The precise chemical structure of a polypeptide capable of specifically binding CD40 and retaining antagonist activity, particularly when bound to CD40 antigen on malignant B cells, depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of antagonist anti-CD40 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CD40 antibody used herein so long as the antagonist properties of the anti-CD40 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy antagonist activity do not remove the polypeptide sequence from the definition of anti-CD40 antibodies of interest as used herein.

The art provides substantial guidance regarding the preparation and use of polypeptide variants. In preparing the anti-CD40 antibody variants, one of skill in the art can readily determine which modifications to the native protein nucleotide or amino acid sequence will result in a variant that is suitable for use as a therapeutically active component of a pharmaceutical composition used in the methods of the present invention.

The anti-CD40 antibody for use in the methods of the invention preferably possesses at least one of the following biological activities in vitro and/or in vivo: inhibition of immunoglobulin secretion by normal human peripheral B cells stimulated by T cells; inhibition of survival and/or proliferation of normal human peripheral B cells stimulated by CD40L-expressing cells or soluble CD40 ligand (sCD40L); inhibition of survival and/or proliferation of normal human peripheral B cells stimulated by Jurkat T cells; inhibition of "survival" anti-apoptotic intracellular signals in any cell stimulated by sCD40L or solid-phase CD40L; and, inhibition of CD40 signal transduction in any cell upon ligation with sCD40L or solid-phase CD40L, deletion, anergy and/or tolerance induction of CD40-bearing target cells or cells bearing cognate ligands to CD40 including, but not limited to, T cells and B cells, induction of expansion or activation of CD4$^+$ CD25$^+$ regulatory T cells (see for example, donor alloantigen-specific tissue rejection via CD40-CD40L interference, van Maurik et al. (2002) *J. Immunol.* 169:5401-5404), cytotoxicity via any mechanism (including, but not limited to, antibody-dependent cell-mediated cytotoxicity (ADCC), complement-dependent cytotoxicity (CDC), down-regulation of proliferation, and/or apoptosis in target cells), modulation of target cell cytokine secretion and/or cell surface molecule expression, and combinations thereof.

Assays for such biological activities can be performed as described herein and in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337 (035784/258442)), 60/525,579 (035784/271525)), and 60/565,710 (035784/277214)), respectively; and International Patent Application No. PCT/US2004/037152 (035784/282916)), published as WO 2005/044854, also entitled "*Antagonist Anti-CD40 Monoclonal Antibodies and Methods for Their Use,*" filed Nov. 4, 2004; the contents of each of which are herein incorporated by reference in their entirety. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

A representative assay to detect antagonist anti-CD40 antibodies specific to the CD40-antigen epitopes identified herein is a "competitive binding assay." Competitive binding assays are serological assays in which unknowns are detected and quantitated by their ability to inhibit the binding of a labeled known ligand to its specific antibody. This is also referred to as a competitive inhibition assay. In a representative competitive binding assay, labeled CD40 polypeptide is precipitated by candidate antibodies in a sample, for example, in combination with monoclonal antibodies raised against one or more epitopes of the monoclonal antibodies of the invention. Anti-CD40 antibodies that specifically react with an epitope of interest can be identified by screening a series of antibodies prepared against a CD40 protein or fragment of the protein comprising the particular epitope of the CD40 protein of interest. For example, for human CD40, epitopes of interest include epitopes comprising linear and/or nonlinear amino acid residues of the short isoform of human CD40 (see GenBank Accession No. NP_690593) set forth in SEQ ID NO: 10, encoded by the sequence set forth SEQ ID NO:9; see also GenBank Accession No. NM_152854), or of the long isoform of human CD40 (see GenBank Accession Nos. CAA43045 and NP_001241, set forth in SEQ ID NO:12, encoded by the sequence set forth in SEQ ID NO: 11; see GenBank Accession Nos. X60592 and NM_001250). Alternatively, competitive binding assays with previously identified suitable antagonist anti-CD40 antibodies could be used to select monoclonal antibodies comparable to the previously identified antibodies.

Antibodies employed in such immunoassays may be labeled or unlabeled. Unlabeled antibodies may be employed in agglutination; labeled antibodies may be employed in a wide variety of assays, employing a wide variety of labels. Detection of the formation of an antibody-antigen complex between an anti-CD40 antibody and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

It is also possible to engineer an antibody to have increased ADCC activity. In particular, the carboxy-terminal half of the CH2 domain is critical to ADCC mediated through the FcRIII receptor. Since the CH$_2$ and hinge regions have an important role in effector functions, a series of multiple-domain antibodies that contain extra CH2 and/or hinge regions may be created and investigated for any changes in effector potency (see Greenwood, J., Gorman, S. D., Routledge, E. G., Lloyd, I. S. & Waldmann, H., Ther Immunol. 1994 October; 1(5): 247-55). An alternative approach may be to engineer extra domains in parallel, for example, through creation of dimers by engineering a cysteine into the H-chain of a chimeric Ig (see Shopes B. (1992) *J. Immunol.* 1992 1; 148(9): 2918-22). Furthermore, changes to increase ADCC activity may be engineered by introducing mutations into the Fc region (see, for example, U.S. Pat. No. 6,737,056 B1), expressing cells in fucosyl transferase deficient cell lines (see, for example, US2003/0115614), or effecting other changes to antibody glycosylation (see, for example, U.S. Pat. No. 6,602,684).

The present invention is advantageous for the treatment of CD40 expressing cancers and pre-malignant conditions wherein a patient is homozygous or heterozygous for the FcγRIIIa-158F genotype.

As used herein, "anti-CD20 antibody" encompasses any antibody that specifically recognizes the CD20 cell surface antigen, including polyclonal antibodies, monoclonal antibodies, single-chain antibodies, and fragments thereof such as Fab, F(ab')$_2$, F$_v$, and other fragments that retain the antigen-binding function of the parent anti-CD20 antibody. Of particular interest in connection with the methods of the present invention are anti-CD20 antibodies or antigen-binding fragments thereof that have the binding properties exhibited by the IDEC-C2B8 monoclonal antibody (Biogen IDEC Inc., Cambridge, Mass.).

In some embodiments, the anti-CD40 antibodies used in the methods of the invention exhibit more potent therapeutic activity than the chimeric anti-CD20 monoclonal antibody IDEC-C2B8, where anti-tumor activity is assayed with equivalent amounts of these antibodies in a nude mouse xenograft tumor model using human lymphoma or myeloma cell lines. IDEC-C2B8 (IDEC Pharmaceuticals Corp., San Diego, Calif.; commercially available under the tradename Rituxan®, also referred to as rituximab) is a chimeric anti-CD20 monoclonal antibody containing human IgG1 and kappa constant regions with murine variable regions isolated from a murine anti-CD20 monoclonal antibody, IDEC-2B8 (Reff et al. (1994) *Blood* 83:435-445). Rituxan® is licensed for treatment of relapsed B cell low-grade or follicular non-Hodgkin's lymphoma (NHL). The discovery of antibodies with superior therapeutic, in particular anti-tumor, activity compared to Rituxan® could drastically improve methods of therapy for cancers and pre-malignant conditions, such as B cell lymphomas, particularly B cell non-Hodgkin's lymphoma.

Suitable nude mouse xenograft tumor models include those using the human Burkitt's lymphoma cell lines known as Namalwa and Daudi. Preferred embodiments assay anti-tumor activity in a staged nude mouse xenograft tumor model using the Daudi human lymphoma cell line as described herein below in Example 7. A staged nude mouse xenograft tumor model using the Daudi lymphoma cell line is more effective at distinguishing the therapeutic efficacy of a given antibody than is an unstaged model, as in the staged model antibody dosing is initiated only after the tumor has reached a measurable size. In the unstaged model, antibody dosing is initiated generally within about 1 day of tumor inoculation and before a palpable tumor is present. The ability of an antibody to outperform Rituxan® (i.e., to exhibit increased therapeutic activity) in a staged model is a strong indication that the antibody will be more therapeutically effective than Rituxan®. Moreover, in the Daudi model, anti-CD20, the target for Rituxan® is expressed on the cell surface at a higher level than is CD40.

By "equivalent amount" of the anti-CD40 antibody of the invention and Rituxan® is intended the same mg dose is administered on a per weight basis. Thus, where the anti-CD40 antibody is dosed at 0.01 mg/kg body weight of the mouse used in the tumor model, Rituxan® is also dosed at 0.01 mg/kg body weight of the mouse. Similarly, where the anti-CD40 antibody is dosed at 0.1, 1, or 10 mg/kg body weight of the mouse used in the tumor model, the Rituxan® is also dosed at 0.1, 1, or 10 mg/kg, respectively, of the body weight of the mouse.

When administered in the nude mouse xenograft tumor model, some anti-CD40 antibodies result in significantly less tumor volume than an equivalent amount of Rituxan®. For example, the fully human monoclonal antibody CHIR-12.12 exhibits at least a 20% increase in anti-tumor activity relative to that observed with an equivalent dose of Rituxan® when assayed in the staged nude mouse xenograft tumor model using the Daudi human lymphoma cell line in the manner described in Example 7 herein, and can exhibit as much as a 50% to 60% increase in anti-tumor activity in this assay. This increased anti-tumor activity is reflected in the greater reduction in tumor volume observed with the anti-CD40 antibody of the invention when compared to the equivalent dose of Rituxan® or in the induction of more complete responses. Thus, for example, depending upon the length of time after tumor inoculation, the monoclonal antibody CHIR-12.12 can exhibit a tumor volume that is about one-third to about one-half that observed for an equivalent dose of Rituxan®.

Another difference in antibody efficacy is to measure in vitro the concentration of antibody needed to obtain the maximum lysis of tumor cells in vitro in the presence of NK cells. For example, the anti-CD40 antibodies of the invention reach maximum lysis of Daudi cells at an EC50 of less than ½, and preferably ¼, and most preferably, 1/10 the concentration of Rituxan®. This type of measurement is also described in the Examples herein.

Anti-CD40 antibodies that benefit from having significantly greater efficacy than equivalent amounts of Rituxan® in the assays described above may include:

a) the monoclonal antibody CHIR-12.12;
b) the monoclonal antibody produced by the hybridoma cell line 12.12;
c) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5;
d) a monoclonal antibody having an amino acid sequence encoded by a nucleic acid molecule comprising a nucleotide sequence selected from the group consisting of the sequence shown in SEQ ID NO: 1, the sequence shown in SEQ ID NO:3, and both the sequences shown in SEQ ID NO: 1 and SEQ ID NO:3;
e) a monoclonal antibody that binds to an epitope capable of binding the monoclonal antibody produced by the hybridoma cell line 12.12;
f) a monoclonal antibody that binds to an epitope comprising residues 82-87 of the human CD40 sequence shown in SEQ ID NO:7 or SEQ ID NO:9;
g) a monoclonal antibody that binds to an epitope comprising residues 82-89 of the human CD40 sequence shown in SEQ ID NO:7 or SEQ ID NO:9;
h) a monoclonal antibody that competes with the monoclonal antibody CHIR-12.12 in a competitive binding assay;
i) the monoclonal antibody of preceding item a) or a monoclonal antibody of any one of preceding items c)-h), wherein said antibody is recombinantly produced; and
j) a monoclonal antibody that is an antigen-binding fragment of a monoclonal antibody of any one of preceding items a)-i), wherein said fragment retains the capability of specifically binding to human CD40 antigen.

The present invention provides a method for identifying a human patient with a cancer or pre-malignant condition treatable with an anti-CD40 antibody, comprising:

a) identifying a human patient with a cancer or pre-malignant condition that is associated with CD40-expressing cells; and b) determining said human patient's FcγRIIIa-158 genotype (V/V, V/F or
F/F);

wherein said cancer or pre-malignant condition is treatable with an anti-CD40 antibody if said human patient is heterozygous or homozygous for FcγRIIIa-158F (genotype V/F or F/F). The cancer or pre-malignant condition may be refractory to treatment with rituximab (Rituxan®).

Once a human patient with a cancer or pre-malignant condition treatable with an anti-CD40 antibody has been identified, that human patient can then be treated with an anti-CD40 antibody. Thus, the method may include the further step of (c) administering to a human patient identified as heterozygous or homozygous for FcγRIIIa-158F (genotype V/F or F/F) a therapeutically or prophylactically effective amount of an anti-CD40 antibody.

This method of identifying a human patient with a cancer or pre-malignant condition treatable with an anti-CD40 antibody can readily be performed by a person skilled in the art using a suitable diagnostic kit. The kit should comprise reagents suitable for determining a human patient's FcγRIIIa-158 genotype. Thus, the invention also provides a kit for identifying a human patient with a cancer or pre-malignant condition treatable with an anti-CD40 antibody, comprising reagents for determining a human patient's FcγRIIIa-158 genotype. Suitable kits are described in more detail elsewhere herein.

The invention also provides a method for selecting an antibody therapy for treatment of a human patient having a cancer or pre-malignant condition, comprising:

a) identifying a human patient having a cancer or pre-malignant condition that is associated with CD40-expressing cells; and b) determining said human patient's FcγRIIIa-158 genotype (V/V, V/F or F/F);

wherein if said human patient is heterozygous or homozygous for FcγRIIIa-158F (genotype V/F or F/F), an anti-CD40 antibody is selected for treatment of said cancer or pre-malignant condition. The cancer or pre-malignant condition may be refractory to treatment with rituximab (Rituxan®).

Once an anti-CD40 antibody therapy for treatment of a human patient having a cancer or pre-malignant condition has been selected, that human patient can then be treated with an anti-CD40 antibody. Thus, the method may include the further step of (c) administering to a human patient identified as heterozygous or homozygous for FcγRIIIa-158F (genotype V/F or F/F) a therapeutically or prophylactically effective amount of an anti-CD40 antibody.

This method of selecting an antibody therapy for treatment of a human patient having a cancer or pre-malignant condition can also readily be performed by a person skilled in the art using a suitable diagnostic kit. The kit should comprise reagents suitable for determining a human patient's FcγRIIIa-158 genotype. Thus, the invention also provides a kit for selecting an antibody therapy for treatment of a human patient having a cancer or pre-malignant condition associated with CD40-expressing cells, comprising reagents for determining a human patient's FcγRIIIa-158 genotype.

By "treatable with an anti-CD40 antibody" is intended the human patient (i.e., an individual with a cancer or pre-malignant condition), when treated with the anti-CD40 antibody, would benefit from a "positive therapeutic response" (as defined elsewhere herein) with respect to the cancer or pre-malignant condition for which treatment is sought.

Any method for determining a human patient's FcγRIIIa-158 genotype using a biological sample obtained from the human patient is contemplated.

For example, the invention provides a kit for use in determining a human patient's FcγRIIIa-158 genotype, which includes a microarray comprising at least one probe of 10 or more nucleotides in length and of a sequence suitable for determining a human patient's FcγRIIIa-158 genotype. Labeled RNA or DNA is hybridized to complementary probes on the array and then detected by laser scanning. Hybridization intensities for each probe on the array are determined and converted to a quantitative value representing relative gene expression levels. The selection of probe sequences and lengths can readily be performed by the skilled person. The nucleotide sequence of the human gene and mRNA encoding the FcγRIIIa-158 F and V allotypes is known. Thus, the skilled person can select probe(s) that, under the appropriate experimental conditions, allow a determination of the FcγRIIIa-158 genotype of the target sequences.

Techniques for the synthesis of these arrays using mechanical synthesis methods are described in, e.g., U.S. Pat. No. 5,384,261, incorporated herein by reference in its entirety. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation of an all-inclusive device. See, for example, U.S. Pat. Nos. 5,856, 174 and 5,922,591, herein incorporated by reference.

For example, the invention also provides a kit for use in determining a human patient's FcγRIIIa-158 genotype, comprising oligonucleotides suitable for use as primers in polymerase-catalysed amplification of the region of the gene or mRNA encoding amino acid 158 of FcγRIIIa. The selection of primer sequences and lengths can readily be performed by the skilled person. The nucleotide sequence of the human gene and mRNA encoding the FcγRIIIa-158 F and V allotypes is known. Thus, the skilled person can select primers which, under the appropriate experimental conditions, will allow amplification of the region of the gene or mRNA encoding amino acid 158 of FcγRIIIa. The amplified sequence can then be sequenced using known methods to determine the patient's FcγRIIIa-158 genotype.

Another method for determining a human patient's FcγRIIIa-158 genotype is to use a nucleic acid-based method that detects DNA fragmentation that is characteristic of the human patient's FcγRIIIa-158 genotype. When resolved using electrophoresis on agarose gels, DNA of each FcγRIIIa-158 genotype has a characteristic pattern. Thus, the invention also provides a kit for use in determining a human patient's FcγRIIIa-158 genotype, comprising one or more restriction enzymes suitable for determining a human patient's FcγRIIIa-158 genotype. Suitable restriction enzymes are known in the art (for example, see Koene et al. (1997) *Blood* 90(3):1109-1114).

The kits of the invention may also include instructions which indicate how to use the kit to determine a human patient's FcγRIIIa-158 genotype. The kit can also comprise, e.g., a buffering agent, a preservative, or a protein stabilizing agent. Each component of the kit is usually enclosed within an individual container, and all of the various containers are within a single package along with instructions which indicate how to use the kit to determine a human patient's FcγRIIIa-158 genotype.

The invention provides the use of anti-CD40 antibodies in the manufacture of medicaments for treating a cancer or pre-malignant condition associated with CD40-expressing cells, as described elsewhere herein.

The anti-CD40 antibodies of this invention are administered at a concentration that is therapeutically effective to prevent or treat a cancer or pre-malignant condition associated with CD40-expressing cells. To accomplish this goal, the antibodies may be formulated using a variety of acceptable carrier and/or excipients known in the art. The anti-CD40 antibody may be administered by a parenteral route of administration. Typically, the antibodies are administered by injection, either intravenously or subcutaneously. Methods to accomplish this administration are known to those of ordinary skill in the art.

Intravenous administration occurs preferably by infusion over a period of about less than 1 hour to about 10 hours (less than 1, 2, 3, 4, 5, 6, 7, 8, 9, or 10 hours). Subsequent infusions may be administered over a period of about less than 1 to about 6 hours, including, for example, about 1 to about 4 hours, about 1 to about 3 hours, or about 1 to about 2 hours or less than an hour. Alternatively, a dose can be administered subcutaneously.

A pharmaceutical composition of the invention is formulated to be compatible with its intended route of administration. Solutions or suspensions used for parenteral application can include the following components: a sterile diluent such as water for injection, saline solution; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The anti-CD40 antibodies are typically provided by standard technique within a pharmaceutically acceptable buffer, for example, sterile saline, sterile buffered water, combinations of the foregoing, etc. Methods for preparing parenterally administrable agents are described in *Remington's Pharmaceutical Sciences* (18$^{th}$ ed.; Mack Publishing Company, Eaton, Pa., 1990), herein incorporated by reference. See also, for example, WO 98/56418, which describes stabilized antibody pharmaceutical formulations suitable for use in the methods of the present invention.

The amount of at least one anti-CD40 antibody to be administered is readily determined by one of ordinary skill. Factors influencing the mode of administration and the respective amount of at least one anti-CD40 antibody include, but are not limited to, the severity of the disease, the history of the disease, and the age, height, weight, health, type of disease, and physical condition of the individual undergoing therapy or response to antibody infusion. Similarly, the amount of anti-CD40 antibody to be administered will be dependent upon the mode of administration and whether the subject will undergo a single dose or multiple doses of this anti-tumor agent. Generally, a higher dosage of anti-CD40 antibody is preferred with increasing weight of the subject undergoing therapy.

For a single dose of anti-CD40 antibody to be administered is in the range from about 0.3 mg/kg to about 50 mg/kg, from about 0.1 mg/kg to about 40 mg/kg, from about 0.01 mg/kg to about 30 mg/kg, from about 0.1 mg/kg to about 30 mg/kg, from about 0.5 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg.

Thus, for example, the dose can be 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg, or other such doses falling within the range of about 0.3 mg/kg to about 50 mg/kg.

Treatment of a subject with a therapeutically effective amount of an antibody can include a single treatment or, preferably, can include a series of treatments. Thus, in another embodiment of the invention, the method comprises administration of multiple doses of anti-CD40 antibody. The method may comprise administration of 1, 2, 3, 4, 5, 6, 7, 8, 9, 10, 15, 20, 25, 30, 35, 40, or more therapeutically effective doses of a pharmaceutical composition comprising an anti-CD40 antibody. The frequency and duration of administration of multiple doses of the pharmaceutical compositions comprising anti-CD40 antibody can be readily determined by one of skill in the art without undue experimentation. The same therapeutically effective dose of an anti-CD40 antibody can be administered over the course of a treatment period. Alternatively, different therapeutically effective doses of an anti-CD40 antibody can be used over the course of a treatment period.

In an example, a subject is treated with anti-CD40 antibody in the range of between about 0.1 to 20 mg/kg body weight, once per week for between about 1 to 10 weeks, preferably between about 2 to 8 weeks, more preferably between about 3 to 7 weeks, and even more preferably for about 4, 5, or 6 weeks. Treatment may occur at intervals of every 2 to 12 months to prevent relapse or upon indication of relapse. It will also be appreciated that the effective dosage of antibody used for treatment may increase or decrease over the course of a particular treatment. Changes in dosage may result and become apparent from the results of diagnostic assays as described herein.

Thus, in one embodiment, the dosing regimen includes a first administration of a therapeutically effective dose of at least one anti-CD40 antibody on days 1, 8, 15, and 22 of a treatment period.

In another embodiment, the dosing regimen includes a dosing regimen having a first administration of a therapeutically effective dose of at least one anti-CD40 antibody daily, or on days 1, 3, 5, and 7 of a week in a treatment period; a dosing regimen including a first administration of a therapeutically effective dose of at least one anti-CD40 antibody on days 1 and 3-4 of a week in a treatment period; and a preferred dosing regimen including a first administration of a therapeutically effective dose of at least one anti-CD40 antibody on day 1 of a week in a treatment period. The treatment period may comprise 1 week, 2 weeks, 3 weeks, a month, 2 months, 3 months, 6 months, or a year. Treatment periods may be subsequent or separated from each other by a week, 2 weeks, a month, 3 months, 6 months, or a year.

In other embodiments, the initial therapeutically effective dose of an anti-CD40 antibody as defined elsewhere herein can be in the lower dosing range (i.e., about 0.3 mg/kg to about 20 mg/kg) with subsequent doses falling within the higher dosing range (i.e., from about 20 mg/kg to about 50 mg/kg).

In alternative embodiments, the initial therapeutically effective dose of an anti-CD40 antibody as defined elsewhere herein can be in the upper dosing range (i.e., about 20 mg/kg to about 50 mg/kg) with subsequent doses falling within the lower dosing range (i.e., 0.3 mg/kg to about 20 mg/kg). Thus, in some embodiments of the invention, anti-CD40 antibody therapy may be initiated by administering a "loading dose" of the antibody to the subject in need therapy. By "loading dose" is intended an initial dose of the anti-CD40 antibody that is administered to the subject, where the dose of the antibody administered falls within the higher dosing range (i.e., from about 20 mg/kg to about 50 mg/kg). The "loading dose" can be administered as a single administration, for example, a single infusion where the antibody is administered IV, or as multiple administrations, for example, multiple infusions where the antibody is administered IV, so long as the complete "loading dose" is administered within about a 24-hour period. Following administration of the "loading dose," the subject is then administered one or more additional therapeutically effective doses of the anti-CD40 antibody. Subsequent therapeutically effective doses can be administered, for example, according to a weekly dosing schedule, or once every two weeks, once every three weeks, or once every four weeks. In such embodiments, the subsequent therapeutically effective doses generally fall within the lower dosing range (i.e., 0.3 mg/kg to about 20 mg/kg).

Alternatively, in some embodiments, following the "loading dose", the subsequent therapeutically effective doses of the anti-CD40 antibody are administered according to a "maintenance schedule," wherein the therapeutically effective dose of the antibody is administered once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the anti-CD40 antibody fall within the lower dosing range (i.e., 0.003 mg/kg to about 20 mg/kg), particularly when the subsequent doses are administered at more frequent intervals, for example, once every two weeks to once every month, or within the higher dosing range (i.e., from about 20 mg/kg to about 50 mg/kg), particularly when the subsequent doses are administered at less frequent intervals, for example, where subsequent doses are administered about one month to about 12 months apart.

The anti-CD40 antibodies present in the pharmaceutical compositions described herein for use in the methods of the invention may be native or obtained by recombinant techniques, and may be from any source, including mammalian sources such as, e.g., mouse, rat, rabbit, primate, pig, and human. Preferably such polypeptides are derived from a human source, and more preferably are recombinant, human proteins from hybridoma cell lines.

The pharmaceutical compositions useful in the methods of the invention may comprise biologically active variants of the antagonist anti-CD40 antibodies of the invention, as described elsewhere herein.

Any pharmaceutical composition comprising an anti-CD40 antibody having the binding properties described herein as the therapeutically active component can be used in the methods of the invention. Thus liquid, lyophilized, or spray-dried compositions comprising one or more of the anti-CD40 antibodies may be prepared as an aqueous or nonaqueous solution or suspension for subsequent administration to a subject in accordance with the methods of the invention. Each of these compositions will comprise at least one anti-CD40 antibody as a therapeutically or prophylactically active component. By "therapeutically or prophylactically active component" is intended the anti-CD40 antibody is specifically incorporated into the composition to bring about a desired therapeutic or prophylactic response with regard to treatment, prevention, or diagnosis of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

Formulants may be added to pharmaceutical compositions comprising an anti-CD40 antibody of the invention. These formulants may include, but are not limited to, oils, polymers, vitamins, carbohydrates, amine acids, salts, buffers, albumin, surfactants, or bulking agents. Preferably carbohydrates include sugar or sugar alcohols such as mono-, di-, or polysaccharides, or water soluble glucans. The saccharides or glucans can include fructose, glucose, mannose, sorbose, xylose, maltose, sucrose, dextran, pullulan, dextrin, α and β cyclodextrin, soluble starch, hydroxyethyl starch, and carboxymethylcellulose, or mixtures thereof. "Sugar alcohol" is defined as a $C_4$ to $C_8$ hydrocarbon having a hydroxyl group and includes galactitol, inositol, mannitol, xylitol, sorbitol, glycerol, and arabitol. These sugars or sugar alcohols may be used individually or in combination. The sugar or sugar alcohol concentration is between 1.0% and 7% w/v., more preferably between 2.0% and 6.0% w/v. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. Surfactants that can be added to the formulation are shown in EP Nos. 270,799 and 268,110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546; which are all hereby incorporated by reference in their entireties. Preferred polymers are polyoxyethylated polyols and polyethylene glycol (PEG). PEG is soluble in water at room temperature and has the general formula: $R(O-CH_2-CH_2)_n O-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al. (1988) *J. Bio. Chem.* 263:15064-15070, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al. (1982) *Cancer Research* 42:4734; Cafiso (1981) *Biochem Biophys Acta* 649:129; and Szoka (1980) *Ann. Rev. Biophys. Eng.* 9:467. Other drug delivery systems are known in the art and are described in, e.g., Poznansky et al. (1980) *Drug Delivery Systems* (R. L. Juliano, ed., Oxford, N.Y.) pp. 253-315; Poznansky (1984) Pharm Revs 36:277.

The formulants to be incorporated into a pharmaceutical composition should provide for the stability of the anti-CD40 antibody. That is, the anti-CD40 antibody should retain its physical and/or chemical stability and have the desired biological activity, i.e., one or more of the antagonist activities defined herein above, including, but not limited to, inhibition of immunoglobulin secretion by normal human peripheral B cells stimulated by T cells; inhibition of survival and/or proliferation of normal human peripheral B cells stimulated by Jurkat T cells; inhibition of survival and/or proliferation of normal human peripheral B cells stimulated by CD40L-expressing cells or soluble CD40 ligand (sCD40L); inhibition of "survival" anti-apoptotic intracellular signals in any cell stimulated by sCD40L or solid-phase CD40L; inhibition of CD40 signal transduction in any cell upon ligation with sCD40L or solid-phase CD40L; and inhibition of proliferation of human malignant B cells as noted elsewhere herein.

Methods for monitoring protein stability are well known in the art. See, for example, Jones (1993) *Adv. Drug Delivery Rev.* 10:29-90; Lee, ed. (1991) *Peptide and Protein Drug Delivery* (Marcel Dekker, Inc., New York, N.Y.); and the stability assays disclosed herein below. Generally, protein stability is measured at a chosen temperature for a specified period of time. In preferred embodiments, a stable antibody pharmaceutical formulation provides for stability of the anti-CD40 antibody when stored at room temperature (about 25° C.) for at least 1 month, at least 3 months, or at least 6 months, and/or is stable at about 2-8° C. for at least 6 months, at least 9 months, at least 12 months, at least 18 months, at least 24 months.

A protein such as an antibody, when formulated in a pharmaceutical composition, is considered to retain its physical stability at a given point in time if it shows no visual signs (i.e., discoloration or loss of clarity) or measurable signs (for example, using size-exclusion chromatography (SEC) or UV light scattering) of precipitation, aggregation, and/or denaturation in that pharmaceutical composition. With respect to chemical stability, a protein such as an antibody, when formulated in a pharmaceutical composition, is considered to retain its chemical stability at a given point in time if measurements of chemical stability are indicative that the protein (i.e., antibody) retains the biological activity of interest in that pharmaceutical composition. Methods for monitoring changes in chemical stability are well known in the art and include, but are not limited to, methods to detect chemically altered forms of the protein such as result from clipping, using, for example, SDS-PAGE, SEC, and/or matrix-assisted laser desorption ionization/time of flight mass spectrometry; and degradation associated with changes in molecular charge (for example, associated with deamidation), using, for example, ion-exchange chromatography. See, for example, the methods disclosed herein below.

An anti-CD40 antibody, when formulated in a pharmaceutical composition, is considered to retain a desired biological activity at a given point in time if the desired biological activity at that time is within about 30%, preferably within about 20% of the desired biological activity exhibited at the time the pharmaceutical composition was prepared as determined in a suitable assay for the desired biological activity. Assays for measuring the desired biological activity of the anti-CD40 antibodies can be performed as described in the Examples herein. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

In some embodiments of the invention, the anti-CD40 antibody is formulated in a liquid pharmaceutical formulation. The anti-CD40 antibody can be prepared using any method known in the art, including those methods disclosed herein above. In one embodiment, the anti-CD40 antibody is recombinantly produced in a CHO cell line.

Where the anti-CD40 antibody is to be stored prior to its formulation, it can be frozen, for example, at ≤−20° C., and then thawed at room temperature for further formulation. The liquid pharmaceutical formulation comprises a therapeutically effective amount of the anti-CD40 antibody. The amount of antibody thereof present in the formulation takes into consideration the route of administration and desired dose volume.

In this manner, the liquid pharmaceutical composition comprises the anti-CD40 antibody at a concentration of about 0.1 mg/ml to about 50.0 mg/ml, about 0.5 mg/ml to about 40.0 mg/ml, about 1.0 mg/ml to about 30.0 mg/ml, about 5.0 mg/ml to about 25.0 mg/ml, about 5.0 mg/ml to about 20.0 mg/ml, or about 15.0 mg/ml to about 25.0 mg/ml. In some embodiments, the liquid pharmaceutical composition comprises the anti-CD40 antibody at a concentration of about 0.1 mg/ml to about 5.0 mg/ml, about 5.0 mg/ml to about 10.0 mg/ml, about 10.0 mg/ml to about 15.0 mg/ml, about 15.0 mg/ml to about 20.0 mg/ml, about 20.0 mg/ml to about 25.0 mg/ml, about 25.0 mg/ml to about 30.0 mg/ml, about 30.0 mg/ml to about 35.0 mg/ml, about 35.0 mg/ml to about 40.0 mg/ml, about 40.0 mg/ml to about 45.0 mg/ml, or about 45.0 mg/ml to about 50.0 mg/ml. In other embodiments, the liquid pharmaceutical composition comprises the anti-CD40 antibody at a concentration of about 15.0 mg/ml, about 16.0 mg/ml, about 17.0 mg/ml, about 18.0 mg/ml, about 19.0 mg/ml, about 20.0 mg/ml, about 21.0 mg/ml, about 22.0 mg/ml, about 23.0 mg/ml, about 24.0 mg/ml, or about 25.0 mg/ml. The liquid pharmaceutical composition comprises the anti-CD40 antibody and a buffer that maintains the pH of the formulation in the range of about pH 5.0 to about pH 7.0, including about pH 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and other such values within the range of about pH 5.0 to about pH 7.0. In some embodiments, the buffer maintains the pH of the formulation in the range of about pH 5.0 to about pH 6.5, about pH 5.0 to about pH 6.0, about pH 5.0 to about pH 5.5, about pH 5.5 to about 7.0, about pH 5.5 to about pH 6.5, or about pH 5.5 to about pH 6.0.

Any suitable buffer that maintains the pH of the liquid anti-CD40 antibody formulation in the range of about pH 5.0 to about pH 7.0 can be used in the formulation, so long as the physicochemical stability and desired biological activity of the antibody are retained as noted herein above. Suitable buffers include, but are not limited to, conventional acids and salts thereof, where the counter ion can be, for example, sodium, potassium, ammonium, calcium, or magnesium. Examples of conventional acids and salts thereof that can be used to buffer the pharmaceutical liquid formulation include, but are not limited to, succinic acid or succinate, citric acid or citrate, acetic acid or acetate, tartaric acid or tartarate, phosphoric acid or phosphate, gluconic acid or gluconate, glutamic acid or glutamate, aspartic acid or aspartate, maleic acid or maleate, and malic acid or malate buffers. The buffer concentration within the formulation can be from about 1 mM to about 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of about 1 mM to about 50 mM. In some embodiments, the buffer concentration within the formulation is from about 5 mM to about 15 mM, including about 5 mM, 6 mM, 7 mM, 8 mM, 9 mM, 10 mM, 11 mM, 12 mM, 13 mM, 14 mM, 15 mM, or other such values within the range of about 5 mM to about 15 mM.

In some embodiments of the invention, the liquid pharmaceutical formulation comprises a therapeutically effective amount of the anti-CD40 antibody and succinate buffer or citrate buffer at a concentration that maintains the pH of the formulation in the range of about pH 5.0 to about pH 7.0, preferably about pH 5.0 to about pH 6.5. By "succinate buffer" or "citrate buffer" is intended a buffer comprising a salt of succinic acid or a salt of citric acid, respectively. In a preferred embodiment, the succinate or citrate counterion is the sodium cation, and thus the buffer is sodium succinate or sodium citrate, respectively. However, any cation is expected to be effective. Other possible succinate or citrate cations include, but are not limited to, potassium, ammonium, calcium, and magnesium. As noted above, the succinate or citrate buffer concentration within the formulation can be from about 1 mM to about 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of about 1 mM to about 50 mM. In some embodiments, the buffer concentration within the formulation is from about 5 mM to about 15 mM, including about 5 mM, 6 mM, 7 mM, 8 mM, 9 mM, 10 mM, 11 mM, 12 mM, 13 mM, 14 mM, or about 15 mM. In other embodiments, the liquid pharmaceutical formulation comprises the anti-CD40 antibody at a concentration of about 0.1 mg/ml to about 50.0 mg/ml, or about 5.0 mg/ml to about 25.0 mg/ml, and succinate or citrate buffer, for example, sodium succinate or sodium citrate buffer, at a concentration of about 1 mM to about 20 mM, about 5 mM to about 15 mM, preferably about 10 mM.

Where it is desirable for the liquid pharmaceutical formulation to be near isotonic, the liquid pharmaceutical formulation comprising the anti-CD40 antibody and a buffer can further comprise an amount of an isotonizing agent sufficient to render the formulation near isotonic. By "near isotonic" is intended the aqueous formulation has an osmolarity of about 240 mmol/kg to about 360 mmol/kg, preferably about 240 to about 340 mmol/kg, more preferably about 250 to about 330 mmol/kg, even more preferably about 260 to about 320 mmol/kg, still more preferably about 270 to about 310 mmol/kg. Methods of determining the isotonicity of a solution are known to those skilled in the art. See, for example, Setnikar et al. (1959) *J. Am. Pharm. Assoc.* 48:628.

Those skilled in the art are familiar with a variety of pharmaceutically acceptable solutes useful in providing isotonicity in pharmaceutical compositions. The isotonizing agent can be any reagent capable of adjusting the osmotic pressure of the liquid pharmaceutical formulation of the present invention to a value nearly equal to that of a body fluid. It is desirable to use a physiologically acceptable isotonizing agent. Thus, the liquid pharmaceutical formulation comprising a therapeutically effective amount of the anti-CD40 antibody and a buffer can further comprise components that can be used to provide isotonicity, for example, sodium chloride; amino acids such as alanine, valine, and glycine; sugars and sugar alcohols (polyols), including, but not limited to, glucose, dextrose, fructose, sucrose, maltose, mannitol, trehalose, glycerol, sorbitol, and xylitol; acetic acid, other organic acids or their salts, and relatively minor amounts of citrates or phosphates. The ordinary skilled person would know of additional agents that are suitable for providing optimal tonicity of the liquid formulation.

In some preferred embodiments, the liquid pharmaceutical formulation comprising an anti-CD40 antibody and a buffer further comprises sodium chloride as the isotonizing agent. The concentration of sodium chloride in the formulation will depend upon the contribution of other components to tonicity. In some embodiments, the concentration of sodium chloride is about 50 mM to about 300 mM, about 50 mM to about 250 mM, about 50 mM to about 200 mM, about 50 mM to about 175 mM, about 50 mM to about 150 mM, about 75 mM to about 175 mM, about 75 mM to about 150 mM, about 100 mM to about 175 mM, about 100 mM to about 200 mM, about 100 mM to about 150 mM, about 125 mM to about 175 mM, about 125 mM to about 150 mM, about 130 mM to about 170 mM, about 130 mM to about 160 mM, about 135 mM to about 155 mM, about 140 mM to about 155 mM, or about 145 mM to about 155 mM. In one such embodiment, the concentration of sodium chloride is about 150 mM. In other such embodiments, the concentration of sodium chloride is about 150 mM, the buffer is sodium succinate or sodium citrate buffer at a concentration of about 5 mM to about 15 mM, the liquid pharmaceutical formulation comprises a therapeutically effective amount of the anti-CD40 antibody and the formulation has a pH of about pH 5.0 to about pH 7.0, about pH 5.0 to about pH 6.0, or about pH 5.5 to about pH 6.5. In other embodiments, the liquid pharmaceutical formulation comprises the anti-CD40 antibody at a concentration of about 0.1 mg/ml to about 50.0 mg/ml or about 5.0 mg/ml to about 25.0 mg/ml, about 150 mM sodium chloride, and about 10 mM sodium succinate or sodium citrate, at a pH of about pH 5.5.

Protein degradation due to freeze thawing or mechanical shearing during processing of a liquid pharmaceutical formulations of the present invention can be inhibited by incorporation of surfactants into the formulation in order to lower the surface tension at the solution-air interface. Thus, in some embodiments, the liquid pharmaceutical formulation comprises a therapeutically effective amount of the anti-CD40 antibody, a buffer, and further comprises a surfactant. In other embodiments, the liquid pharmaceutical formulation comprises an anti-CD40 antibody, a buffer, an isotonizing agent, and further comprises a surfactant.

Typical surfactants employed are nonionic surfactants, including polyoxyethylene sorbitol esters such as polysorbate 80 (Tween® 80) and polysorbate 20 (Tween® 20) polyoxypropylene-polyoxyethylene esters such as Pluronic® F68; polyoxyethylene alcohols such as Brij 35; simethicone; polyethylene glycol such as PEG400; lysophosphatidylcholine; and polyoxyethylene-p-t-octylphenol such as Triton X-100. Classic stabilization of pharmaceuticals by surfactants or emulsifiers is described, for example, in Levine et al. (1991) *J Parenteral Sci. Technol.* 45(3):160-165, herein incorporated by reference. A preferred surfactant employed in the practice of the present invention is polysorbate 80. Where a surfactant is included, it is typically added in an amount from about 0.001% to about 1.0% (w/v), about 0.001% to about 0.5%, about 0.001% to about 0.4%, about 0.001% to about 0.3%, about 0.001% to about 0.2%, about 0.005% to about 0.5%, about 0.005% to about 0.2%, about 0.01% to about 0.5%, about 0.01% to about 0.2%, about 0.03% to about 0.5%, about 0.03% to about 0.3%, about 0.05% to about 0.5%, or about 0.05% to about 0.2%.

Thus, in some embodiments, the liquid pharmaceutical formulation comprises a therapeutically effective amount of the anti-CD40 antibody, the buffer is sodium succinate or sodium citrate buffer at a concentration of about 1 mM to about 50 mM, about 5 mM to about 25 mM, or about 5 mM to about 15 mM; the formulation has a pH of about pH 5.0 to about pH 7.0, about pH 5.0 to about pH 6.0, or about pH 5.5 to about pH 6.5; and the formulation further comprises a surfactant, for example, polysorbate 80, in an amount from about 0.001% to about 1.0% or about 0.001% to about 0.5%. Such formulations can optionally comprise an isotonizing agent, such as sodium chloride at a concentration of about 50 mM to about 300 mM, about 50 mM to about 200 mM, or about 50 mM to about 150 mM. In other embodiments, the liquid pharmaceutical formulation comprises the anti-CD40 antibody at a concentration of about 0.1 mg/ml to about 50.0 mg/ml or about 5.0 mg/ml to about 25.0 mg/ml, including about 20.0 mg/ml; about 50 mM to about 200 mM sodium chloride, including about 150 mM sodium chloride; sodium succinate or sodium citrate at about 5 mM to about 20 mM, including about 10 mM sodium succinate or sodium citrate; sodium chloride at a concentration of about 50 mM to about 200 mM, including about 150 mM; and optionally a surfactant, for example, polysorbate 80, in an amount from about 0.001% to about 1.0%, including about 0.001% to about 0.5%; where the liquid pharmaceutical formulation has a pH of about pH 5.0 to about pH 7.0, about pH 5.0 to about pH 6.0, about pH 5.0 to about pH 5.5, about pH 5.5 to about pH 6.5, or about pH 5.5 to about pH 6.0.

The liquid pharmaceutical formulation can be essentially free of any preservatives and other carriers, excipients, or stabilizers noted herein above. Alternatively, the formulation can include one or more preservatives, for example, antibacterial agents, pharmaceutically acceptable carriers, excipients, or stabilizers described herein above provided they do not adversely affect the physicochemical stability of the anti-CD40 antibody. Examples of acceptable carriers, excipients, and stabilizers include, but are not limited to, additional buffering agents, co-solvents, surfactants, antioxidants including ascorbic acid and methionine, chelating agents such as EDTA, metal complexes (for example, Zn-protein complexes), and biodegradable polymers such as polyesters. A thorough discussion of formulation and selection of pharmaceutically acceptable carriers, stabilizers, and isomolytes can be found in *Remington's Pharmaceutical Sciences* (18$^{th}$ ed.; Mack Publishing Company, Eaton, Pa., 1990), herein incorporated by reference.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, succinate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween®, polyethylene glycol (PEG), and Pluronics®.

Administration "in combination with" one or more further therapeutic agents includes simultaneous (concurrent) and consecutive administration in any order.

After the liquid pharmaceutical formulation or other pharmaceutical composition described herein is prepared, it can be lyophilized to prevent degradation. Methods for lyophilizing liquid compositions are known to those of ordinary skill in the art. Just prior to use, the composition may be reconstituted with a sterile diluent (Ringer's solution, distilled water, or sterile saline, for example) that may include additional ingredients. Upon reconstitution, the composition is preferably administered to subjects using those methods that are known to those skilled in the art.

In some embodiments, the anti-CD40 antibodies may be administered in combination with at least one other cancer therapy, including, but not limited to, surgery, radiation therapy, chemotherapy, cytokine therapy, or other monoclonal antibody intended for use in treatment of the solid tumor of interest, where the additional cancer therapy is administered prior to, during, or subsequent to the anti-CD40 antibody therapy. Thus, where the combined therapies comprise administration of an anti-CD40 antibody in combination with administration of another therapeutic agent, as with chemotherapy, cytokine therapy, or other monoclonal antibody, the methods of the invention encompass coadministration, using separate formulations or a single pharmaceutical formulation, and consecutive administration in either order, wherein preferably there is a time period where both (or all) active agents simultaneously exert their therapeutic activities. Where the methods of the present invention comprise combined therapeutic regimens, these therapies can be given simultaneously, i.e., the anti-CD40 antibody is administered concurrently or within the same time frame as the other cancer therapy (i.e., the therapies are going on concurrently, but the anti-CD40 antibody is not administered precisely at the same time as the other cancer therapy). Alternatively, the anti-CD40 antibody of the present invention may also be administered prior to or subsequent to the other cancer therapy. Sequential administration of the different cancer therapies may be performed regardless of whether the treated subject responds to the first course of therapy to decrease the possibility of remission or relapse. Where the combined therapies comprise administration of the anti-CD40 antibody in combination with administration of a cytotoxic agent, preferably the anti-CD40 is administered prior to administering the cytotoxic agent.

In this manner, the anti-CD40 antibodies are administered in combination with at least one other cancer therapy, including, but not limited to, surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/I-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, and IL-21 therapy; steroid therapy; or other cancer therapy; where the additional cancer therapy is administered prior to, during, or subsequent to the antagonist anti-CD40 antibody therapy.

In one embodiment, the anti-CD40 antibodies are administered in combination with bortezomib (VELCADE®), in particular for the treatment of multiple myeloma. WO 2005/044855 A2 discloses that combining CHIR-12.12 with bortezomib treatment increases the efficacy of inhibition of tumor growth in experimental multiple myeloma models.

In one embodiment, the anti-CD40 antibodies are administered in combination with IL-2, in particular for the treatment of B cell lymphoma. WO 2005/044294 A2 discloses that combining CHIR-12.12 with IL-2 treatment resulted in additive anti-tumor activity against Namalwa tumors.

Thus, the invention provides the use of a therapeutically or prophylactically effective amount of an anti-CD40 antibody in the manufacture of a medicament for the treatment of a cancer or pre-malignant condition that is associated with CD40-expressing cells in a human patient heterozygous or homozygous for FcγRIIIa-158F (genotype V/F or F/F), wherein the medicament is coordinated with treatment with at least one other cancer therapy.

By "coordinated" is intended the medicament comprising the anti-CD40 antibody is to be used either prior to, during, or after treatment of the subject with at least one other cancer therapy.

The invention also provides for the use of an anti-CD40 antibody in the manufacture of a medicament for treating a human patient for a cancer or pre-malignant condition that is associated with CD40-expressing cells, wherein said human patient is heterozygous or homozygous for FcγRIIIa-158F (genotype V/F or F/F) and has been pretreated with at least one other oncotherapeutic.

By "pretreated" or "pretreatment" is intended the subject has received one or more other cancer therapies (i.e., been treated with at least one other cancer therapy) prior to receiving the medicament comprising the anti-CD40 antibody. "Pretreated" or "pretreatment" includes subjects that have been treated with at least one other cancer therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-CD40 antibody. It is not necessary that the subject was a responder to pretreatment with the prior cancer therapy, or prior cancer therapies. Thus, the subject that receives the medicament comprising the antagonist anti-CD40 antibody could have responded, or could have failed to respond (i.e. the cancer was refractory), to pretreatment with the prior cancer therapy, or to one or more of the prior cancer therapies where pretreatment comprised multiple cancer therapies. Examples of other cancer therapies for which a subject can have received pretreatment prior to receiving the medicament comprising the anti-CD40 antibody include, but are not limited to, surgery; radiation therapy; chemotherapy, optionally in combination with autologous bone marrow transplant, where suitable chemotherapeutic agents include, but are not limited to, those described herein and in WO 2005/044854, WO 2005/044304, WO 2005/044305, WO 2005/044306, WO 2005/044855, WO 2005/044307, and WO 2005/044294; other anti-cancer monoclonal antibody therapy, including, but not limited to, those anti-cancer antibodies described herein and in WO 2005/044854, WO 2005/044304, WO 2005/044305, WO 2005/044306, WO 2005/044855, WO 2005/044307, and WO 2005/044294; small molecule-based cancer therapy, including, but not limited to, the small molecules described herein and in WO 2005/044854, WO 2005/044304, WO 2005/044305, WO 2005/044306, WO 2005/044855, WO 2005/044307, and WO 2005/044294; vaccine/immunotherapy-based cancer therapies, including, but not limited to, those described herein and in WO 2005/044854, WO 2005/044304, WO 2005/044305, WO 2005/044306, WO 2005/044855, WO 2005/044307, and WO 2005/044294; steroid therapy; other cancer therapy; or any combination thereof.

"Treatment", in the context of coordinated use of an anti-CD40 antibody with one or more other cancer therapies, is herein defined as the application or administration of the anti-CD40 antibody or other cancer therapy to a patient, or application or administration to an isolated tissue or cell line from a patient, where the patient has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the application or administration of a pharmaceutical composition comprising the anti-CD40 antibody or other cancer therapy to a patient, or application or administration of a pharmaceutical composition comprising the anti-CD40 antibody or other cancer therapy, to an isolated tissue or cell line from a patient, who has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

In some embodiments, the combination therapy provides a synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, for example, tumor growth, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Various aspects and embodiments of the present invention will now be described in more detail by way of example only. It will be appreciated that modification of detail may be made without departing from the scope of the invention.

EXPERIMENTAL

The anti-CD40 antibody used in the examples below is CHIR-12.12. The production, sequencing and characterisation of the CHIR-12.12 antibody is described in detail in the international patent applications published as WO 2005/044854, WO 2005/044304, WO 2005/044305, WO 2005/044306, WO 2005/044855, WO 2005/044307, and WO 2005/044294. Hybridoma line 153.8E2.D10.D6.12.12 (CMCC#12056) expressing the CHIR-12.12 antibody has been deposited with the American Type Culture Collection [ATCC; 10801 University Blvd., Manassas, Va. 20110-2209 (USA)] on Sep. 17, 2003, under Patent Deposit Number PTA-5543.

Example 1

Analysis of ADCC in Cell Lines

CHIR-12.12 and rituximab were compared for their relative ADCC activity against a variety of malignant B-cell lines expressing both CD40 and CD20 antigens, including lymphoma cell lines (Daudi, Namalwa), multiple myeloma cell lines (ARH77, IM-9), a B-ALL cell line (CCRF-SB), and a B-CLL cell line (EHEB).

The ADCC efficacy and potency measured as maximum percent lysis and ED50, respectively, were compared for CHIR-12.12 and rituximab. The results of these experiments are shown in FIGS. 1A-1F. For all target cell lines, CHIR-12.12 was a more potent and efficacious mediator of ADCC than rituximab. In the six cell lines tested, the number of cell surface CD20 molecules per cell were 2.6 to 30.8-fold higher than CD40. These data show that despite displaying fewer CD40 molecules than CD20, malignant B-cell lines are more effectively lysed by CHIR-12.12 than rituximab.

Example 2

Analysis of ADCC in CLL Patient Cells

The relative ADCC activity of CHIR-12.12 and rituximab against ex vivo primary CLL cells from 8 patients was compared. CHIR-12.12 exhibited greater ADCC than rituximab against CLL from all patients (see FIG. 2A-D and FIG. 3). The average percent maximum lysis by CHIR-12.12 and rituximab were 49±16% and 31±14%, respectively. CHIR-12.12 was greater than 10-fold more potent than rituximab, as measured by $ED_{50}$ values (14.1 pM versus 155.5 pM, respectively).

Antibody-Dependent Cellular Cytotoxicity (ADCC) Experiment Design

Target cells: CLL patient cells, 5000/well. Effector cells: purified normal human NK cells, 50,000/well. E:T ratio: 10. Abs concentration: 0.00001, 0.0001, 0.001, 0.01, 0.1, 1 and 10 µg/ml. Incubation time: 4 hrs. Culture medium: RPMI (w/o Phenol red)+10% FBS+1% P/S. Culture device: 96-well round bottom plate. Readout: Calcein AM release measured by Arbitrary Fluorescent Units (AFU) with 485 nm excitation/535 nm emission. Calculation: % specific lysis=100× (AFU test−AFU spontaneous release1)/(AFU maximal release2−AFU spontaneous). Negative control: Calcein released by target cells in the absence of antibody or NK cell. Positive control: Calcein released by target cells upon lysis by detergent (1% NP40).

The results illustrated in FIGS. 2 and 3 show that CHIR-12.12 mediates greater ADCC than rituximab against CLL patient cells. The magnitude of the ADCC difference may depend on either the target cells or the NK donor cells but was observed against all patient samples. When CLL cells from single patient were tested with two different NK donors, CHIR-12.12 mediated greater ADCC than rituximab for both NK donor cells, although the magnitude of the differential ADCC was not identical (see FIG. 4). The mechanistic basis for this superior ADCC might include the relative expression levels of the target antigens (CD20 and CD40), the extent of internalization of the antibody, and the affinity of the antibody for the FcγIIIa receptor on NK cells. Therefore the influence of these factors on the ADCC activity of CHIR-12.12 and rituximab was investigated.

Example 3

Quantitation of Cell-Surface CD40 and CD20 Molecules

Quantitative CD20 and CD40 density on CLL cells (Example 3) and the degree of antibody internalization (Example 4) were investigated as potential reasons for the above-described difference in ADCC activity. The relative ADCC activity of CHIR-12.12 and rituximab against ex vivo primary CLL cells from 9 patients was then compared. CHIR-12.12 exhibited greater ADCC than rituximab against CLL from all patients (see FIG. 2A-D and FIG. 3). The average percent maximum lysis by CHIR-12.12 and rituximab were 48±15% and 30±14%, respectively. CHIR-12.12 was greater than 10-fold more potent than rituximab, as measured by ED50 values (13.2 pM versus 147.2 pM, respectively, FIG. 6).

The greater ADCC activity and efficacy of CHIR-12.12 was not dependent on a higher density of cell surface CD40 molecules, as there were 1.3- to 14-fold higher numbers of CD20 than CD40 molecules on the cell surface (see FIG. 5 and FIG. 6).

Methods

Cells were preincubated with human IgG1 at 1 mg/ml in staining buffer (PBS contains 1% BSA, 0.1% Na Azide) to block non-specific binding sites. They were incubated for 30 minutes at 4° C. (on ice). Then FITC-conjugated human IgG1 isotype control, FITC-conjugated CHIR-12.12, or FITC-conjugated rituximab was added at 100, 10, 1, 0.1 µg/ml, and cells were incubated for 30 minutes at 4° C. (on ice). Cells were washed with staining buffer (PBS+1% FBS+0.1% Sodium Azide), and analyzed by FACS Calibur.

Geometric mean fluorescence intensity was measured by FACS. Molecules of Equivalent Soluble Fluorchrome (MESF) were then calculated based on the standard curve established by calibrated FITC beads.

Example 4

CH12.12 does not Induce Internalization Upon Binding to CD40 on Cell Lines

Daudi, a lymphoma cell line, and ARH77, an MM cell line, were used to evaluate the effect of CH12.12 binding on internalization. Cells were incubated with human IgG1 (control antibody) or CH12.12 at 1 µg/mL on ice (with 0.1% sodium azide to block internalization) or 37° C. (without sodium azide) for 3 hours. After a wash with cold staining buffer (PBS+1% BSA+0.1% sodium azide), cells were stained with goat anti-human IgG-FITC for 30 minutes on ice. Geometric mean fluorescent intensity (MFI) was recorded by FACS Calibur. No difference in MFI was observed between cells incubated with CH12.12 on ice in the presence of sodium azide or at 37° C. in the absence of sodium azide (FIG. 7). These data show that CH12.12, upon binding to CD40, is not internalized and continues to be displayed on the cell surface.

Example 5

Internalization of CHIR-12.12 and Rituximab Following Binding to CLL Patient Cells: FACS and Confocal Microscope Confocal Microscope Methodology Cells were incubated with Alexa 488 or FITC conjugated CHIR-12.12, rituximab, and IgG1 at 10 µg/ml, for 3 hrs at 40° C. (with 0.1% Na azide) or 37° C. (w/o Na azide). Cells were then washed and fixed with 2% formaldehyde, 5 min RT. Cells were then washed and placed on poly-L-lysine coated slides, mounted, and sealed, and then analyzed by confocal imaging.

Results

The results of these experiments are illustrated in FIG. 8 (FACS) and FIGS. 9 and 10 (confocal microscope). The results from these experiments are summarized in FIG. 11. These antibody internalization studies using primary CLL cells and B cells conducted by flow cytometry and confocal microscopy show that upon binding to CD40 at 37° C., CHIR-12.12 remains uniformly distributed on the cell surface, even after 3 hours. In contrast, after binding at 37° C., rituximab is redistributed into caps and internalized. These data suggest that the potent ADCC activity of CHIR-12.12 may be related to its ability to display itself uniformly on the surface of target cells, allowing optimal interaction with effector cells. These results suggest that CHIR-12.12 may be effective at mediating potent ADCC against CLL cells in vivo.

Example 6

Biacore Analysis of FcγRIIIa Binding by Rituxan® and CHIR-12.12

The affinities of the FcγRIIIa aa158F and aa158V alleles for CHIR-12.12 and rituximab were compared by standard Biacore® analysis. CHIR-12.12 bound the aa158F allele with a 4.6-fold higher affinity when compared with rituximab ($K_D$ of 2.8 µM versus 13 µM, respectively). The results of these experiments are summarised in the following table:

| | $K_D$ (nM) | |
|---|---|---|
| | CHIR-12.12 | Rituximab |
| FcγRIIIa 158V | 492 | 466 |
| FcγRIIIa 158F | 2800 | 13000 |

Example 7

The Effect of FcγRIIIa Polymorphism on ADCC by NK Effector Cells

Antibody-dependent cellular cytotoxicity (ADCC) is a major mechanism of action for many marketed and investigational monoclonal antibodies. Rituximab (Rituxan®), marketed for the treatment of follicular non-Hodgkin's lymphoma (NHL) and active in other B-cell malignancies, is thought to have ADCC as one of its primary mechanisms of action. Notably, the clinical activity of rituximab in NHL has been shown to be correlated with the FcγRIIIa genotype. Patients with the FcγRIIIa 158aa polymorphism of V/V or V/F are more responsive to rituximab than those with F/F (for example, see Cartron et al. (Blood (2002), 99(3): 754-758 or Dall'Ozzo et al. Cancer Res. (2004) 64:4664-4669).

Figure 12:
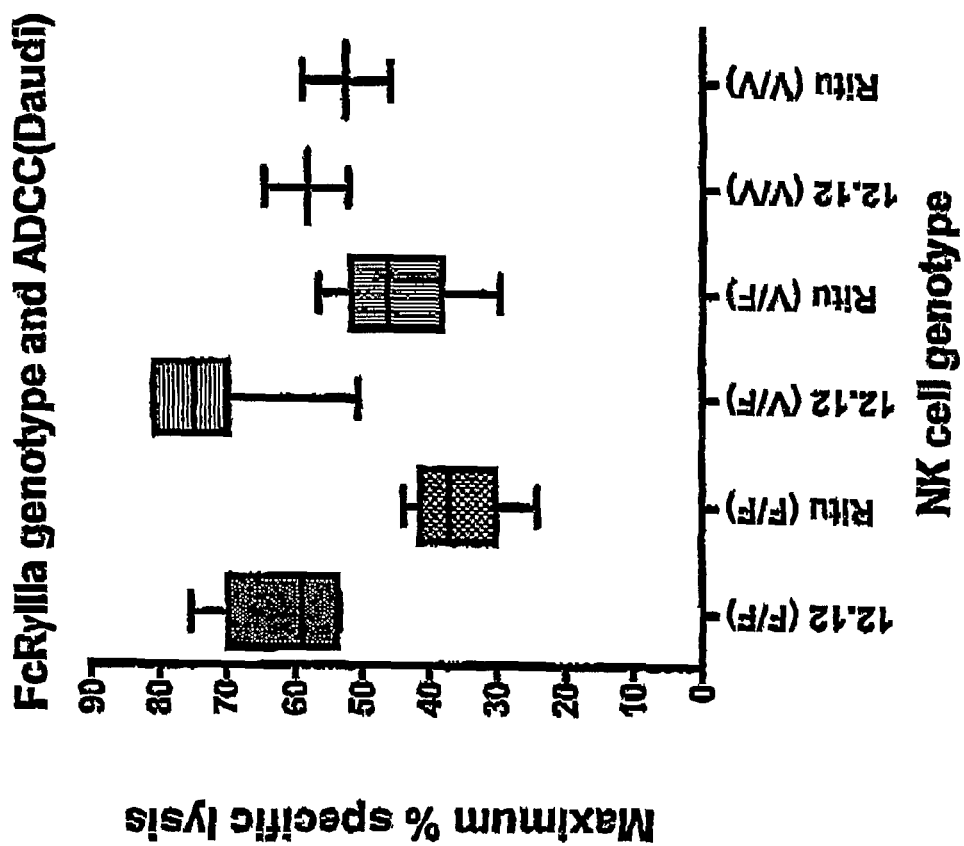
FIG. 12 is a bar chart showing maximum percentage specific lysis of Daudi cells by CHIR-12.12 or rituximab by purified NK effector cells from donors with different FcγRIIIa genotypes.
Figure 13:
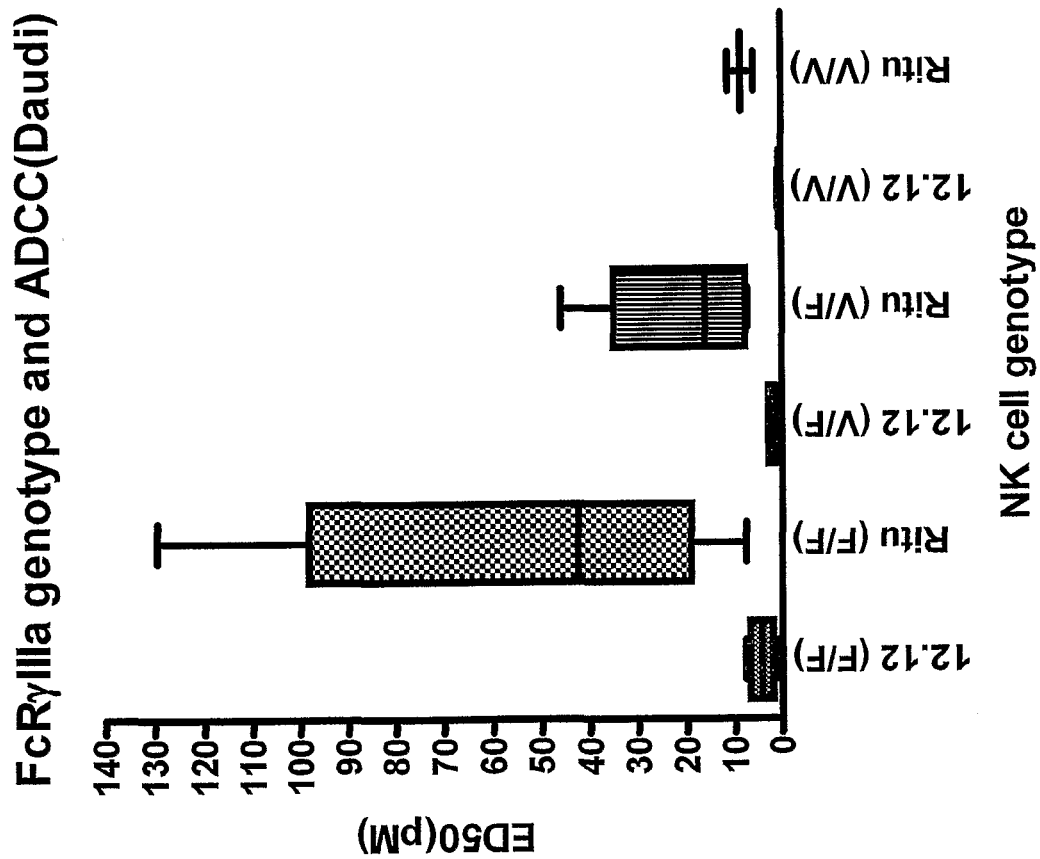
FIG. 13 is a bar chart showing ADCC potency ($ED_{50}$) of CHIR-12.12 or rituximab on Daudi cells by in purified NK effector cells from donors with different FcγRIIIa genotypes.

In these experiments, purified NK effector cells from multiple human donors expressing various FcγRIIIa aa158 polymorphisms were evaluated using the human lymphoma Daudi cell line as the target cells (see FIGS. 12 and 13). As illustrated by those figures, CHIR-12.12 induced potent ADCC with NK cells of all three genotypes. The CHIR-12.12 $ED_{50}$s for lysis of the Daudi cell line were 4, 2, and 0.4 pM for F/F, V/F and V/V, respectively (FIG. 13). The rituximab $ED_{50}$s for lysis of the Daudi cell line were 53, 21, and 9 pM for F/F, V/F, and V/V, respectively (FIG. 13).

Purified NK effector cells from multiple human donors expressing various FcγRIIIa aa158 polymorphisms were also evaluated using the CLL patient cells as the target cells (see FIG. 14). CHIR-12.12 was found to be a more potent mediator of ADCC than rituximab against all CLL patient cells tested (FIG. 14). These data suggest that CHIR-12.12 is a more potent ADCC mediator than rituximab, even with NK cells of the aa158 V/F or F/F genotype.

These findings are surprising because it would have been expected that CHIR-12.12 would be significantly less potent in ADCC assays using NK cells with the FcγRIIIa 158aa polymorphism of F/F or V/F than those with V/V. Again, the clinical activity of rituximab in NHL has been shown to be correlated with the FcγRIIIa genotype. Patients with the FcγRIIIa 158aa polymorphism of V/V or V/F are more responsive to rituximab than those with F/F. Rituximab is also an IgG1 monoclonal antibody that binds to an antigen expressed on the surface of B cells, and so it would have been expected that CHIR-12.12 would display the same preference for the FcγRIIIa-158 V polymorphism. Instead, it was found that CHIR-12.12 induces potent ADCC with NK cells of all three genotypes.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications cited herein are incorporated in full by reference to the same extent as if each individual publication or patent application was specifically and individually indicated to be incorporated by reference.

That which is claimed:

1. A method for treating a human patient for a cancer or pre-malignant condition that is associated with cells expressing both CD40 and CD20 and which is refractory to treatment with rituximab (Rituxan®), said method comprising:
   a) genotyping a biological sample obtained from said human patient to determine said human patient's FcγRIIIa-158 genotype (V/V, V/F, or F/F);
   b) identifying said human patient as being heterozygous or homozygous for FcγRIIIa-158F (genotype V/F or F/F), and
   c) administering to said human patient identified as being heterozygous or homozygous for FcγRIIIa-158F (genotype V/F or F/F) a therapeutically or prophylactically effective amount of an anti-CD40 antibody that mediates antibody-dependent cellular cytotoxicity (ADCC) against CD40-expressing cells,
   wherein said treating results in at least one positive therapeutic response in said patient with respect to said cancer or pre-malignant condition.

2. A method according to claim 1, wherein said cancer or pre-malignant condition is a cancer of B-cell lineage.

3. A method according to claim 2, wherein said cancer of B-cell lineage is selected from the group consisting of acute lymphoblastic leukemia (ALL), chronic lymphocytic leukemia (CLL), prolymphocytic leukemia (PLL), small lymphocytic leukemia (SLL), hairy cell leukemia, Hodgkin's disease, multiple myeloma, Waldenstrom's macroglobulinemia, heavy chain disease, and lymphomas.

4. A method according to claim 1, wherein said cancer or pre-malignant condition is a non-B cell hematological malignancy.

5. A method according to claim 4, wherein said non-B cell hematological malignancy is acute myelocytic leukemia.

6. A method according to claim 1, wherein said cancer or pre-malignant condition is a solid tumor.

7. A method according to claim 6, wherein the solid tumor is selected from the group consisting of ovarian, lung, breast, colon, kidney, bladder, liver, gastric, cervical, prostate, nasopharyngeal, thyroid, and skin cancers, and sarcomas.

8. A method according to claim 1, wherein said anti-CD40 antibody is administered by a parenteral route of administration.

9. A method according to claim 8, wherein said anti-CD40 antibody is administered intravenously or subcutaneously.

10. A method according to claim 1, wherein said anti-CD40 antibody is a human monoclonal antibody.

11. A method according to claim 10, wherein said human anti-CD40 monoclonal antibody comprises a human IgG1 heavy chain constant region.

12. A method according to claim 11, wherein said human anti-CD40 monoclonal antibody comprises the amino acid sequence recited in SEQ ID NO:4 or SEQ ID NO:5.

13. A method according to claim 1, wherein said anti-CD40 antibody is free of significant agonist activity.

14. A method according to claim 1, wherein said anti-CD40 antibody is an antagonist of CD40-CD40L signaling on CD40-expressing cells.

15. A method according to claim 1, wherein said anti-CD40 antibody is more potent than rituximab (Rituxan®) in an assay of antibody-dependent cellular cytotoxicity (ADCC), wherein the assay comprises incubating CD40-expressing cells and CD20-expressing cells with isolated human natural killer (NK) cells in the presence of the relevant antibody.

16. A method according to claim 1, wherein said anti-CD40 antibody is more potent than rituximab (Rituxan®) in a nude mouse xenograft tumor model.

17. A method according to claim 16, wherein said nude mouse xenograft tumor model uses the Daudi human lymphoma cell line of a myeloma cell line.

18. A method according to claim 1, wherein said anti-CD40 antibody binds to human CD40 with an affinity ($K_D$) of at least about $10^{-6}$ M to at least about $10^{-12}$ M.

19. A method according to claim 1, wherein said anti-CD40 antibody binds to human FcγRIIIa-158V with an affinity ($K_D$) of at least about 0.5 μM.

20. A method according to claim 1, wherein said anti-CD40 antibody binds to human FcγRIIIa-158F with an affinity ($K_D$) of at least about 12 μM.

21. A method according to claim 1, wherein said anti-CD40 antibody binds to human FcγRIIIa-158V with an affinity ($K_D$) of at least about 0.5 μM, and binds to human FcγRIIIa-158F with an affinity (KD) of at least about 12 μM.

22. The method of claim 1, wherein said anti-CD40 antibody is a monoclonal antibody comprising an amino acid sequence selected from the group consisting of:
   (a) SEQ ID NO:2;
   (b) SEQ ID NO:4;
   (c) SEQ ID NO:5;
   (d) SEQ ID NO:2 and SEQ ID NO:4; and
   (e) SEQ ID NO:2 and SEQ ID NO:5.

23. The method of claim 1, wherein said anti-CD40 antibody is selected from the group consisting of:
   (a) a monoclonal antibody comprising the variable and constant region sequences shown in SEQ ID NO:2;
   (b) a monoclonal antibody comprising the variable and constant region sequences shown in SEQ ID NO:4;
   (c) a monoclonal antibody comprising the variable and constant region sequences shown in SEQ ID NO:5;
   (d) a monoclonal antibody comprising the variable and constant region sequences shown in SEQ ID NO:2 and the variable and constant region sequences shown SEQ ID NO:4; and
   (e) a monoclonal antibody comprising the variable and constant region sequences shown in SEQ ID NO:2 and the variable and constant region sequences shown SEQ ID NO:5.

24. The method of claim 1, wherein said anti-CD40 antibody is the antibody CHIR-12.12 produced by the hybridoma cell line deposited with the ATCC as Patent Deposit No. PTA-5543.

25. The method of claim 1, wherein said anti-CD40 antibody comprises:
   (a) a light chain variable domain containing the complementarity determining region (CDR) residues of SEQ ID NO:2; and
   (b) a heavy chain variable domain containing the CDR residues of SEQ ID NO:4.

26. A method according to claim 3, wherein said lymphoma is selected from the group consisting of diffuse small lymphocytic lymphoma, follicular lymphoma, diffuse large B-cell lymphoma (DLBCL), mucosal associated lymphoid tissue lymphoma, monocytoid B cell lymphoma, splenic lymphoma, lymphomatoid granulomatosis, intravascular lymphomatosis, immunoblastic lymphoma, and AIDS-related lymphoma.

27. A method according to claim 7, wherein said lung cancer is a non-small cell lung cancer of the squamous cell carcinoma, adenocarcinoma, or large cell carcinoma type.

28. A method according to claim 7, wherein the said lung cancer is a small cell lung cancer.

29. A method according to claim 7, wherein said kidney cancer is renal cell carcinoma.

30. A method according to claim 7, wherein said liver cancer is hepatocellular carcinoma.

31. A method according to claim 7, wherein said thyroid cancer is thyroid papillary carcinoma.

32. A method according to claim 7, wherein said skin cancer is melanoma.

33. A method according to claim 6, wherein the solid tumor is a sarcoma.

34. A method according to claim 33, wherein said sarcoma is osteosarcoma or Ewing's sarcoma.

\* \* \* \* \*